US012298312B2

(12) United States Patent
Shah et al.

(10) Patent No.: US 12,298,312 B2
(45) Date of Patent: May 13, 2025

(54) DETECTION OF LYME DISEASE

(71) Applicant: ID-Fish Technology, Inc., Milpitas, CA (US)

(72) Inventors: Jyotsna S. Shah, Santa Clara, CA (US); Song Liu, San Jose, CA (US); Sudhir Shah, Santa Clara, CA (US)

(73) Assignee: ID-Fish Technology, Inc., Milpitas, CA (US)

(*) Notice: Subject to any disclaimer, the term of this patent is extended or adjusted under 35 U.S.C. 154(b) by 365 days.

(21) Appl. No.: 17/229,773

(22) Filed: Apr. 13, 2021

(65) Prior Publication Data

US 2021/0325393 A1 Oct. 21, 2021

Related U.S. Application Data

(60) Provisional application No. 63/009,216, filed on Apr. 13, 2020.

(51) Int. Cl.
*G01N 33/577* (2006.01)
*G01N 33/535* (2006.01)

(52) U.S. Cl.
CPC ......... *G01N 33/577* (2013.01); *G01N 33/535* (2013.01); *G01N 2333/916* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | | |
|---|---|---|---|---|
| 9,816,991 | B2 * | 11/2017 | Dattwyler | A61P 31/04 |
| 2009/0162875 | A1 | 6/2009 | Dattwyler et al. | |
| 2015/0017666 | A1 | 1/2015 | Dattwyler et al. | |

FOREIGN PATENT DOCUMENTS

| | | | |
|---|---|---|---|
| WO | 9859071 | A1 | 6/1998 |
| WO | 2008031133 | A2 | 3/2008 |
| WO | 2011112805 | A2 | 9/2011 |
| WO | 2012047607 | A2 | 4/2012 |
| WO | 2019224275 | A1 | 11/2019 |

OTHER PUBLICATIONS

ThermoFisher Scientific, Antibody Production, available online at: https://www.thermofisher.com/us/en/home/life-science/antibodies/antibodies-learning-center/antibodies-resource-library/antibody-methods/antibody-production-immunogen-preparation.html. Accessed: Jul. 15, 2023 (8 pages) (Year: 2023).*

White HN (2021), "B-Cell Memory Responses to Variant Viral Antigens", Viruses, 13, 4, 11 pages (Year: 2021).*

Brunner M, Sigal LH (Aug. 2000) "Immune Complexes from Serum of Patients with Lyme Disease Contain Borrelia burgdorferi Antigen and Antigen-Specific Antibodies: Potential Use for Improved Testing", The Journal of Infectious Diseases, 182, 2, pp. 534-539 (Year: 2000).*

Liu S, Cruz ID, Ramos CC, Taleon P, Ramasamy R, Shah J. (2018), "Pilot Study of Immunoblots with Recombinant Borrelia burgdorferi Antigens for Laboratory Diagnosis of Lyme Disease", Healthcare, 6, 3, 15 pages (Year: 2018).*

C6 SEQ ID No. 45 aa 1 25 Bb B31, https://blast.ncbi.nlm.nih.gov/Blast.cgi#AET25136 (Year: 2023).*

C6 SEQ ID No. 45 aa 28 59 BB 297, https://blast.ncbi.nlm.nih.gov/Blast.cgi#MCR8909861, accessed Aug. 7, 2023 (Year: 2023).*

C6 SEQ ID No. 45 aa 60 84 B garinii, https://blast.ncbi.nlm.nih.gov/Blast.cgi#alnHdr_WP_210377670, accessed Aug. 7, 2023 (Year: 2023).*

C6 SEQ ID No. 45 aa 89 114 afzelii, https://blast.ncbi.nlm.nih.gov/Blast.cgi#alnHdr_APJ09206, accessed Aug. 7, 2023 (Year: 2023).*

C6 SEQ ID No. 45 aa 118 142 spielmanii, https://blast.ncbi.nlm.nih.gov/Blast.cgi#alnHdr_CAQ52814, accessed Aug. 7, 2023 (Year: 2023).*

Harlow E, Lane D (1988), Antibodies, A Laboratory Manual, Cold Spring Harbor laboratory pp. 25-26 and 37-59 (Year: 1988).*

Margos G, Wilske B, Sing A, Hizo-Teufel C, Caoa WC, Chu C, Schholz H, Straubinger RK, Fingerle V (2013), "*Borrelia bavariensis* sp. Nov. is widely distributed in Europe and Asia", International Journal of Systematic and Evolutionary Microbiology, 63, pp. 4284-4288 (Year: 2013).*

Cameron, et al. "Evidence assessments and guideline recommendations in Lyme disease: the clinical management of known tick bites, erythema migrans rashes and persistent disease" Expert Reviews; 2014; 33 pages.

Shah, et al. "Line Immunoblot Assay for Tick-Borne Relapsing Fever and Findings in Patient Sera from Australia, Ukraine and the USA" Healthcare; 2019; vol. 7; No. 121; 17 pages.

Liu, et al. "Pilot Study of Immunoblots with Recombinant Borrelia burgdorferi Antigens for Laboratory Diagnosis of Lyme Disease" Healthcare; 2018; vol. 6; No. 99; 15 pages.

Stricker, et al. "Chronic Lyme Disease: A Working Case Definition" American Journal of Infectious Diseases; 2018; 44 pages.

Jin, et al. "An Enhanced ELISPOT Assay for Sensitive Detection of Antigen-Specific T Cell Responses to Borrelia burgdorferi" Cells; 2013; vol. 2; 14 pages.

Partial Supplementary European Search Report from the European Patent Office dated Jun. 10, 2024 from corresponding European Patent Application No. 21788688.6.

* cited by examiner

*Primary Examiner* — Gregory S Emch
*Assistant Examiner* — Stefanie J. Kirwin
(74) *Attorney, Agent, or Firm* — Pierce Atwood LLP

(57) ABSTRACT

The disclosure, in some aspects, provides antigen-specific amino acid sequences for *Borrelia burgdorferi* sensu lato species.

20 Claims, 5 Drawing Sheets

Specification includes a Sequence Listing.

P23 Alignment

P31 Alignment

P39 Alignment

DETECTION OF LYME DISEASE

RELATED APPLICATIONS

This application claims the benefit under 35 U.S.C. § 119(e) of U.S. Provisional application Ser. No. 63/009,216, filed Apr. 13, 2020, the disclosure of which is incorporated by reference herein in its entirety.

FIELD OF THE INVENTION

Aspects of the present disclosure provide novel compositions and methods for identifying antibodies resulting from infection by diverse *Borrelia* species.

SEQUENCE LISTING

The instant application incorporates by reference the Sequence Listing in the ASCII text file filed Apr. 13, 2021, entitled "ID-FISH 0153-2016US02_ST25.txt", which file was created on Apr. 13, 2021, the size of which file is 179,900 bytes.

BACKGROUND

With more than 300,000 new cases reported each year in the USA, Lyme disease is a major public health concern. *Borrelia burgdorferi* sensu stricto (Bbss) is considered the primary agent of Lyme disease in North America. The CDC states that approximately 30,000 cases of Lyme disease are reported in the USA each year using surveillance criteria featuring two-tier Bbss testing, but when tracked by other methods it is estimated that more than 300,000 people develop Lyme disease in the USA annually. The fact that CDC surveillance criteria featuring two-tier Bbss testing captures less than one out of every ten cases shows that Lyme disease is underreported.

SUMMARY

According to an aspect of the disclosure, a panel for detecting IgM- or IgG-class antibodies is provided, the panel including SEQ ID NO: 45 and a plurality of groups of labelled and/or tagged and/or bound amino acid sequences, wherein the labelled and/or tagged and/or bound amino acid sequences include amino acid sequences and variants thereof which retain the immunological binding profile of the corresponding non-variant, and wherein the plurality of groups of labelled and/or tagged and/or bound amino acid sequences is selected from the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32, and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43. In some aspects, the labelled and/or tagged and/or bound amino acid sequences are bound to a substance selected from the group consisting of nitrocellulose, nylon, polyvinylidene difluoride (PVDF), magnetic beads, and agarose. In other aspects, the panel further includes one or more of SEQ ID NO: 44 and SEQ ID NO: 46, and variants thereof which retain the immunological binding profile of the corresponding non-variant. In some aspects, each of the one or more amino acid sequences are tagged with an antibody with specificity for the amino acid sequence.

According to another aspect of the disclosure, a method for detecting IgM- or IgG-class antibodies resulting from infection by one or more *Borrelia burgdorferi* sensu lato (Bbsl) species, if present in a biological sample obtained from a subject suspected of having Lyme disease is provided, the method including: (a) providing a screening panel including SEQ ID NO: 45 and a plurality of groups of labelled and/or tagged and/or bound amino acid sequences, wherein the labelled and/or tagged and/or bound amino acid sequences include amino acid sequences and variants thereof which retain the immunological binding profile of the corresponding non-variant, and wherein the plurality of groups of labelled and/or tagged and/or bound amino acid sequences is selected from the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32, and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43; (b) providing the biological sample obtained from the subject suspected of having Lyme disease; (c) contacting the biological sample with the screening panel of step (a) under conditions appropriate for specific antibody binding to an epitope; and (d) detecting specific binding of IgM- or IgG-class antibodies, if present in the biological sample, with amino acid sequences included in the selected groups of the screening panel of step (a), wherein the sample is scored as positive for infection by one or more Bbsl species when: (1) a positive immunobinding reaction with IgM-class antibodies is detected for SEQ ID NO: 45 and for at least one amino acid sequence from at least two of groups (i)-(iii), (2) a positive immunobinding reaction with IgG-class antibodies is detected for SEQ ID NO: 45 and for at least one amino acid sequence from at least five of groups (i)-(iv) and (vii)-(xii), (3) a positive immunobinding reaction with IgM-class antibodies is detected for SEQ ID NO: 45 and for at least one amino acid sequence from at least two of groups (i)-(iii) and (v), or (4) a positive immunobinding reaction with IgG-class antibodies is detected for SEQ ID NO: 45 and for at least one amino acid sequence from at least two of groups (i)-(vi), and wherein a positive score for infection indicates the presence of antibodies to one or more Bbsl species in the subject. In some aspects, the binding of IgM-class antibodies is detected through the use of an anti-human IgM antibody linked to a detectable moiety. In some aspects, the binding of IgG-class antibodies is detected through the use of an anti-human IgG antibody linked to a detectable moiety. In some aspects, the detectable moiety is selected from the group consisting of chromophores, radioactive moieties, and enzymes. In other aspects, the detectable moiety includes alkaline phosphatase. In some aspects, the detectable moiety includes biotin. In some aspects, the one or more Bbsl species include *B. afzelii, B, garinii, B.*

*californiensis, B. spielmanii, B. mayonii, B. valaisiana, B. bavariensis, B. burgdorferi* B31, and *B. burgdorferi* 297. In some aspects, the screening panel of step (a) further includes at least one or more of SEQ ID NO: 44 and SEQ ID NO: 46, and variants thereof which retain the immunological binding profile of the corresponding non-variant.

According to yet another aspect of the disclosure, a method for detecting IgM-class and IgG-class antibodies resulting from infection by one or more *Borrelia burgdorferi* sensu lato (Bbsl) species, if present in a biological sample obtained from a subject suspected of having Lyme disease is provided, the method including: (a) providing a screening panel including SEQ ID NO: 45 and a plurality of groups of labelled and/or tagged and/or bound amino acid sequences, wherein the labelled and/or tagged and/or bound amino acid sequences include amino acid sequences and variants thereof which retain the immunological binding profile of the corresponding non-variant, and wherein the plurality of groups of labelled and/or tagged and/or bound amino acid sequences is selected from the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23. SEQ ID NO: 24, SEQ ID NO: 25, and SEQ ID NO: 26; (iii) SEQ ID NO: 32, and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43; (b) providing the biological sample obtained from the subject suspected of having Lyme disease; (c) contacting the biological sample with the screening panel of step (a) under conditions appropriate for specific antibody binding to an epitope; and (d) detecting specific binding of IgM-class and IgG-class antibodies, if present in the biological sample, with amino acid sequences included in the selected groups of the screening panel of step (a), wherein the sample is scored as positive for infection by one or more Bbsl species when a positive immunobinding reaction with IgM-class or IgG-class antibodies is detected for SEQ ID NO: 45 and: (1)(A) a positive immunobinding reaction with IgM-class antibodies is detected for at least one amino acid sequence from at least two of groups (i)-(iii), and (1)(B) a positive immunobinding reaction with IgG-class antibodies is detected for at least one amino acid sequence from at least five of groups (i)-(iv) and (vii)-(xii); or (2)(A) a positive immunobinding reaction with IgM-class antibodies is detected for at least one amino acid sequence from at least two of groups (i)-(v), and (2)(B) a positive immunobinding reaction with IgG-class antibodies is detected for at least one amino acid sequence from at least two of groups (i)-(vi), and wherein a positive score for infection indicates the presence of antibodies to one or more Bbsl species in the subject. In some aspects, the binding of IgM-class antibodies is detected through the use of an anti-human IgM antibody linked to a detectable moiety. In some aspects, the binding of IgG-class antibodies is detected through the use of an anti-human IgG antibody linked to a detectable moiety. In some aspects, the detectable moiety is selected from the group consisting of chromophores, radioactive moieties, and enzymes. In other aspects, the detectable moiety includes alkaline phosphatase. In some aspects, the detectable moiety includes biotin. In some aspects, the one or more Bbsl species include *B. afzelii, B. garinii, B. californiensis, B. spielmanii, B. mayonii, B. valaisiana, B. bavariensis, B. burgdorferi* B31, and *B. burgdorferi* 297. In some aspects, the screening panel of step (a) further includes at least one or more of SEQ NO: 44 and SEQ ID NO: 46, and variants thereof which retain the immunological binding profile of the corresponding non-variant.

According to another aspect of the disclosure, a method for detecting IgM- or IgG-class antibodies resulting from infection by one or more *Borrelia burgdorferi* sensu lato (Bbsl) species, if present in a biological sample obtained from a subject suspected of having Lyme disease is provided, the method including: (a) providing a screening panel including a plurality of groups of labelled and/or tagged and/or bound amino acid sequences, wherein the labelled and/or tagged and/or bound amino acid sequences include amino acid sequences and variants thereof which retain the immunological binding profile of the corresponding non-variant, and wherein the plurality of groups of labelled and/or tagged and/or bound amino acid sequences is selected from the following groups: (i) SEQ ID NO: 1, SEQ ID NO: 2; SEQ ID NO: 3; SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32, and SEQ ID NO: 33; (iv) SEQ ID NO: 27 and SEQ ID NO: 28; (v) SEQ ID NO: 11; SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37; SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43; (b) providing the biological sample obtained from the subject suspected of having Lyme disease; (c) contacting the biological sample with the screening panel of step (a) under conditions appropriate for specific antibody binding to an epitope; and (d) detecting specific binding of IgM- or IgG-class antibodies, if present in the biological sample, with amino acid sequences included in the selected groups of the screening panel of step (a), wherein the sample is scored as positive for infection by one or more Bbsl species when: (1) a positive immunobinding reaction with IgM-class antibodies is detected for at least one amino acid sequence from at least two of groups (i)-(iii), (2) a positive immunobinding reaction with IgG-class antibodies is detected for at least one amino acid sequence from at least five of groups (i)-(iv) and (vii)-(xii), (3) a positive immunobinding reaction with IgM-class antibodies is detected for at least one amino acid sequence from at least two of groups (i)-(iii) and (v), or (4) a positive immunobinding reaction with IgG-class antibodies is detected for at least one amino acid sequence from at least two of groups (i)-(vi), and wherein a positive score for infection indicates the presence of antibodies to one or more Bbsl species in the subject. In some aspects, the binding of IgM-class antibodies is detected through the use of an anti-human IgM antibody linked to a detectable moiety. In some aspects, the binding of IgG-class antibodies is detected through the use of an anti-human IgG antibody linked to a detectable moiety. In some aspects, the detectable moiety is selected from the group consisting of chromophores, radioactive moieties, and enzymes. In other aspects, the detectable moiety includes alkaline phosphatase. In some aspects, the detectable moiety includes biotin. In some aspects, the one or more Bbsl species include *B. afzelii, B. garinii, B. californiensis, B. spielmanii, B.*

*mayonii, B, valaisiana, B. bavariensis, B. burgdorferi* B31, and *B. burgdorferi* 297. In some aspects, the screening panel of step (a) further includes at least one or more of SEQ ID NO: 44, SEQ ID NO: 45, and SEQ ID NO: 46, and variants thereof which retain the immunological binding profile of the corresponding non-variant.

BRIEF DESCRIPTION OF THE DRAWINGS

FIG. 1A shows an alignment of the 23 kDa, protein (P23, SEQ ID NOs: 47-56). FIG. 1B shows an alignment of the 31 kDa protein (P31, SEQ ID NOs: 57-66). FIG. 1C shows an alignment of 39 kDa, (P39, SEQ ID NOs: 67-73).

DESCRIPTION OF THE SEQUENCES

P23 *B. burgdorferi* B31

SEQ ID NO: 1

Figure 1A:
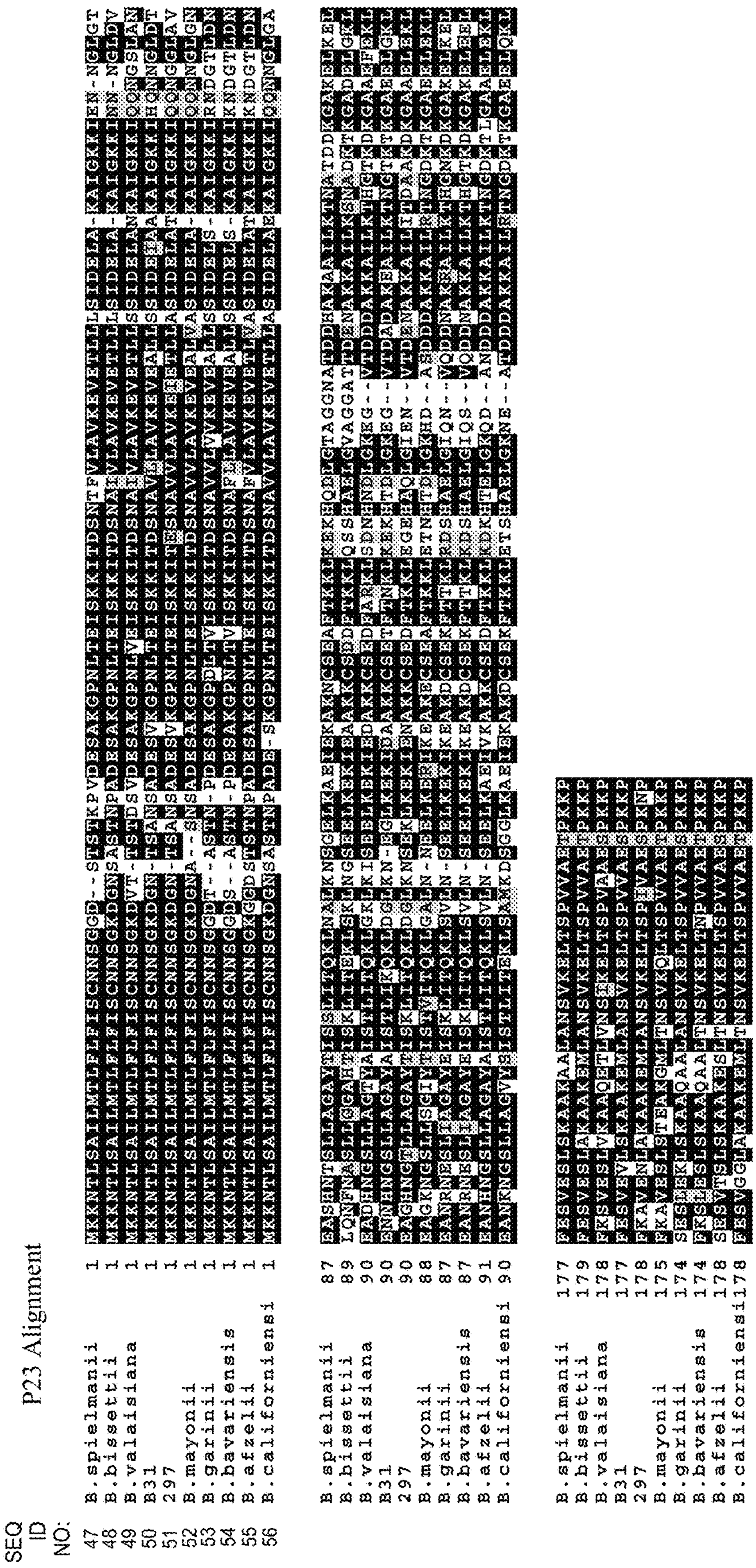
FIGS. 1A-C present schematics of amino acid sequence alignments of selected Bbsl antigenic polypeptides among multiple Bbsl species.
Figure 1B:
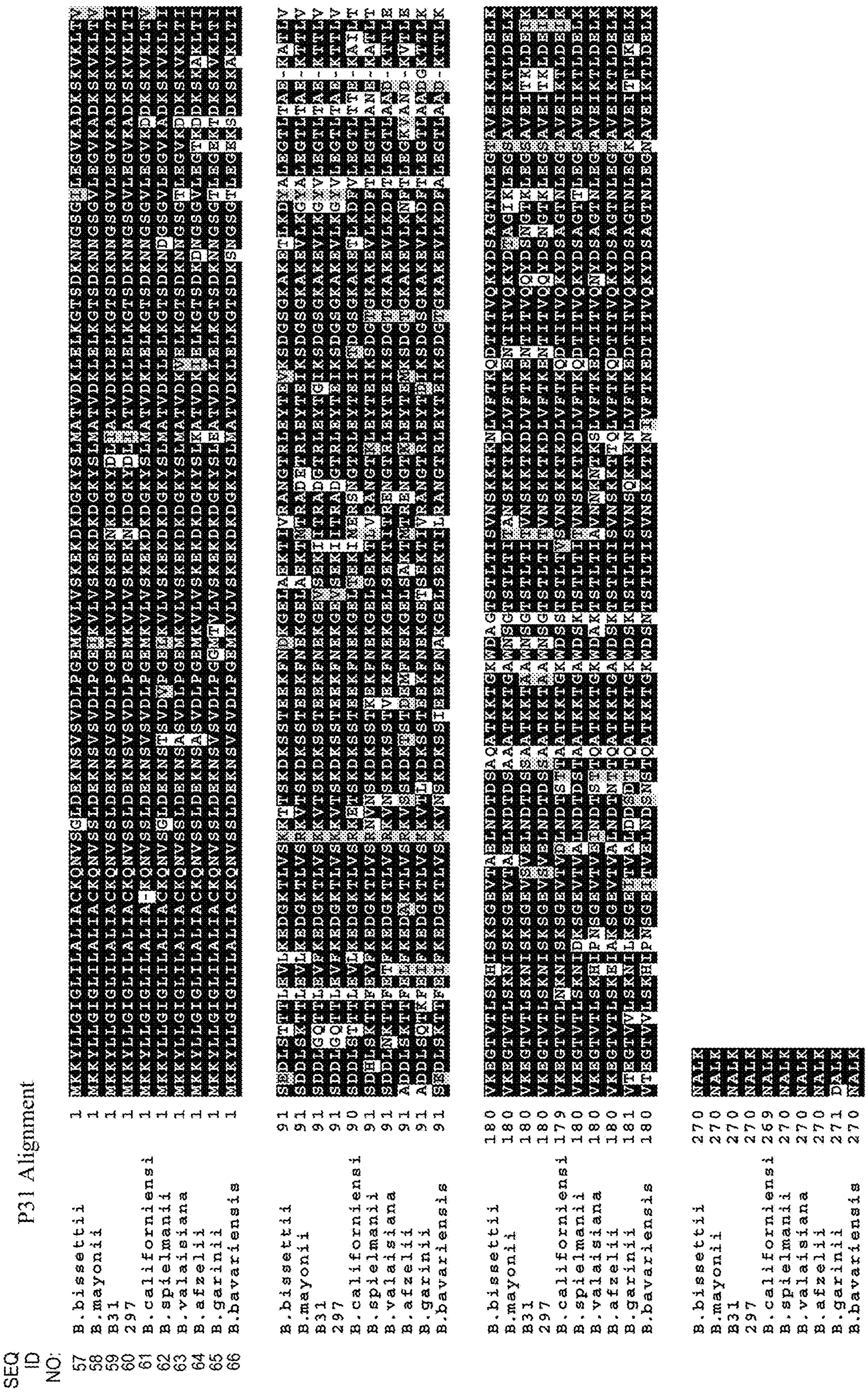
Figure 1C:
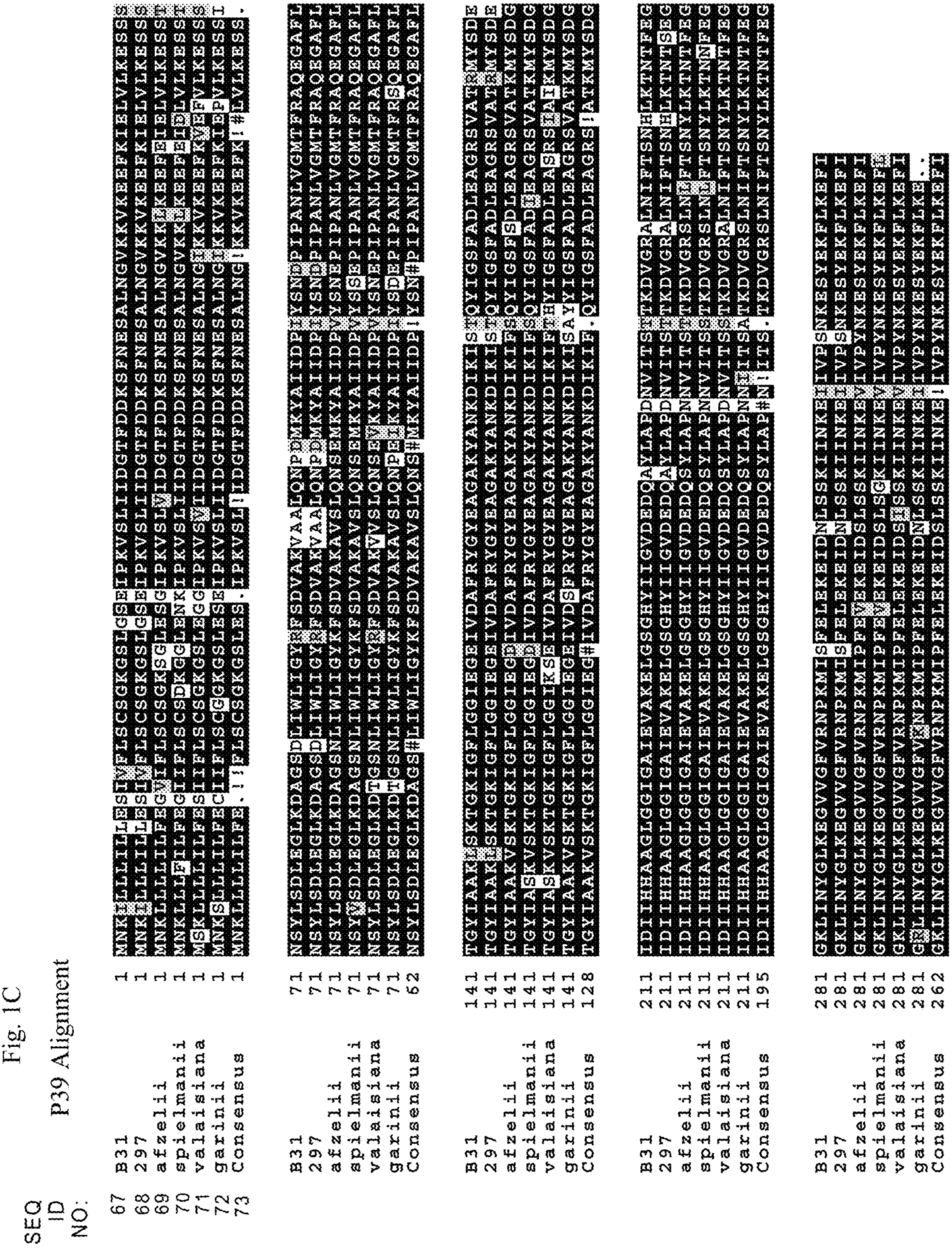

MFLFISCNNSGKDGNTSANSADESVKGPNLTEISKKITDSNAVLLAVKEVE
ALLSSIDEIAAKAIGKKIHQNNGLDTENNHNGSLLAGAYAISTLIKQKLDG
LKNEGLKEKIDAAKKCSETFTNKLKEKHTDLGKEGVTDADAKEAILKTNGT
KTKGAEELGKLFESVEVLSKAAKEMLANSVKELTSPVVAESPKKP.

P23 *B. burgdorferi* 297

SEQ ID NO: 2

MFLFISCNNSGKDGNTSANSADESVKGPNLTEISKKITESNAVVLAVKEVE
TLLTSIDELAKAIGKKIKNDVSLDNEADHNGSLISGAYLISTLITKKISAI
KDSGELKAEIEKAKKCSEEFTAKLKGEHTDLGKEGVTDDNAKKAILKTNND
KTKGADELEKLFESVKNLSKAAKEMLTNSVKELTSPVVAESPKNPGSVDK
L.

-continued

P23 *B. bissettii*

SEQ ID NO: 3

MFLFISCNNSGKDGNSASTNPADESAKGPNLTEISKKITDSNAIVLAVKEV
ETLLLSIDELAKAIGKKINNNGLDVLQNFNASLLGGAHTISKLITEKLSKL
NGSEELKEKIEAAKKCSDDFTKKLQSSHAELGVAGGATTDENAKKAILKSN
ADKTKGADELGKLFESVESLAKAAKEMLANSVKELTSPVVAETPKKP.

P23 *B. californiensis*

SEQ ID NO: 4

MFLFISCNNSGKDGNSASTNPADESKGPNLTEISKKITDSNAVVLAVKEVE
TLLASIDELAEKAIGKKIQQNNGLGAEANKNGSLLAGVYSISTLITEKLSA
MKDSGGLKAEIEKAKDCSEKFTKKLETSHAELGKNEATDDDAKKAILRTNG
DKTKGAEELQKLFESVGGLAKAAKEMLTNSVKELTSPVVAETPKKPGSVDK
L.

P23 *B. mayonii*

SEQ ID NO: 5

MFLFISCNNSGKDGNASNSADESAKGPNLTEISKKITDSNAVVLAVKEVEA
LVASIDELAKAIGKKIQQNNGLGNEAGKNGSLLSGIYTISTVITQKLGALN
NEELKERIKEAKECSEAFTKKLETNHTDLGKHDASDDDAKKAILRTNGDKT
KGAEELEKLFKAVESLSTEAKGMLTNSVKQLTSPVVAETPKKP.

P23 *B. garinii*

SEQ ID NO: 6

MFLFISCNNSGGDTASTNPDESVKGPNLTEISKKITDSNAFVLAVKEVEAL
ISSIDELAKAIGQRIQQNGLVADAGHNSALLAGAHEISILITQKLDGLKGL
EGLKAEIAEAKKYSEAFTKKLKDNHAQLGIQNGASLDDEAKKAILKTNVDK
TKGAEELEKLFKSVESLSKAAQEALTNSVKELTNPVVAETPKKP.

P23 *B. afzelii*

SEQ ID NO: 7

MFLFISCNNSGKGGDIASTNPDESAKGPNLTEISKKITDSNAVVLAVKEVE
ALLSSIDELAKTIGKKIEANGLGNEADKNGSLLAGAYAISTLIKQKLDGLK
GLEGLNKEIAEAKKCSEAFTKKLQDSNADLGKHNATDADSKEAILKTNGTK
TKGAKELEELFKSVESLSKAAKEALSNSVKELTSPVVAESPKNPGSVDKL.

P23 *B. spielmanii*

SEQ ID NO: 8

MFLFISCNNSGGDSTSTKPVDEPAKGPNLAEISKKITDSNTFVLAVKEVET
LVSSIDELAKKAIGQKIDQNSGLGALQNQNGSLLAGVYAISTLITDKLSKL
KNSEELKAEIAKAKKCSEDFTNKLKLSHADLGAVNGATTDDHAKAAILKTN
APDDKGAKEFKGLFESVESLSKAAKAALANSVKELTSPVAAEAPKKPGSVD
KL.

P23 *B. valaisiana*

SEQ ID NO: 9

MGDTASTNPVDESAKGPNLTEISKKITDSNAIVLAVKEVETLLASINEIAN
KGIGKKINQNGLDNLTDHNGSLIAGAYVISTLITEKLNNLKNSEGLKEKIK
KVKECSDKFTKKLTTSNGDLGKENVTDAHAQAAILKTNPTNDKGAKELGEL
FESVEILSKAAQEALTNSIAELTSPVVAENPKNP.

-continued

P23 *B. bavariensis*

SEQ ID NO: 10

MFLFISCNNSGGDSASTNPDESAKGPNLTVISKKITDSNAFLLAVKEVEAL

LSSIDELSKAIGKKIKNDGTLDNEANRNESLIAGAYEISKLITQKLSVLNS

EELKEKIKEAKDCSEKFTTKLKDSHAELGIQSVQDDNAKKAILKTHGTKDK

GAKELEELFKSLESLSKAAQAALTNSVKELTNPVVAETPKKP.

P31 *B. burgdorferi* B31

SEQ ID NO: 11

MAKQNVSSLDEKNSVSVDLPGEMKVLVSKEKNKDGKYDLIATVDKLELKGT

SDKNNGSGVLEGVKADKSKVKLTISDDLGQTTLEVFKEDGKTLVSKKVTSK

DKSSTEEKFNEKGEVSEKIITRADGTRLEYTGIKSDGSGKAKEVEKGYVLE

GTLTAEKTTLVVKEGTVTLSKNISKSGEVSVELNDTDSSAATKKTAAWNSG

TSTLTITVNSKKTKDLVFTKENTITVQQYDSNGTKLEGSAVEITKLDEIKN

ALK.

P31 *B. burgdorferi* 297

SEQ ID NO: 12

MAKQNVSSLDEKNSVSVDLPGEMNVLVSKEKNKDGKYDLIATVDKLELKGT

SDKNNGSGVLEGVKADKSKVKLTISDDLGQTTLEVFKEDGKTLVSKKVTSK

DKSSTEEKFNEKGEVSEKIITRADGTRLEYTEIKSDGSGKAKEVLKGYVLE

GTLTAEKTTLVVKEGTVTLSKNISKSGEVSVELNDTDSSAATKKTAAWNSG

TSTLTITVNSKKTKDLVFTKENTITVQQYDSNGTKLEGSAV.

P31 *B. bissettii*

SEQ ID NO: 13

MKQNVSGLDEKNSVSVDLPGEMKVLVSKEKDKDGKYSLMATVDKLELKGTS

DKNNGSGILEGVKADKSKVKLTVSEDLSTTTLEVLKEDGKTLVSKKTTSKD

KSSTEEKFNDKGELAEKTIVRANGTRLEYTEVKSDGSGKAKETLKDYALEG

TLTAEKATLVVKEGTVTLSKHISKSCEVTAELNDTDSAQATKKTGKWDAGT

STLTISVNSKKTKNLVFTKQDTITVQKYDSAGTNLEGTAVEIKTLDELKNA

LK.

P31 *B. californiensis*

SEQ ID NO: 14

MAKQNVSSLDEKNSVSVDLPGEMKVLVSKEKDKDGKYSLMATVDKLELKGT

SDKNNGSGVLEGVKDDKSKVKLTVSDDLSTTTLEVLKEDGKTLVSRKETSK

DKSSTEEKFNEKGELTEKMERSNGTRLEYTEIKTDGSGKAKETLKDFVLEG

TLTTEKAILTVKEGTVTLNKNISKSGEVTVDLNDTSTTAATKKTGKWDSST

STLTVSVNSKKTKDLVFTKQDTITVQKYDSAGTNLEGTAVEIKTLDEIKNA

LK.

P31 *B. mayonii*

SEQ ID NO: 15

MAKQNVSSLDEKNSVSVDLPGEIKVLVSKEKDKDGKYSLMATVDKLELKGT

SDKNNGSGVLEGVKADKSKVKLTVSDDLSKTTLEVLKEDGKTLVSRKVTSK

DKSSTEEKFNEKGELAEKTMTRADETRLEYTEIKSDGSGKAKEVLKGYALE

GTLTAEKTTLVVKEGTVTLSKNISKSGEVTAELNDTDSAAATKKTGAWNSG

TSTLTITANSKKTKDLVFTKENTITVQKYDTAGIKLEGSAVEIKTLDELKN

ALK.

-continued

P31 *B. garinii*

SEQ ID NO: 16

MKQNVSSLDEKNSVSVDLPGGMQVLVSKEKDKDGKYSLMATVDKLELKGTS

DKNNGSGTLEGEKTDKSKAKLTIAEDLSKTTFEIFKEDGKTLVSKKVTLKD

KSSTEEKFNAKGEASEKTIVRANGTRILEYTDIKSDKTGKAKEVLKDFALE

GTLAADGKTTLKVTEGTVVLSKHISNSGEITVELNDSDTTQATKKTGTWDS

KTSTLTISVNSRKTKNLVFTKEDTITVQKYDSAGTNLEGKAVEITTLKELK

DALK.

P31 *B. afzelii*

SEQ ID NO: 17

MAKQNVSSLDEKNSASVDLPGEMKVLVSKEKDKDGKYSLKATVDKIELKGT

SDKDNGSGVLEGTKDDKSKAKLTIADDLSKTTFELFKEDGKTLVSRKVSSK

DKTSTDEMFNEKGELSAKTMTRENGTKLEYTEMKSDGTGKAKEVLKNFTLE

GKVANDKVTLEVKEGTVTLSKEIAKSGEVTVALNDTNTTQATKKTGAWDSK

TSTLTISVNSKKTTQLVFTKQDTITVQKYDSAGTNLEGTAVEIKTLDELKN

ALK.

P31 *B. spielmanii*

SEQ ID NO: 18

MAKQNVSGLDEKNSTSVDVPGELKVLVSKEKDKDGKYSLMATVDKLELKGT

SDKNDGSGVLEGVKADKSKVKLTISDHLSKTTFEVFKEDGKTLVSRNVNSK

DKSSTKEKFNEKGELSEKTLVRANGTKLEYTEIKSDGTGKAKEVLKDFTLE

GTLANEKATLTVKEGTVTLSKNIDKSGEVTVALNDTDSTAATKKTGAWDSK

TSTLTITVNSKKTKDLVFTKQDTITVQKYDSAGTNLEGSAVEIKTLDELKN

ALK.

P31 *B. valaisiana*

SEQ ID NO: 19

MAKQNVSSLDEKNSASVDLPGEMKVLVSKEKDKDGKYSLVATVDKVELKGT

SDKNNGSGTLEGVKDDKSKVKLTISDDLGETKLETFKEDGTLVSRKVNFKD

KSFTEEKFNEKGEVSEKILTRSNGTTLEYSQMTDAENATKAVETLKNGIKL

PGNLVGGKTTLKITEGTVTLSKHIAKSGEVTVEINDTSSTPNTKKTGKWDA

RNSTLTIIVDSKNKTKLVFTKQDTITVQSYNPAGNKLEGTAVEIKTLQELK

NALK.

P31 *B. bavariensis*

SEQ ID NO: 20

MKQNVSSLDEKNSVSVDLPGEMKVLVSKEKDKDGKYSLMATVDKLELKGTS

DKSNGSGTLEGEKSDKSKAKLTISEDLSKTTFEIFKEDGKTLVSKKVNSKD

KSSIEEKFNAKGELSEKTILRANGTRLEYTEIKSDGTGKAKEVLKDFALEG

TLAADKTTLKVTEGTVVLSKHIPNSGEITVELNDSNSTQATKKTGKWDSNT

STLTISVNSKKTKNIVFTKEDTITVQKYDSAGTNLEGNAVEIKTLDELKNA

LK.

P39 *B. burgdorferi* B31

SEQ ID NO: 21

MKGSLGSEIPKVSLIIDGTFDDKSFNESALNGVKKVKEEFKIELVLKESSS

NSYLSDLEGLKDAGSDLIWLIGYRFSDVAKVAALQNPDMKYAIIDPIYSND

PIPANLVGMTFRAQEGAFLTGYIAAKLSKTGKIGFLGGIEGEIVDAFRYGY

EAGAKYANKDIKISTQYIGSFADLEAGRSVATRMYSDEIDIIHHAASLGGI

GAIEVPKELGSGHYIIGVDEDQAYLAPDNVITSTTKDVGRALNIFTSNHLK

-continued

TNTFEGGKLINYGLKEGVVGFVRNPKMISFELEKEIDNLSSKIINKEIIVP
SNKESYEKFLKEFI.

P39 *B. burgdorferi* 297

SEQ ID NO: 22

MKGSLGSEIPKVSLIIDGTFDDKSFNESALNGVKKVKEEFKIELVLKESSS
NSYLSDLEGLKDAGSDLIWLIGYRFSDVAKVAALQNPDMKYAIIDPIYSND
PIPANLVGMTFRAQEGAFLTGYIAAKLSKTGKIGFLGGIEGEIVDAFRYGY
EAGAKYANKDIKISTQYIGSFADLEAGRSVATRMYSDEIDIIHHAASLGGI
GAIEVPKELGSGHYIIGVDEDQAYLAPDNVITSTTKDVGRALNIFTSNHLK
TNTSEGGKLINYGLKEGVVGFVRNPKMISFELEKEIDNLSSKIINKEIIVP
SNKESYEKFLKEFI.

P39 *B. garinii*

SEQ ID NO: 23

MKGSLESEIPKVSLIIDGTFDDKSFNESALNGIKKVKEEFKIEPVLKESSI
NSYLSDLEGLKDTGSNLIWLIGYKFSDVAKAVSLQNPEIKYAIIDPIYSDE
PIPANLVGMTFRSQEGAFLTGYIAAKVSKTGKIGFLGGIEGEIVDSFRYGY
EAGAKYANKDIKISAYYIGSFADLEAGRSVATKMYSDGIDIIHHAAGLGGI
GAIEVAKELGSGHYIIGVDEDQSYLAPNNIITSATKDVGRSLNIFTSNYLK
TNTFEGGRLINYGLKEGVVGFVKNPKMIPFELEKEIDNLSSKIINKEIIVP
YNKESYEKFLKE.

P39 *B. afzelii*

SEQ ID NO: 24

MKSGLESGIPKVSLVIDGTFDDKSFNESALNGVKKLKEEFEIELVLKESST
NSYLSDLEGLKDAGSNLIWLIGYKFSDVAKAVSLQNSEMKYAIIDPVYSNE
PIPANLVGMTFRAQEGAFLTGYIAAKVSKTGKIGFLGGIEGDIVDAFRYGY
EAGAKYANKDIKIFSQYIGSFSDLEAGRSVATKMYSDGIDIIHHAAGLGGI
GAIEVAKELGSGHYIIGVDEDQSYLAPNNVITSTTKDVGRSLNLFTSNYLK
TNTFEGGKLINYGLKEGVVGFVRNPKMIPFEVEKEIDSLSSKIINKEVIVP
YNKESYEKFLKEFI.

P39 *B. spielmanii*

SEQ ID NO: 25

MKGGLENKIPKVSLIIDGTFDDKSFNESALNGVKKLKEEFEIDLVLKESST
NSYVSDLEGLKDAGSNLIWLIGYKFSDVAKAVSLQNSEMKYAIIDPVYSSE
PIPANLVGMTFRAQEGAFLTGYIASKVSKTGKIGFLGGIEGDIVDAFRYGY
EAGAKYANKDIKIFSQYIGSFADIEAGRSVATKMYSDGIDIIHHAAGLGGI
GAIEVAKELGSGHYIIGVDEDQSYLAPNNVITSSTKDVGRSLNLFTSNYLK
TNNFEGGKLINYGLKEGVVGFVRNPKMIPFEVEKEIDSLSGKIINKEVIVP
YNKESYEKFLKEFL.

P39 *B. valaisiana*

SEQ ID NO: 26

MKGSLEGGIPKVSVIIDGTFDDKSFNESALNGIKKVKEEFKVEFVLKESSS
NSYLSDLEGLKDTGSNLIWLIGYRFSDVAKVVSLQNSEVKYAIIDPVYSNE
PIPANLVGMTFRAQEGAFLTGYIASKVSKTGKIGFLGGIKSEIVDAFRYGY
EAGAKYANKDIKIFTHYIGSFADLEASRSIAIKMYSDGIDIIHHAAGLGGI
GAIEVAKELGSGHYIIGVDEDQSYLAPDNVITSSTKDVGRALNIFTSNYLK

-continued

TNTFEGGKLINYGLKEGVVGFVRNPKMIPFELEKEIDSISSKIINKEVIVP
YNKGSYEKFLKEFI.

P93 *B. burgdorferi* B31

SEQ ID NO: 27

MFLNGFPLNARKVDKEKLKDFVNMDLEFVNYKGPYDSTNTYEQIVGIGEFL
ARPLTNSNSNSSYYGKYFINRFIDDQDKKASVDVFSISSKSELDSILNLRR
ILTGYIIKSFDYDRSSAELIAKVITIYNAVYRGDLDYYKGFYIEPALKSLT
KENAGLSRVYSQWAGKTQIFIPLKKDILSGNIESDIDIDSLVTDKVIAALL
SENEAGVNFARDITDIQGETHKADQDKIDTELDNIHESDSNITETIENLRD
QLEKATDEEHKKEIESQVDAKKKEKEELDKKAINLDKAQQKLDSAEDNLDV
QRDTVREKIQEDINEINKEKNLPKPGDVSSPKVDKQLQIKESLEDLQEQLK
EAGDENQKREIEKQIEIKKRDEELLKSKDGKVSKDYEALDLDRELSKASSK
EKSKVKEEEITKGKSRASLGDLNNDKNLMLPEDQKLPEDKKLDSKLDGKKE
FKPVSEVEKLDKISKSNNNEVGKLSPLDKPSYDDIDSKEEVDNKAINLQKI
DPKVKDQTTSLNEDLDKDLTTMSIDSSSPVFLEVIDPITNLGTLQLIDLNT
GVRLKESTQQGIQRYGIYEREKDLVVIKMDSGKAKLQILNKLENLKVVSES
NFEINKNSSLYVDSKMILAAVRDKDDSNAWRLAKFSPKNLDEFILSENKIL
PFTSFSVRKNFIYLQDELKNLVILDVNTLKKVK.

P93 *B. burgdorferi* 297

SEQ ID NO: 28

MFLNGFPVSAREVDREKLKDFVNMDLEFVNYKGPYDSTNTYEQIVGIGEFL
ARPLTNSNSNSSYYGKYFINRFIDDQDKKASVDVFSIGSKSELDSILNLRR
ILTGYLIKSFDYDRSSAELIAKVITIYNAVYRGDLDYYKGFYIEAALKSLS
KENAGLSRVYSQWAGKTQIFIPLKKDILSGNIESDIDIDSLVTDKVVAALL
SENEAGVNFARDITDIQGETHKADQDKIDIELDNIHESDSNITETIENLRD
QLEKATDEEHKKEIESQVDAKKKQKEELDKKAINLDKAQQKLDSAEDNLDV
QRNTVREKIQEDINEINKEKNLPKPGDVSSPKVDKQLQIKESLEDLQEQLK
ETGDENQKREIEKQIEIKKSDEKLLKSKDDKASKDGKALDLDRELNSKASS
KEKSKAKEEEITKGKSQKSLGDLNNDENLMMPEDQKLPEVKKLDSKKEFKP
VSEVDKLDKISKSNNNVGELSPLDKSSYKDIDSKEETVNKDVNLQKTKPQV
KDQVTSLNEDLTTMSIDSSSPVFLEVIDPITNLGTLQLIDLNTGVRLKEST
QQGIQRYGIYEREKDLVVIKMDSGKAKLQILDKLKNLKVVSESNFEINKNS
SLYVDSKMILVAIRDKDSSNDWRLAKFSPKNLDEFILSENKIMPFTSFSVR
KNFIYLQDEFKSLVILDVNTLKKVK.

P66 *B. burgdorferi* B31

SEQ ID NO: 29

MKEKDIFKINPWMPTFGFENTSEFRLDMDELVPGFENKSKITIKLKPFEAN
PELGKDDPFSAYIKVEDLALKAEGKKGDQFKIDVGDITAQINMYDFFIKIS
TMTDFDFNKESLFSFAPMTGFKSTYYGFPSNDRAVRGTILARGTSKNIGTI
QLGYKLPKLDLTFAIGGTGTGNRNQENDKDTPYNKTYQGILYGIQATWKPI
KNLLDQNEDTKSVIAETPFELNFGLSGAYGNETFNNSSITYSLKDKSVVGN
DLLSPTLSNSAILASFGAKYKLGLTKINDKNTYTLILQMGTDFGIDPFASD
FSIFGHISKAANFKKETPSDPNKKAEIFDPNGNALNFSKNTELGIAFSTGA
SIGFAWNKDTGEKESWAIKGSDSYSTRLFGEQDKKSGVALGISYGQNLYRS

-continued

KDTEKRLKTISENAFQSLNVEISSYEDNKKGIINGLGWITSIGLYDILRQK

SVENYPTTISSTTENNQTEQSSTSTKTTTPNLTFEDAMKLGLALYLDYAIP

IASISTEAYVVPYIGAYILGPSNKLSSDATKIYLKTGLSLEKLIRFTTISL

GWDSNNIIELANKNTNNAAIGSAFLQFKIAYSGS.

P58 *B. burgdorferi* B31

SEQ ID NO: 30

MKERKEGVSFKISLGAEPSSLDPQLAEDNVASKMIDTMFRGIVTGDPNTGG

NKPGLAKGWDISSDGTVYTFNLREKITWSDGVAITAEGIRKSYLRILNKET

GSKYVEMVKSVIKNGQKYFDGQVTDSELGIRAIDEKTLEITLESPKPYFID

MLVHQSFIPVPVHVTEKYGQNWTSPENMVTSGPFKLKERIPNEKYVFEKNN

KYYDSNEVELEEITFYTTNDSSTAYKMYENEELDAIFGSIPPDLIKNLKLR

SDYYSSAVNAIYFYAFNTHIKPLDNVKIRKALTLAIDRETLTYKVLDNGTT

PTRRATPNFSSYSYAKSLELFNPEIAKTLLAEAGYPNGNGFPILKLKYNTN

EANKKICEFIQNQWKKNLNIDVELENEEWTTYLNTKANGNYEIARAGWIGD

YADPLTFLSIFTQGYTQFSSHNYSNPEYNELIKKSDLELDPIKRQDILRQA

EEIIIEKDFPIAPIYIYGNSYLFRNDKWTGWNTNILERFDLSQLKLKNK.

P45 *B. burgdorferi* B31

SEQ ID NO: 31

MRYEMKEESPGLFDKGNSILETSEESIKKPMNKKGKGKIARKKGKSKVSRK

EPYIHSLKRDSANKSNFLQKNVILEEESLKTELLKEQSETRKEKIQKQQDE

YKGMTQGSLNSLSGESGELEEPIESNEIDLTIDSDLRPKSSLQGIAGSNSI

SYTDEIEEEDYDQYYLDEYDEEDEEEIRLSNRYQSYLEGVKYNVDSAIQTI

TKIYNTYTLFSTKLTQMYSTRLDNFAKAKAKEEAAKFTKEDLEKNFKTLLN

YIQVSVKTAANFVYINDTHAKRKLENIEAEIKTLIAKIKEQSNLYEAYKAI

VTSILLMRDSLKEVQGIIDKNGVWY.

P41 *B. burgdorferi* B31

SEQ ID NO: 32

MRNNGINAANLSKTQEKLSSGYRINRASDDAAGMGVSGKINAQIRGLSQAS

RNTSKAINFIQTTEGNLNEVEKVLVRMKELAVQSGNGTYSDADRGSIQIEI

EQLTDEINRIADQAQYNQMHMLSNKSASQNVRTAEELGMQPAKINTPASLS

GSQASWTLRVHVGANQDEAIAVNIYAANVANLFSGEGAQTAQAAPVQEGVQ

QEGAQQPAPATAPSQGGVNSPVNVTTTVDANTSLAKIENAIRMISDQRANL

GAFQNRLESIKNSTEYAIENLKASYAQIKDATMTDEVVAATTNSILTQSAM

AMIAQANQVPQYVLSLLR.

P41 *B. mayonii*

SEQ ID NO: 33

MRNNGINAANLSKTQEKLSSGYRINRASDDAAGMGVSGKINAQIRGLSQAS

RNTSKAINFIQTTEGNLNEVEKVLVRMKELAVQSGNGTYSDADRGSIQIEI

EQLTDEINRIADQAQYNQMHMLSNKSASQNVRTAEELGMQPAKINTPSSLS

GSQASWTLRVHVGANQDEAIAVNIYAANVANLFSGEGTQTAQVAPVQEGAQ

QEGAQQPAPATAPSQGGVNSPVNVTTTVDANTSLAKIENAIRMISDQRANL

GAFQNRLESIKNSTEYAIENLKASYAQIKDATMTDEVVAATTNSILTQSAM

AMIAQANQVPQYVLSLLR.

-continued

P34 *B. burgdorferi* B31

SEQ ID NO: 34

MGSCAQKGAESIGSQKENDLNLEDSSKKSHQNAKQDLPAVTEDSVSLFNGN

KIFVSKEKNSSGKYDLRATIDQVELKGTSDKNNGSGTLEGSKPDKSKVKLT

VSADLNTVTLEAFDASNQKISSKVTKKQGSITEETLKANKLDSKKLTRSNG

TTLEYSQITDADNATKAVETLKNSIKLEGSLVGGKTTVEIKEGTVTLKREI

EKDGKVKVFLNDTAGSNKKTGKWEDSTSTLTISADSKKTKDLVFLTDGTIT

VQQYNTAGTSLEGSASEIKNLSELKNALK.

P34 *B. burgdorferi* 297

SEQ ID NO: 35

MRLLIGFALALALIGCAQKGAESIGSQKENDLNLEDSSKKSHQNAKQDLPA

VTEDSVSLFNGNKIFVSKEKNSSGKYDLRATIDQVELKGTSDKNNGSGTLE

GSKPDKSKVKLTVSADLNTVTLEAFDASNQKISSKVTKKQGSITEETLKAN

KLDSKKLTRSNGTTLEYSQITDADNATKAVETLKNSIKLEGSLVGGKTTVE

IKEGTVTLKREIEKDGKVKVTLNDTAGSNKKTGKWEDSTSTLTISADSTKT

KDLVFLTDGTITVQQYNTAGTSLEGSASEIKNLSELKNALK.

P34 *B. valaisiana*

SEQ ID NO: 36

MRQYLIGFALVLALLACAQKGAEPKTQNSDREIMDSNKDSSKDSKQVLTTS

TEKAVSLFNGYTIFVSKEKNTSGKYDLRAVVDQFELKGTSDKDNGSGTLKG

SKADKTKMTISITEDLNSVTVETFDSGNKKVSSKVVKKHGLLTEENFKADK

LDSQKLTRSNGTTLEYSQMTDAENATKAVETLKNGIKLEGNLVGGKTTLKI

TVGTVTLTREIEKDGRIKLFLNDTDSSPTKKTAKWEDSTNTLTITSNRKKT

KDLVFLIDGTITVQNYNSAGKLDGQASEIKSLGELQGALK.

P34 *B. spielmanii*

SEQ ID NO: 37

MRQQYLLVFALILALIACSQKGTEPKDDNYNDQEIASGDKEPKISKKELPR

ETETAVSLFNGNEIFISKEKNSAGKYDLRARVDLVELKGTSDKNTGAGKLE

GLKADKSKVTMTISDDLNTVTVETYDASNKKTGSEVVKKQGSVIKESYKAN

KLDSKKLTRSNDTTLEYSQMTDEENATKAVETLKNGIKFEGNLVGGKTTVK

ITEGTVTLKREIDKDGKIKVFLDDTATDNTKKTGKWNENNNTLTVTVDSKK

TKDLVFSDDGTSTITVQKYNTAGTNLEGNPSEIKDLAALKGALK.

P34 *B. garinii*

SEQ ID NO: 38

MKKYLLGFALVLALIACGQKGAEPKHNDQEVEDSKKDQKDASKKDLPLVTE

DTVKLFNDTEIFISKEKNNAGKYELRAMVDTVELKGFSEKNTGAGNLEGLK

ADKSKVTMLVSDDLNTITIETYNTSNKKVSSQVVKKQGLLTEESYKADKLD

SKKLTRTNGTTLEYSDMTDAANATKAVETLKNGIEFEGNLVGGKTTLNIKE

GTVTLTREIDKDDKLKIYLNDTASSSKKTASWNDTDTLTISAEGKKTKDLV

FRTDGTITVQNYDSASGTKLEGTATEIKDLEALKAALK.

P34 B. afzelii

SEQ ID NO: 39

MKQYLLVFALVLALIACSQKGTEPKSTSQDHNDQEIINSDNTPKDSKKDLT

VLAEENSVPLFNGNKIFVSKEKNSAGKYELRATVDTVELKGVSDKNNGSGK

LEGTKADKTKVAMTIADDLNTITVETYDASNKKTGSEVVKKQGSVIKESYK

-continued

ANKLDSKKITRENETTLEYSEMTDSSNATKAVETLKNGIKLEGSLVGGKTT VKLTEGTITLTREIEQDGKVKIYLNDTTSGSTKKTATWNETTNTLTISADS KKTKDFVFLTDGTITVQAYDTAGTKLEGNSSEIKDLAALKAALK.

P30 *B. burgdorferi* B31

SEQ ID NO: 40

MFLLLSISCVHDKQELSSKSNLNNQKGYLDNEGANSNYESKKQSILSELNQ LLKQTTNSLKEAKNTTDNLNASNEANKVVEAVINAVNLISSAADQVKSATK NMHDLAQMAEIDLEKIKNSSDKAIFASNLAKEAYSLTKAAEQNMQKLYKEQ QKISESESESDYSDSAEIKQAKEAVEIAWKATVEAKDKLIDVENTVKETLD KIKTETTNNTKLADIKEAAELVLQIAKNAKEIVQEVVALLNT.

P28 *B. burgdorferi* B31

SEQ ID NO: 41

MTSKDLEGAVKDLESSEQNVKKTEQEIKKQVEGFLEILETKDLNTLDTKEI EKQIQELKNKIEKLDSKKTSIETYSGYEEKINKIKEKLNGKGLEDKLNELS ESLKKRKEERKKALQEAKKKFEEYKNQAESATGVTHGSQVQRQGGVGLQAW QCANSLGFKNMTSGNNTSDMTNEVITNSLKKIEEELKNIGETVEGKKE.

P28 *B. burgdorferi* 297

SEQ ID NO: 42

MTSKDLEGVVQDLESSEQNVKKTEQEIKKQVEGFLEILETKDLNTLDTKEI EKQIQELKDTINKLEAKKTSLKTYSEYEEKLKQIKEKLKDKKELEDKLKGL EDSLKKKKEDRKKALEDAKKKFEEFKGQVGSATGVTTGHRAGNQGSIGAQA WQCANSLGLGVSYSSSTGTDSNELANKVIDDSIKKIDEELKNTIENNGKVK KE.

P18 *B. burgdorferi* B31

SEQ ID NO: 43

MKIRLERSAKDITDEIDAIKKDAALKGVNFDAFKDKKTGSGVSENPFELEA KVRATTVAEKFVIAIEEEATKLKETGSSGEFSAMYDLMFEVSKPLQKLGIQ EMTKTVSDAAEENPPTTAQGVLEIAKKMREKLQRVHTKNYCTLKKKENSTF TDEKCKNN.

VlsE *B. burgdorferi* B31

SEQ ID NO: 44

MDPKKSDVKTYFTTVAAKLEKTKTDLNSLPKEKSDISSTTGKPDSTGSVGT AVEGAIKEVSELLDKLVKAVKTAEGASSGTAAIGEVVADADAAKVADKASV KGIAKGIKEIVEAAGGSEKLKAVAAAKGENNKGAGKLFGKAGAAAHGDSEA ASKAAGAVSAVSGEQILSAIVTAADAAEQDGKKPEEAKNPIAAAIGDKDGG AEFGQDEMKKDDQIAAAIALRGMAKDGKFAVKDGEKEKAEGAIKGAAESAV RKVLGAITGLIGDAVSSGLRKVGDSVKAASKETPPALNK.

C6 chimera

SEQ ID NO: 45

MKKDDQIAAAIALRGMAKDGKFAVKDGGGMKKNDQIAAAIVLRGMAKDGEF ALKNELGSMKKNDQIAAAMVLRGMAKDGQFALTGGGGMKKDDQIAAAIALR GMAKDGKFAVKDGGGMKKDAQIAAAIVLRGMAKDGKFAVKK.

PepC10 chimera

SEQ ID NO: 46

MPVVAESPKKPGSPVVAETPKKPGSPVVAESPKKPGSPIVAESPKNPGSPV VAESPKKPGSPVAAESPKKPGSPVVAESPKKPGSPWAETPKKPGSPVVAES PKKPGSW.

-continued

P23 *B. spielmanii*

SEQ ID NO: 47

MKKNTLSAILMTLFLFISCNNSGGDSTSTKPVDESAKGPNLTEISKKITDS NTFVLAVKEVETLLLSIDELAKAIGKKIENNGLGTEASHNTSLLAGAYTIS SLITQKLNALKNSGELKAEIEKAKNCSEAFTKKLKEKHQDLGTAGGNATDD HAKAAILKTNATDDKGAKELKELFESVESLSKAAKAALANSVKELTSPVVA ETPKKP.

P23 *B. bissettii*

SEQ ID NO: 48

MKKNTLSAILMTLFLFISCNNSGKDGNSASTNPADESAKGPNLTEISKKIF DSNAIVLAVKEVETLLLSIDELAKAIGKKINNNGLDVLQNFNASLLGGAHT ISKLITEKLSKLNGSEELKEKIEAAKKCSDDFTKKLQSSHAELGVAGGATT DENAKKAILKSNADKTKGADELGKLFESVESLAKAAKEMLANSVKELTSPV VAETPKKP.

P23 *B. valaisiana*

SEQ ID NO: 49

MKKNTLSAILMTLFLFISCNNSGKDVTTSTDSVDESAKGPNLVEISKKITD SNAIVLAVKEVETLLSSIDELANKAIGKKIQQNGSLANEADHNGSLLAGTY AISTLITQKLGKLKISEELKEKIEDAKKCSEDFARKLSDNHNDLGKEGVTD DDAKKAILKTHGTKDKGAAEFEKLFKSVESLVKAAQETLVNSIKELTSPVA AESPKKP.

P23 *B. burgdorferi* B31

SEQ ID NO: 50

MKKNTLSAILMTLFLFISCNNSGKDGNTSANSADESVKGPNLTEISKKITD SNAVLLAVKEVEALLSSIDEIAAKAIGKKIHQNNGLDTENNHNGSLLAGAY AISTLIKQKLDGLKNEGLKEKIDAAKKCSETFTNKLKEKHTDLGKEGVTDA DAKEAILKTNGTKTKGAEELGKLFESVEVLSKAAKEMLANSVKELTSPVVA ESPKKP.

P23 *B. burgdorferi* 297

SEQ ID NO: 51

MKKNTLSAILMTLFLFISCNNSGKDGNTSANSADESVKGPNLTEISKKITE SNAVVLAVKEIETLLASIDELATKAIGKKIQQNGGLAVEAGHNGTLLAGAY TISKLITQKLDGLKNSEKLKEKIENAKKCSEDFTKKLEGEHAQLGIENVTD ENAKKAILITDAAKDKGAAELEKLFKAVENLAKAAKEMLANSVKELTSPIV AESPKNP.

P23 *B. mayonii*

SEQ ID NO: 52

MKKNTLSAILMTLFLFISCNNSGKDGNASNSADESAKGPNLTEISKKITDS NAVVLAVKEVEALVASIDELAKAIGKKIQQNNGLGNEAGKNGSLLSGIYTI STVITQKLGALNNEELKERIKEAKECSEAFTKKLETNHTDLGKHDASDDDA KKAILRTNGDKTKGAEELEKLFKAVESLSTEAKGMLTNSVKQLTSPVVAET PKKP.

P23 *B. garinii*

SEQ ID NO: 53

MKKNTLSAILMTLFLFISCNNSGGDTASTNPDESAKGPDLTVISKKITDSN

AVVLVVKEVEALLSSIDELSKAIGKKIRNDGTLDNEANRNESLIAGAYEIS

KLITQKLSVLNSEELKEKIKEAKDCSEKFTTKLRDSHAELGIQNVQDDNAK

RAILKTHGNKDKGAKELKELSESLEKLSKAAQAALANSVKELTSPVVAESP

KKP.

P23 *B. bavariensis*

SEQ ID NO: 54

MKKNTLSAILMTLFLFISCNNSGGDSASTNPDESAKGPNLTVISKKITDSN

AFLLAVKEVEALLSSIDELSKAIGKKIKNDGTLDNEANRNESLIAGAYEIS

KLITQKLSVLNSEELKEKIKEAKDCSEKFTTKLKDSHAELGIQSVQDDNAK

KAILKTHGTKDKGAKELEELFKSLESLSKAAQAALTNSVKELTNPVVAETP

KKP.

P23 *B. afzelii*

SEQ ID NO: 55

MKKNTLSAILMTLFLFISCNNSGKGGDSTSTNPADESAKGPNLTEISKKIT

DSNAFVLAVKEVETLVASIDELATKAIGKKIKNDGTLDNEANHNGSLLAGA

YAISTLITQKLSVLNSEELKAEIVKAKKCSEDFTKKLKDKHTELGKQDAND

DDAKKAILKTNGDKTLGAAELEKLSESVTSLSKAAKESLTNSVKELTSPVV

AESPKKP.

P23 *B. californiensis*

SEQ ID NO: 56

MKKNTLSAILMTLFLFISCNNSGKDGNSASTNPADESKGPNLTEISKKITD

SNAVVLAVKEVETLLASIDELAEKAIGKKIQQNNGLGAEANKNGSLLAGVY

SISTLITEKLSAMKDSGGLKAEIEKAKDCSEKFTKKLETSHAELGKNEATD

DDAKKAILRTNGDKTKGAEELQKLFESVGGLAKAAKEMLTNSVKELTSPVV

AETPKKP.

P31 *B. bissettii*

SEQ ID NO: 57

MKKYLLGIGLILALIACKQNVSGLDEKNSVSVDLPGEMKVLVSKEKDKDGK

YSLMATVDKLELKGTSDKNNGSGILEGVKADKSKVKLTVSEDLSTTTLEVL

KEDGKTLVSKKTTSKDKSSTEEKFNDKGELAEKTIVRANGTRLEYTEVKSD

GSGKAKETLKDYALEGTLTAEKATLVVKEGTVTLSKHISKSGEVTAELNDT

DSAQATKKTGKWDAGTSTLTISVNSKKTKNLVFTKQDTITVQKYDSAGTNL

EGTAVEIKTLDELKNALK.

P31 *B. mayonii*

SEQ ID NO: 58

MKKYLLGIGLILALIACKQNVSSLDEKNSVSVDLPGEIKVLVSKEKDKDGK

YSLMATVDKLELKGTSDKNNGSGVLEGVKADKSKVKLTVSDDLSKTTLEVL

KEDGKTLVSRKVTSKDKSSTEEKFNEKGELAEKTMTRADETRLEYTEIKSD

GSGKAKEVLKGYALEGTLTAEKTTLVVKEGTVTLSKNISKSGEVTAELNDT

DSAAATKKTGAWNSGTSTLTITANSKKTKDLVFTKENTITVQKYDTAGIKL

EGSAVEIKTLDELKNALK.

P31 *B. burgdorferi* B31

SEQ ID NO: 59

MKKYLLGIGLILALIACKQNVSSLDEKNSVSVDLPGEMKVLVSKEKNKDGK

YDLIATVDKLELKGTSDKNNGSGVLEGVKADKSKVKLTISDDLGQTTLEVF

KEDGKTLVSKKVTSKDKSSTEEKFNEKGEVSEKIITRADGTRLEYTGIKSD

GSGKAKEVLKGYVLEGTLTAEKTTLVVKEGTVTLSKNISKSGEVSYELNDT

DSSAATKKTAAWNSGTSTLTITVNSKKTKDLVFTKENTITVQQYDSNGTKL

EGSAVEITKLDEIKNALK.

P31 *B. burgdorferi* 297

SEQ ID NO: 60

MKKYLLGIGLILALIACKQNVSSLDEKNSVSVDLPGEMNVLVSKEKNKDGK

YDLIATVDKLELKGTSDKNNGSGVLEGVKADKSKVKLTISDDLGQTTLEVF

KEDGKTLVSKKVTSKDKSSTEEKFNEKGEVSEKIITRADGTRLEYTEIKSD

GSGKAKEVLKGYVLEGTLTAEKTTLVVKEGTVTLSKNISKSGEVSVELNDT

DSSAATKKTAAWNSGTSTLTITVNSKKTKDLVFTKENTITVQQYDSNGTKL

EGSAVEITKLDEIKNALK.

P31 *B. californiensis*

SEQ ID NO: 61

MKKYLLGIGLILALIAKQNVSSLDEKNSVSVDLPGEMKVLVSKEKDKDGKY

SLMATVDKLELKGTSDKNNGSGVLEGVKDDKSKVKLTVSDDLSTTTLEVLK

EDGKTLVSRKETSKDKSSTEEKFNEKGELTEKIMERSNGTRLEYTEIKTDG

SGKAKETLKDFVLEGTLTTEKAILTVKEGTVTLNKNISKSGEVTVDLNDTS

TTAATKKTGKWDSSTSTLTVSVNSKKTKDLVFTKQDTITVQKYDSAGTNLE

GTAVEIKTLDEIKNALK.

P31 *B. spielmanii*

SEQ ID NO: 62

MKKYLLGIGLILALIACKQNVSGLDEKNSTSVDVPGELKVLVSKEKDKDGK

YSLMATVDKLELKGTSDKNDGSGVLEGVKADKSKVKLTISDHLSKTTFEVF

KEDGKTLVSRNVNSKDKSSTKEKFNEKGELSEKTLVRANGTKLEYTEIKSD

GTGKAKEVLKDFTLEGTLANEKATLTVKEGTVTLSKNIDKSGEVTVALNDT

DSTAATKKTGAWDSKTSTLTITVNSKKTKDLVFTKQDTITVQKYDSAGTTL

EGSAVEIKTLDELKNALK.

P31 *B. valaisiana*

SEQ ID NO: 63

MKKYLLGIGLILALIACAKQNVSSLDEKNSASVDLPGEMKVLVSKEKDKDG

KYSLMATVDKVELKGTSDKNNGSGTLEGVKDDKSKVKLTISDDLNKTTFET

FKEDGKTLVSRKVNSKDKSSTVEKFNEKGELSEKTITRENGTRLEYTEIKS

DGTGKAKEVLKDFTLEGTLAADKTTLEVKEGTVTLSKHIPNSGEVTVEIND

TSTTQATKKTGKWDAKTSTLTIAVNNKNTKSLVFTKEDTITVQNYDSAGTN

LEGTAVEIKTLDELKNALK.

P31 *B. afzelii*

SEQ ID NO: 64

MKKYLLGIGLILALIACKQNVSSLDEKNSASVDLPGEMKVLVSKEKDKDGK

YSLKATVDKIELKGTSDKDNGSGVLEGTKDDKSKAKLTIADDLSKTTFELF

KEDAKTLVSRKVSSKDKTSTDEMFNEKGELSAKTMTRENGTKLEYTEMKSD

GTGKAKEVLKNFTLEGKVANDKVTLEVKEGTVTLSKEIAKSGEVTVALNDT

NTTQATKKTGAWDSKTSTLTISVNSKKTTQLVFTKQDTITVQKYDSAGTNL

EGTAVEIKTLDELKNALK.

-continued

P31 *B. garinii*

SEQ ID NO: 65

MKKYLLGIGLILALIACKQNVSSLDEKNSVSVDLPGGMTVLVSKEKDKDGK

YSLEATVDKLELKGTSDKNNGSGTLEGEKTDKSKVKLTIADDLSQTKFEIF

KEDGKTLVSKKVTLKDKSSTEEKFNEKGETSEKTIVRANGTRLEYTDIKSD

GSGKAKEVLKDFTLEGTLAADGKTTLKVTEGTVVLSKNILKSGEITVALDD

SDTTQATKKTGKWDSKTSTLTISVNSQKTKNLVFTKEDTITVQKYDSAGTN

LEGKAVEITTLKELKDALK.

P31 *B. bavariensis*

SEQ ID NO: 66

MKKYLLGIGLILALIACKQNVSSLDEKNSVSVDLPGEMKVLVSKEKDKDGK

YSLMATVDKLELKGTSDKSNGSGTLEGEKSDKSKAKLTISEDLSKTTFEIF

KEDGKTLVSKKVNSKDKSSIEEKFNAKGELSEKTILRANGTRLEYTEIKSD

GTGKAKEVLKDFALEGTLAADKTTLKVTEGTVVLSKHIPNSGEITVELNDS

NSTQATKKTGKWDSNTSTLTISVNSKKTKNIVFTKEDTITVQKYDSAGTNL

EGNAVEIKTLDELKNALK.

P39 *B. burgdorferi* B31

SEQ ID NO: 67

MNKILLLILLESIVFLSCSGKGSLGSEIPKVSLIIDGTFDDKSFNESALNG

VKKVKEEFKIELVLKESSSNSYLSDLEGLKDAGSDLIWLIGYRFSDVAKVA

ALQNPDMKYAIIDPIYSNDPIPANLVGMTFRAQEGAFLTGYIAAKLSKTGK

IGFLGGIEGEIVDAFRYGYEAGAKYANKDIKISTQYIGSFADLEAGRSVAT

RMYSDEIDIIHHAAGLGGIGAIEVAKELGSGHYIIGVDEDQAYLAPDNVIT

STTKDVGRALNIFTSNHLKTNTFEGGKLINYGLKEGVVGFVRNPKMISFEL

EKEIDNLSSKIINKEIIVPSNKESYEKFLKEFI.

P39 *B. burgdorferi* 297

SEQ ID NO: 68

MNKILLLILLESIVFLSCSGKGSLGSEIPKVSLIIDGTFDDKSFNESALNG

VKKVKEEFKIELVLKESSSNSYLSDLEGLKDAGSDLIWLIGYRFSDVAKVA

ALQNPDMKYAIIDPIYSNDPIPANLVGMTFRAQEGAFLTGYIAAKLSKTGK

IGFLGGIEGEIVDAFRYGYEAGAKYANKDIKISTQYIGSFADLEAGRSVAT

RMYSDEIDIIHHAAGLGGIGAIEVAKELGSGHYIIGVDEDQAYLAPDNVIT

STTKDYGRALNIFTSNHLKTNTSEGGKLINYGLKEGVVGFVRNPKMISFEL

EKEIDNLSSKIINKEIIVPSNKESYEKFLKEFI.

P39 *B. afzelii*

SEQ ID NO: 69

MNKLLLLILFEGVIFLSCSGKSGLESGIPKVSLVIDGTFDDKSFNESALNG

VKKLKEEFEIELVLKESSTNSYLSDLEGLKDAGSNLIWLIGYKFSDVAKAV

SLQNSEMKYAIIDPVYSNEPIPANLVGMTFRAQEGAFLTGYIAAKVSKTGK

IGFLGGIEGDIVDAFRYGYEAGAKYANKDIKIFSQYIGSFSDLEAGRSVAT

KMYSDGIDIIHHAAGLGGIGAIEVAKELGSGHYIIGVDEDQSYLAPNNVIT

STTKDVGRSLNLFTSNYLKTNTFEGGKLINYGLKEGVVGFVRNPKMIPFEV

EKEIDSLSSKIINKEVIVPYNKESYEKFLKEFI.

P39 *B. spielmanii*

SEQ ID NO: 70

MNKLLLFILLEGIIFLSCSDKGGLENKIPKVSLIIDGTFDDKSFNESALNG

VKKLKEEFEIDLVLKESSTNSYVSDLEGLKDAGSNLIWLIGYKFSDVAKAV

SLQNSEMKYAIIDPVYSSEPIPANLVGMTFRAQEGAFLTGYIASKVSKTGK

IGFLGGIEGDIVDAFRYGYEAGAKYANKDIKIFSQYIGSFADIEAGRSVAT

KMYSDGIDIIHHAAGLGGIGAIEVAKELGSGHYIIGVDEDQSYLAPNNVIT

SSTKDVGRSLNLFTSNYLKTNNFEGGKLINYGLKEGVVGFVRNPKMIPFEV

EKEIDSLSGKIINKEVIVPYNKESYEKFLKEFL.

P39 *B. valaisiana*

SEQ ID NO: 71

MSKLLLLILFESIIFLSCSGKGSLEGGIPKVSVIIDGTFDDKSFNESALNG

IKKVKEEFKVEFVLKESSSNSYLSDLEGLKDTGSNLIWLIGYRFSDVAKVV

SLQNSEVKYAIIDPVYSSEPIPANLVGMTFRAQEGAFLTGYIASKVSKTGK

IGFLGGIKSEIVDAFRYGYEAGAKYANKDIKIFTHYIGSFADLEASRSIAI

KMYSDGIDIIHHAAGLGGIGAIEVAKELGSGHYIIGVDEDQSYLAPDNVIT

SSTKDVGRALNIFTSNYLKTNTFEGGKLINYGLKEGVVGFVRNPKMIPFEL

EKEIDSISSKIINKEVIVPYNKESYEKFLKEFI.

P39 *B. garinii*

SEQ ID NO: 72

MNKSLLLILFECIIFLSCGGKGSLESEIPKVSLIIDGTFDDKSFNESALNG

IKKVKEEFKIEPVLKESSINSYLSDLEGLKDTGSNLIWLIGYKFSDVAKAV

SLQNPEIKYAIIDPIYSDEPIPANLVGMTFRSQEGAFLTGYIAAKVSKTGK

IGFLGGIEGEIVDSFRYGYEAGAKYANKDIKISAYYIGSFADLEAGRSVAT

KMYSDGIDIIHHAAGLGGIGALEVAKELGSGHYIIGVDEDQSYLAPNNIIT

SATKDVGRSLNIFTSNYLKTNTFEGGRLINYGLKEGVVGFVKNPKMIPFEL

EKEIDNLSSKIINKEIIVPYNKESYEKFLKE.

consensus

SEQ ID NO: 73

MNKLLLLILFEXXXFLSCSGKGSLESXIPKVSLXIDGTFDDKSFNESALNG

XKKVKEEFKXXLVLKESSXNSYLSDLEGLKDAGSXLIWLIGYKFSDVAKAV

SLQNSXMKYAIIDPXYSNXPIPANLVGMTFRAQEGAFLTGYIAAKVSKTGK

IGFLGGIEGXIVDAFRYGYEAGAKYANKDIKIFXQYIGSFADLEAGRSXAT

KMYSDGIDIIHHAAGLGGIGAIEVAKELGSGHYIIGVDEDQSYLAPXNXIT

SXTKDVGRSLNIFTSNYLKTNTFEGGKLINYGLKEGVVGFVRNPKMIPFEL

EKEIDSLSSKIINKEXIVPYNKESYEKFLKEFI.

DETAILED DESCRIPTION

The present disclosure provides novel compositions and methods for diagnosing, and treating Lyme disease (sometimes referred to as LD herein) resulting from infection by diverse *Borrelia burgdorferi* species. As discussed above, the current Centers for Disease Control and Prevention (CDC) surveillance criteria features two-tier *Borrelia burgdorferi* sensu stricto (Bbss) testing and has been estimated to capture less than one out of every 10 cases of Lyme disease. Lyme disease prevalence is clearly underreported, and the experiments described in the Exemplification section which follows shows that a percentage of people exhibiting Lyme disease symptoms, who have failed to meet CDC surveillance criteria, are infected by members of the *Borrelia burgdorferi* sensu lato (Bbsl) complex.

The Bbsl complex comprises genetically diverse bacteria that are distributed worldwide primarily throughout the Northern hemisphere and are vectored by ixodid ticks. In the USA, LD is currently the largest vector-borne illness and causes an array of symptoms including musculoskeletal, neuropsychiatric and cardiac problems and on rare occasions even death. At least 11 Bbsl genospecies have been identified in North America including: Bbss, *B. americana, B. andersoni, B. bissettii, B. californiensis, B. carolinensis, B. garinii, B. kurtenbachii, B. laneii, B. mayonii*, and *B. spielmanii.*

To assess the impact of testing limitations and to determine levels of exposure to Bbsl, a recently developed modified Western Blot procedure was employed. The procedure, termed the line immunoblot, uses recombinant antigens from common strains and species of the Bbsl complex for the serological diagnosis of LD. As discussed in greater detail below, testing was conducted on patients with suspected tickborne disease. Data presented in the Exemplification section below confirm that the serotype makeup of spirochetal exposure appears to be more complex than has been acknowledged previously.

Using the new immunoblot test, the study of patients who met the chronic Lyme disease (CLD) case definition revealed that all had exposure to Bbsl species. Positive immunoblots were further characterized at the species level for the following Bbsl species: *B. californiensis, B. spielmanii, B. afzelli/B. garinii*, and *B. mayonii.*

Spirochetes falling into the Bbsl complex are distributed worldwide, with most cases of LD reported in the USA, Europe, and Asia. The CDC states that approximately 30,000 cases of LD are reported in the USA each year using surveillance criteria featuring two-tier Bbss testing, but when tracked by other methods it is estimated that more than 300,000 people develop LD in the USA annually. The fact that CDC surveillance criteria featuring two-tier Bbss testing captures less than one out of every ten cases shows that LD is underreported, and the results of studies described elsewhere herein suggest that some people with suspected LD have failed to meet surveillance criteria.

The immunoblot testing used in the Exemplification section below, enabled differentiation of Bbsl into five specific categories: *B. californiensis, B. spielmanii, B. mayonii*, the European species *B. afzelii/B. garinii*, and undifferentiated Bbsl species. Based on surveillance reporting in the USA, the distribution pattern of Bbss is characterized by human cases reported in all 50 states with the majority reported in the Northeast, upper Midwest and northern California. However, other Bbsl species are not detected by commercial testing in the USA. Until recently, Bbss, *B. garinii* and *B. afzelii* were considered to be the only etiologic agents of LD. Currently, nine species are said to have pathogenic potential: *B. afzelii, B. bavariensis, B. bissettii*, Bbss, *B. garinii, B. kurtenbachii, B. lusitaniae, B. speilmanii*, and *B. valaisiana*. Nine other species including *B. californiensis* have not been isolated from humans. *B. afzelii, B. garinii*, and *B. spielmanii* are considered to be *Borrelia* species primarily found in Eurasia, while *B. californiensis* is considered to be a North American species. Understanding of the pathogenicity of *Borrelia* species is evolving, and some species that have not been isolated from humans and are not considered to be pathogenic may be capable of causing illness.

Aspects of the instant disclosure provide a compositions and methods for quickly, easily, and accurately detecting Bbsl antibodies in a biological sample from a subject suspected of having LD, thereby satisfying the need for such a test. Because multiple Bbsl species have pathogenic potential for Lyme disease, and because geographic ranges of Bbsl species may overlap, tests for Bbsl species need to be inclusive—that is, a test needs to be able to detect antibodies to multiple species concurrently. The present disclosure provides for antigenic amino acid sequences specific for various *Borrelia* species. The amino acid sequences of the present disclosure encode antigenic peptides that have high specificity and/or sensitivity for the indicated species. The inclusion of antigenic peptides that exhibit cross-reactivity across *Borrelia* species boundaries is also important with respect to the development of inclusive serological, or other immunologically-based assays, wherein the goal is to detect infection, not necessarily to identify a particular species responsible for infection. For example, the disclosure includes panel immunoassays wherein, in the context of a single test screen, a full spectrum of Bbsl species are detectable.

Aspects of the present disclosure provide novel compositions and methods for diagnosing infection by Bbsl species. The disclosure is based, in part, on the discovery of species-specific amino acid sequences encoding antigenic peptides (which may also be referred to in the art as peptide antigens or antigens), as described herein. Aspects of the present disclosure provide antigen-specific amino acid sequences for Bbsl species. These novel amino acid sequences may be used in assays to identify Bbsl species in samples from subjects suspected of having Lyme disease, including but not limited to Bbsl species comprising *B. afzelii, B. garinii, B. californiensis, B. spielmanii, B. mayonii, B. valaisiana, B. bavariensis, B. burgdorferi* B31, and *B. burgdorferi* 297. With the amino acid sequences of the present disclosure, identification of Bbsl species in subject samples is performed with greater speed, sensitivity, and specificity than other current methods. The amino acid sequences of the present disclosure may be used in diagnostic and scientific assays. Non-limiting examples of suitable assays include immunoblots, line immunoblots, ELISA (enzyme-linked immunosorbent assay), etc. The amino acid sequences of the present disclosure may be used for the detection of Bbsl specific T-cells, for example, with the IgXSPOT test (IGeneX, Milpitas, CA).

In one aspect, the present disclosure is a panel for detecting IgM- or IgG-class antibodies, the panel comprising an amino acid sequence having at least 90%, 95%, 98%, 99%, 99.5%, or 100% homology to SEQ ID NO: 45, and a plurality of groups of labelled and/or tagged and/or bound amino acid sequences, wherein the labelled and/or tagged and/or bound amino acid sequences comprise amino acid sequences having at least 90%, 95%, 98%, 99%, 99.5%, or 100% homology to the corresponding amino acid sequence and retain the immunological binding profile of the corresponding non-variant, and wherein the plurality of groups of labelled and/or tagged and/or bound amino acid sequences is selected from the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32 and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43. In some aspects, the panel may further comprise one or more of amino acid sequences having at least 90%, 95%, 98%, 99%, 99.5%, or 100% homology to SEQ ID NO: 44 and SEQ ID NO: 46, and variants thereof which retain the immunological binding profile of the corresponding non-variant. In some aspects, the panel may not comprise an amino acid sequence having at least 90%, 95%, 98%, 99%, 99.5%, or 100% homology to SEQ ID NO: 45 or variants thereof which retain the immunological binding profile of the corresponding non-variant.

Sequences with less than 100% homology may be modified with one or more substitutions, deletions, insertions, or other modifications with respect to the amino acid sequences provided herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E), 3) Asparagine (N), Glutamine (Q); 4) Arginine (R), Lysine (K), 5) Isoleucine (I), Leucine (L), Methionine (M), Valine (V); 6) Phenylalanine (F), Tyrosine (Y), Tryptophan (W); 7) Serine (S), Threonine (T), and 8) Cysteine (C), Methionine (M) (see, e.g., Creighton, Proteins (1984)). One of ordinary skill in the art can determine if sequences with less than 100% homology can bind naturally- or non-naturally-occurring Bbsl-related antibodies, as well as the sensitivity and specificity of the antibody to the modified sequences. One of ordinary skill in the art will be able to identify sequences with significant homology to SEQ ID NOs: 1-46 of the present disclosure that give acceptable or equivalent responses in the methods of the present disclosure without undue experimentation, in view of the teachings of this specification.

The present disclosure, in one aspect, is a panel for detecting IgM- or IgG-class antibodies, the panel comprising SEQ ID NO: 45 and a plurality of groups of labelled and/or tagged and/or bound amino acid sequences, wherein the labelled and/or tagged and/or bound amino acid sequences comprise amino acid sequences and variants thereof which retain the immunological binding profile of the corresponding non-variant, and wherein the plurality of groups of labelled and/or tagged and/or bound amino acid sequences is selected from the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32 and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43. In some aspects, the panel may further comprise one or more of SEQ ID NO: 44 and SEQ ID NO: 46, and variants thereof which retain the immunological binding profile of the corresponding non-variant. In some aspects, the panel may not comprise SEQ ID NO: 45 or variants thereof which retain the immunological binding profile of the corresponding non-variant. Non-limiting examples of panels of the present disclosure include: a panel comprising SEQ ID NO: 45 and groups (i)-(xii); a panel comprising SEQ ID NO: 45, groups (i)-(xii), and SEQ ID NOs: 44 and 46; a panel comprising SEQ ID NO: 45, groups (i)-(iv) and (vii)-(xii); a panel comprising SEQ ID NO: 45 and groups (i)-(vi), and a panel comprising groups (i)-(vi). Variants of amino acid sequences SEQ ID NOs: 1-46 which retain the immunological binding profile of the corresponding non-variant may have conservative amino acid substitutions in conserved or non-conserved regions. The expression "variants" encompasses any modification(s) of a specified amino acid sequence (e.g., SEQ ID NOs: 1-46) which retain(s) the immunological binding profile of the corresponding non-variant. Such modifications may include insertions and deletions (internal or from the N- or C-terminus, or both).

Alignment data is provided in the drawings showing amino acid sequence comparisons across species boundaries. One skilled in the art, using no more than routine experimentation, could design and produce antigenic peptides carrying conservative amino acid substitutions in non-conserved regions, or even at non-conserved amino acid positions as identified by alignment comparisons.

Nucleic acid sequences, including polynucleotides and oligonucleotides, encoding the amino acid sequences of the present disclosure, and portions thereof, may be expressed in cultured cells to provide isolatable quantities of peptides displaying biological (e.g., immunological) properties of the antigenic peptide encoded by the amino acid sequences of the present disclosure. Because of redundancy of the genetic code, multiple nucleic acid sequences may be suitable for the production of the peptide sequences of the present disclosure. One of ordinary skill in the art will be able to determine one or more nucleic acid sequences for production of the amino acid sequences of the present disclosure. A nucleic acid sequence encoding an amino acid sequence of the present disclosure may be labeled by any suitable label known to one of ordinary skill in the art.

In this regard, nucleic acid sequences suitable for the production of the amino acid sequences of the present disclosure may be substantially homologous to naturally occurring sequences. Substantial homology of a nucleic acid sequence as used herein means that: (a) there is greater than 65%, 75%, 85%, 95%, 98%, or 99% homology with the naturally occurring sequence, or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45° C., and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature. One of ordinary skill in the art will be able to determine suitable conditions for determining the homology of the nucleic acid sequences encoding the antigenic peptides of the present disclosure.

Homologous nucleic acid sequences may be determined based on the nature of a nucleotide substitution in the nucleic acid sequence. For example, synonymous nucleotide substitutions, that is, nucleotide changes within a nucleic acid sequence that do not alter the encoded amino acid sequence, will be better tolerated and, therefore, may be more numerous in a particular nucleic acid sequence than non-synonymous nucleotide substitutions. One of ordinary skill in the art will be able to determine the suitable number and location of substitutions that may be allowed in a nucleic acid sequence that encodes an amino acid sequence of the present disclosure without adversely affecting the antigenicity of the encoded antigenic peptide, without undue experimentation.

In another aspect, the present disclosure is a panel for detecting IgM- or IgG-class antibodies, the panel comprising SEQ ID NO: 45 and a plurality of groups of labelled and/or tagged and/or bound amino acid sequences, wherein the labelled and/or tagged and/or bound amino acid sequences comprise amino acid sequences and variants thereof which retain the immunological binding profile of the corresponding non-variant, and wherein the plurality of groups of labelled and/or tagged and/or bound amino acid sequences consist of the following groups: (i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; (ii) SEQ ID NO: 21, SEQ ID NO: 22, SEQ ID NO: 23, SEQ ID NO: 24, SEQ ID NO: 25, and SEQ ID NO: 26; (iii) SEQ ID NO: 32 and SEQ ID NO: 33; (iv) SEQ ID NO: 27 and SEQ ID NO: 28; (v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; (vi) SEQ ID NO: 34, SEQ ID NO: 35, SEQ ID NO: 36, SEQ ID NO: 37, SEQ ID NO: 38, and SEQ ID NO: 39; (vii) SEQ ID NO: 29; (viii) SEQ ID NO: 30; (ix) SEQ ID NO: 31; (x) SEQ ID NO: 40; (xi) SEQ ID NOs: 41 and 42; and (xii) SEQ ID NO: 43. In some aspects, the panel may further consist of one or more of SEQ ID NO: 44 and SEQ ID NO: 46, and variants thereof which retain the immunological binding profile of the corresponding non-variant. In some aspects, the panel may not consist of SEQ ID NO: 45 or variants thereof which retain the immunological binding profile of the corresponding non-variant. As used herein, "consist of" or "consisting of", when used as a claim transition referring to an amino acid sequence, refers to amino acid sequences having 100% homology to the specified amino acid sequence (i.e., SEQ ID NOs: 1-46).

With regard to the present disclosure, the phrase "wherein the plurality of groups of labelled and/or tagged and/or bound amino acid sequences consist of the following groups" encompasses a composition having the one or more of the recited sequences and, for example, buffers, labels, etc. In other words, the sequence is limited to the sequence or sequences given but the composition is not limited. The definition specifically excludes amino acids naturally contiguous with a recited sequence being used as a label or tag, such as an oligonucleotide mass tag (OMT) for detection with mass spectrophotometry, as an element of the "composition comprising."

Labels and Tags

One or more amino acid sequences of the disclosure may be labelled and/or tagged and/or bound. In the context of the present disclosure, a "labelled" or "tagged" amino acid sequence is an amino acid sequence that is attached to a detectable moiety. As used herein, a "label" or "tag" is a detectable moiety that may be attached to an amino acid sequence of the disclosure. A label or tag may be covalently or non-covalently attached to an amino acid sequence of the disclosure. Non-limiting examples of such "tags" are natural and synthetic (i.e., non-naturally occurring) nucleic acid and amino acid sequences (e.g., poly-AAA tags), antibodies and detectable moieties such as labels (discussed below). Thus, the definitions of the phrases "labelled" and "tagged" may have overlap in that a tag may also, in some instances, function as a label. Further, tags useful with the present disclosure may be linked to a label.

The amino acid sequences of the present disclosure, or any tags attached to an amino acid sequence of the present disclosure, may be labeled with any suitable label known to one of ordinary skill in the art. Such labels may include, but are not limited to, biotin/streptavidin, enzyme conjugates (e.g., horseradish peroxidase (HRP), alkaline phosphatase (AP), glucose oxidase and β-galactosidase), fluorescent moieties (e.g., FITC, fluorescein, rhodamine, etc.), biological fluorophores (e.g., green fluorescent protein, R-phycoerythrin) or other luminescent proteins, etc. Any suitable label known to one of ordinary skill in the art may be used with the present disclosure.

Further, in some aspects, the amino acid sequences of the present disclosure may be "bound." A "bound" amino acid sequence is an amino acid sequence that has been immobilized in order to permit the use of the amino acid sequence in a biological test such as, for example, immunoassays. In the context of the present disclosure, a "bound" amino acid sequence is an amino acid sequence attached (e.g., covalently or non-covalently bound, etc.) directly or indirectly to a non-natural surface or substance. Further still, the "bound" amino acid sequences of the present disclosure may be attached, directly or indirectly, to a natural surface or substance, either of which is not naturally associated with the amino acid sequence. Non-limiting examples of substances to which the amino acid sequences of the present disclosure may be bound are nitrocellulose, nylon, polyvinylidene difluoride (PVDF), plastics, metals, magnetic beads and agarose (e.g., beads). Linking agents known to those of ordinary skill in the art may be used to aid or enhance binding of the amino acid sequences of the present disclosure to a surface or substance.

Production of Amino Acid Sequences

In some aspects, amino acid sequences of the present disclosure may be natural occurring and isolated from a natural source. Further, in some aspects, amino acid sequences of the present disclosure may be non-natural, synthetic sequences, such as sequences produced by recombinant technology or sequences synthesized by protein synthesizing apparatuses. As such, amino acid sequences of the present disclosure may be isolated or may be produced by recombinant technology, as is described and enabled in the literature and in commonly referred to manuals such as, e.g., Short Protocols in Molecular Biology, Second Edition, F. M. Ausubel, Ed., all John Wiley & Sons, N.Y., edition as of 2008; and, Sambrook, et al., Molecular Cloning: A Laboratory Manual, 3rd ed., Cold Spring Harbor Laboratory Press, Cold Spring Harbor, 2001, and as is well known to one of ordinary skill in the art. In one aspect, amino acid sequences of the present disclosure are made recombinantly in *E. coli.*

As used herein, the term "vector" refers to a nucleic acid molecule capable of transporting between different genetic environments another nucleic acid to which it has been operatively linked. In addition to including a nucleic acid sequence encoding an amino acid sequence of the disclosure (e.g., SEQ ID NOs: 1-46) or variants thereof which retain the immunological binding profile of the corresponding non-variants, vectors of the present disclosure also include a heterologous nucleic acid sequence. As used herein, heterologous refers to a nucleic acid sequence that does not naturally occur in the organism from which the Markush group sequences are derived. The term "vector" may also refer to a virus or organism that is capable of transporting the nucleic acid molecule. One type of vector is a plasmid, a small, circular, double-stranded, extrachromosomal DNA molecule that is physically separate from and can self-replicate independently from chromosomal DNA. Some useful vectors are those capable of autonomous replication and/or expression of nucleic acids to which they are linked. Vectors capable of directing the expression of nucleic acids to which they are operatively linked are referred to herein as "expression vectors." Other useful vectors, include, but are not limited to bacterial plasmids and bacterial artificial chromosomes (BACs), cosmids, and viruses such as lentiviruses, retroviruses, adenoviruses, and phages.

Vectors useful in methods of the disclosure may include additional sequences including, but not limited to, one or more signal sequences and/or promoter sequences, or a combination thereof. Promoters that may be used in methods and vectors of the disclosure include, but are not limited to, cell-specific promoters or general promoters. Non-limiting examples of promoters that can be used in vectors of the disclosure are: ubiquitous promoters, such as, but not limited to: CMV, CAG, CBA, and EF1a promoters. Methods to select and use suitable promoters are well known in the art.

Vectors useful in methods of the disclosure may be used to express a fusion protein comprising sequences of the disclosure in a cell. Expression vectors and methods of their preparation and use are well known in the art. In some aspects of the disclosure, a nucleic acid sequence of an expression vector encodes a fusion protein comprising an amino acid sequence of the disclosure. It is well known in the art how to prepare and utilize fusion proteins that comprise a polypeptide sequence. In some aspects, a fusion protein comprising an amino acid sequence of the disclosure may also include an epitope tag that may be used for purification of the fusion protein or in a method of the disclosure. Non-limiting examples of epitope tags are a FLAG tag, a fluorescent tag (including but not limited to green fluorescent protein (GFP)), a GST tag, a hemagglutinin (HA), a poly-histidine (poly-His) tag, a Myc tag, an MBP tag, or a V5 tag. In some aspects, a fusion protein comprising an amino acid sequence of the disclosure may also include a detectable label, as described elsewhere herein.

Assays and Methods of Detection

Amino acid sequences of the present disclosure may be tagged with an antibody with specificity for any of said amino acid sequences. Specificity for said amino acid sequence, i.e., antibody specificity, is the property of antibodies which enables them to react preferentially with some antigenic determinants and not with others. Specificity is dependent on chemical composition, physical forces and molecular structure at the binding site. Sensitivity is how strongly the antibody binds to the antigenic determinant. One of ordinary skill in the art can easily determine specificity and sensitivity of an antibody for a particular amino acid sequence using standard affinity assays, such as immunoblotting. Ouchterlony assays, titer assays, etc.

In another aspect, the present disclosure provides methods of quickly and accurately detecting Bbsl antibodies in a sample from a subject suspected of having Lyme disease. Methods of the present disclosure for detecting Bbsl antibodies in a sample from a subject suspected of having Lyme disease, may comprise, for example, providing a biological sample (including but not limited to blood, saliva) obtained from a subject suspected of having Lyme disease, mixing the biological sample with one or more of the labeled and/or bound amino acid sequences of the present disclosure and detecting a positive immunobinding reaction which indicates the presence of Lyme disease causing bacteria specific antibodies in the sample. The antibodies may be detected by, for example, immunoblotting, Elispot, ELISA, Western blotting, lateral flow assay, or any other appropriate immunoassay known to one of ordinary skill in the art. These techniques are known to one of ordinary skill in the art and procedures can be found in common technical references. While similar, each of these techniques has its advantages and disadvantages. Other suitable techniques may be known to those of skill in the art and are incorporated herein.

To assess the impact of testing limitations and to determine levels of exposure to Bbsl species, a modified Western blot procedure, the line immunoblot, was developed and employed in aspects of the disclosure described herein. A line immunoblot uses recombinant antigens from multiple Bbsl complex strains and species for serological identification and diagnosis of LD in serum from patients with suspected LD. As described elsewhere herein, the serotype makeup of Bbsl exposure may be more complex than has been previously acknowledged, and infection with more than one Bbsl species is possible.

Western blotting can involve separating proteins by electrophoresis and then transferring to nitrocellulose or other solid media (e.g., polyvinylidene fluoride or PVDF-membrane and nylon membrane), and is described in more detail below. Immunoblotting can also involve applying proteins to a solid media manually or by machine. Preferably, the proteins are applied in straight lines or spots and dried, binding them to the solid support medium, e.g., nitrocellulose. The proteins used in an immunoblot can be isolated from biological samples or produced by recombinant technology, as is well known by those of ordinary skill in the art. The bound proteins are then exposed to a sample or samples suspected of having antibodies specific for the target proteins. With this procedure, a known antibody can be used to determine if a protein is present in a sample, such as when the proteins of lysed cells are separated by electrophoresis and transferred to the solid medium. Western blotting allows for the identification of proteins by size as well as by specificity for a specific antibody.

Similarly, with a procedure called immunoblotting, known proteins can be bound to the solid medium and samples, such as samples from subjects suspected of having an infection, can be tested for the presence of specific antibodies in the sample by contacting the bound protein with the sample. An antibody that binds the target protein is usually referred to as the primary antibody. A secondary antibody, specific for conserved regions of the primary antibody (for example, a rabbit-anti-human IgG antibody may be used to detect primary human antibodies) is used to detect any bound primary antibodies. The secondary antibody is usually labeled with a detectable moiety for visualization. Non-limiting examples of suitable labels include, for example, chromophores such as biotin, radioactive moieties and enzymes such as alkaline phosphatase, etc. The use of these and other materials for the visualization of antibodies are well known to one of ordinary skill in the art.

The Enzyme-Linked ImmunoSpot (ELISPOT) method can detect human T cells that respond to Lyme-specific antigens in vitro. In an ELISPOT assay, the surfaces of PVDF membrane in a 96-well microtiter plate are coated with capture antibody that binds, for example, anti-Interferon gamma (IFNγ) or other cytokine-specific antibody. During the cell incubation and stimulation step, the T cells isolated from patient whole blood are seeded into the wells of the plate along with aforementioned sequence(s), and form substantially a monolayer on the membrane surface of the well. Upon stimulation of any antigen-specific cells with one or more of the sequences of the present disclosure they are activated and they release the IFNγ, which is captured directly on the membrane surface by the immobilized antibody. The IFNγ is thus "captured" in the area directly surrounding the secreting cell, before it has a chance to diffuse into the culture media, or to be degraded by proteases and bound by receptors on bystander cells. Subsequent detection steps visualize the immobilized IFNγ as an ImmunoSpot; essentially the secretory footprint of the activated cell.

For a specific example of an ELISPOT test, each well of the plate is coated with a purified cytokine-specific antibody specific for the test or cell being detected. Subject's (i.e., a subject suspected of having Lyme disease) T cells are isolated and cultured in each well and stimulated with recombinant antigens of one or more sequences of the present disclosure. Lyme-positive patient cells secrete cytokine in response to stimuli, which is captured by the antibody coated in the well and further detected by ELISA.

ELISA assays are also used to detect antigens. The ELISA assay can permit the quantification of a specific protein in a mix of proteins (for example, a lysate) or determine if a peptide is present in a sample. Likewise, ELISA assays can be used to determine if a specific antibody is present by using a specific antigen as a target. As used with the present disclosure, target amino acid sequence(s) are attached to a surface. Then, if present in the sample being tested, the reactive antibody can bind to the antigen. A secondary antibody linked to an enzyme is added, and, in the final step, a substance containing the enzyme's substrate is added. The subsequent reaction produces a detectable signal, most commonly a color change in the substrate.

Lateral flow assays, also referred to by a variety of other names that include but are not limited to lateral flow tests, lateral flow devices, lateral flow immunoassays, lateral flow immunochromatographic assays, and rapid tests, are simple, versatile, paper-based platforms for detecting and/or quantifying the presence of one or more analytes, such as an antigen, in a mixture, such as a liquid sample. Lateral flow assays may be qualitative or quantitative. In a lateral flow assay, a sample containing one or more analytes of interest is applied to an adsorbent sample pad and is drawn via capillary action through various zones of polymeric test strips to which are attached molecules that can interact with the analyte(s). The sample migrates to the conjugate release pad, which contains molecules that specifically bind to the analyte(s) of interest and are conjugated to fluorescent, colored, or otherwise detectable particles. Finally, the sample, including the bound analyte(s) migrates into the detection zone. Within the porous membrane of the detection zone are biological components such as antibodies or antigens, that are immobilized in lines and that will react with the detectable particles. Lateral flow assays typically have a control line for confirming sample flow through the strip and one or more test lines for detecting the presence of the analyte(s) of interest. The results may be read by eye or with a machine capable of reading and interpreting the results. A lateral flow assay may be designed as a direct or "sandwich" assay, in which the presence of a colored line at the test line position indicates a positive test, or as a competitive assay, in which the absence of a colored line indicates a positive test. Direct and competitive assays may be multiplexed.

In one aspect of a method of the present disclosure, a positive result for infection by one or more Bbsl species is indicated when a biological sample obtained from a subject suspected of having Lyme disease is contacted with a screening panel of the disclosure under conditions appropriate for specific antibody binding to an epitope, and specific binding of IgM- or IgG-class antibodies, if present in the biological sample, with amino acid sequences included in the selected groups of the screening panel is detected, wherein a positive immunobinding reaction with IgM-class antibodies is detected for SEQ ID NO: 45 and for at least one amino acid sequence from at least two of groups (i)-(iii) (wherein groups (i)-(iii) are as described elsewhere herein). In another aspect of the disclosure, a positive result is indicated when a positive immunobinding reaction with IgG-class antibodies is detected for SEQ ID NO: 45 and for at least one amino acid sequence from at least five of groups (i)-(iv) and (vii)-(xii) (wherein groups (i)-(iv) and (vii)-(xii) are as described elsewhere herein). In yet another aspect of the disclosure, a positive result for infection by one or more Bbsl species is indicated when a positive immunobinding reaction with IgM-class antibodies is detected for SEQ ID NO: 45 and for at least one amino acid sequence from at least two of groups (i)-(iii) and (v) (wherein groups (i)-(iii) and (v) are as described elsewhere herein). In another aspect, a positive result is indicated when a positive immunobinding reaction with IgG-class antibodies is detected for SEQ ID NO: 45 and for at least one amino acid sequence from at least two of groups (i)-(vi) (wherein groups (i)-(vi) are as described elsewhere herein).

In another aspect of a method of the present disclosure, a positive result for infection by one or more Bbsl species is indicated when a biological sample obtained from a subject suspected of having Lyme disease is contacted with a screening panel of the disclosure under conditions appropriate for specific antibody binding to an epitope, and specific binding of IgM- and IgG-class antibodies, if present in the biological sample, with amino acid sequences included in the selected groups of the screening panel is detected, wherein a positive immunobinding reaction with IgM-class or IgG-class antibodies is detected for SEQ ID NO: 45, and a positive immunobinding reaction with IgM-class antibodies is detected for at least one amino acid sequence from at least two of groups (i)-(iii) (wherein groups (i)-(iii) are as described elsewhere herein) and a positive immunobinding reaction with IgG-class antibodies is detected for at least one amino acid sequence from at least five of groups (i)-(iv) and (vii)-(xii) (wherein groups (i)-(iv) and (vii)-(xii) are as described elsewhere herein). In another aspect, a positive result is indicated when a positive immunobinding reaction with IgM-class or IgG-class antibodies is detected for SEQ ID NO: 45, and a positive immunobinding reaction with IgM-class antibodies is detected for at least one amino acid sequence from at least two of groups (i)-(v) (wherein groups (i)-(v) are as described elsewhere herein), and a positive immunobinding reaction with IgG-class antibodies is detected for at least one amino acid sequence from at least two of groups (i)-(vi) (wherein groups (i)-(vi) are as described elsewhere herein).

In yet another aspect of a method of the present disclosure, a positive result for infection by one or more Bbsl species is indicated when a biological sample obtained from a subject suspected of having Lyme disease is contacted with a screening panel of the disclosure under conditions appropriate for specific antibody binding to an epitope, and specific binding of IgM- or IgG-class antibodies, if present in the biological sample, with amino acid sequences included in the selected groups of the screening panel is detected, wherein a positive immunobinding reaction IgM-class antibodies is detected for at least one amino acid sequence from at least two of groups (i)-(iii) (wherein groups (i)-(iii) are as described elsewhere herein). In one aspect, a positive result is indicated when a positive immunobinding reaction with IgG-class antibodies is detected for at least one amino acid sequence from at least five of groups (i)-(iv) and (vii)-(xii) (wherein groups (i)-(iv) and (vii)-(xii) are as described elsewhere herein). In another aspect, a positive result is indicated when a positive immunobinding reaction with IgM-class antibodies is detected for at least one amino acid sequence from at least two of groups (i)-(iii) and (v) (wherein groups (i)-(iii) and (v) are as described elsewhere herein). In yet another aspect, a positive result is indicated when a positive immunobinding reaction with IgG-class antibodies is detected for at least one amino acid sequence from at least two of groups (i)-(vi) (wherein groups (i)-(vi) are as described elsewhere herein).

In methods of the present disclosure, any primary antibody bound to a peptide encoded by an amino acid sequence of the present disclosure may be detected with anti-human antibodies, such as IgG or IgM, used as the secondary antibody conjugated to a detectable moiety. As discussed elsewhere herein, the detectable moiety may be selected from the group consisting of chromophores, radioactivity moieties and enzymes or other detectable moiety known to one of ordinary skill in the art. In one aspect, the detectable moiety comprises alkaline phosphatase. In another aspect the detectable moiety comprises biotin.

In another aspect of the disclosure, a method is provided for detecting and distinguishing various species of *Borrelia* in a sample. The sample may be from a subject suspected of having Lyme disease. The method may comprise, for example, providing a sample, for example, a biological sample obtained from a subject suspected of having Lyme disease and mixing or contacting the biological sample with a panel of the present disclosure. Amino acids may be labeled to confirm their presence if positive results are not obtained in the assay. In an aspect of the disclosure, a sample is considered positive in a multi-species panel assay for *Borrelia* if at least one amino acid sequence is detected from at least two groups of the panel. A sample is considered positive for a specific species of *Borrelia* if at least two amino acid sequences identified with the specific species are detected.

Subjects and Cells

As used herein, a subject may be an animal, such as a mammal or a non-mammal. Non-limiting examples of mammalian subjects include primates (including but not limited to humans), rodents (including but not limited to mice, rats, squirrels, chipmunks, prairie dogs), lagomorphs, deer, canids (including but not limited to dogs, foxes, coyotes, and wolves), felids (including but not limited to domestic cats, bobcats, cougars, and other wild cats), bears, horses, cows, sheep, goats, and pigs. Non-limiting examples of non-mammalian subjects include birds, amphibians, lizards, insects, and arthropods. As used herein, a cell may be a bacterial cell, including but not limited to *E. coli*, or an animal cell, either mammalian or non-mammalian.

EXEMPLIFICATION

Example 1. Lyme ImmunoBlot Antigen Specificity

The Lyme ImmunoBlot IgG and IgM Tests are qualitative immunoblot assays that detect IgG and IgM antibodies directed against *B. burgdorferi* sensu lato species in serum samples suspected of having Lyme disease. Recombinant *B. burgdorferi* sensu lato antigens are sprayed as straight lines onto nitrocellulose strips, which are then used in the Lyme ImmunoBlot Test. Experiments were undertaken to determine the specificity of the Lyme ImmunoBlot Test.

Methods

Antigen Preparation

Recombinant target proteins were obtained by cloning hybrid gene constructs or portions of genes into pET vectors, expressing the gene products in *Escherichia coli* (GenScript, Piscataway, NJ USA), then isolating the proteins to >90% purity, as previously described [Liu et al., *Healthcare* (2018) 6(3) pii: E99: Shah et al., *Healthcare* (2019) 7:121], Bbsl recombinant proteins were derived from several US and European species of Bbsl including Bbss strains B31 and 297 for the detection of the following targets: P23 (OspC), P31 (OspA), P34 (OspB), P39 (BmpA), P41, P93, the variable surface antigen of Bbss (VlsE), and C6 (a hybrid protein containing the immunodominant region of VlsE from different Bbsl species) for IgM ImmunoBlot and all the above, plus P66, P58, P45, P30, P28, P18, for IgG as previously described. The targeted Bbsl species were Bbss (*B. burgdorferi B*31 and *B. burgdorferi* 297), *B. afzelii, B. garinii, B. californiensis, B. mayonii, B. spielmanii*, and *B. valaisiana*. For specificity controls, recombinant proteins from several tick-borne relapsing fever (TBRF) *Borrelia* species (*B. hermsii, B. miyamotoi, B. turicatae* and *B. turcica*) were derived for the detection of four target antigens: BipA, GlpQ, fHbp and FlaB, as previously described [Shah et al., *Healthcare* (2019) 7:121].

Preparation of Antigen Strips

Antigen strips for Bbsl and TBRF immunoblots were prepared as previously described [Liu et al., *Healthcare* (2018) 6(3) pii: E99; Shah et al., *Healthcare* (2019) 7:121]. In brief, purified proteins and control proteins were diluted (7-19 ng protein/line) and sprayed in straight lines on nitrocellulose sheets (Amersham Protran, GE Healthcare Life Science) using a BioDot liquid dispenser (BioDot, Irvine, CA, USA). The sheets were then blocked with 5% non-fat dry milk and sliced into 3 mm wide strips.

Detection of Antibody Reactivity

Serological immunoblot testing was performed at IGeneX Reference Laboratory, a high-complexity testing facility with Clinical Laboratory Improvement Amendments (CLIA) certification. Lyme ImmunoBlot strips were tested with alkaline phosphatase (AP)-conjugated anti-rabbit antibodies rabbit anti-*Borrelia burgdorferi* serum samples and rabbit anti-TBRF *Borrelia* serum samples. Rabbit sera with antibodies to the following *B. burgdorferi* species were tested: *B. burgdorferi* sensu lato species *B. burgdorferi* B31 and *B. burgdorferi* 297; and *B. burgdorferi* sensu stricto species *B. californiensis, B. afzalii, B. garinii, B. spielmanii*, and *B. valaisiana*. Rabbit sera with antibodies to the TBRF *Borrelia* species described above were used as controls.

Reactivity between *Borrelia*-specific antibodies from test sera and *Borrelia* antigens on immunoblots was detected as previously described [Liu et al., *Healthcare* (2018) 6(3) pii:

E99; Shah et al., *Healthcare* (2019) 7:121]. In brief, strips were labeled, soaked in diluent (100 mM Tris, 0.9% NaCl, 0.1% Tween-20 and 1% non-fat dry milk) for 5 min in a trough, then a 10 μL aliquot of the test or control serum was added to the strip. Strips with sera were incubated at room temperature for one hour, washed 3 times with wash buffer (KPL, Gaithersburg, MD, USA) at room temperature, and the final wash solution was then aspirated. To detect IgG and IgM reactivity, strips were incubated with alkaline phosphatase-conjugated goat anti-human IgG at 1:10,000 dilution or IgM at 1:6000 dilution respectively (KPL, Gaithersburg, MD, USA) for one hour, then were washed 3 times. To visualize bands of antibody/antigen reactivity, the strips were reacted with a chromogenic substrate, 5-bromo-4-chloro-3-indolylphosphatenitro-blue tetrazolium (BCIP/NBT, KPL, Gaithersburg, MD, USA) and the reaction was terminated by washing with distilled water after the calibration control produced a visible band at 39 kDa. Bands demonstrating an intensity lower than that of the calibration control were reported as negative.

Scoring of Immunoblots

For Bbsl immunoblots, the following bands (in kDa) were scored for IgG reactivity: 18 (group (xii) SEQ ID NO: 43), 23 (OspC; group (i) SEQ ID NOs: 1-10), 28 (group (xi) SEQ ID NOs: 41 and 42), 30 (group (x) SEQ ID NO: 40), 31 (OspA; group (v) SEQ ID NOs: 11-20), 34 (OspB; group (vi) SEQ ID NOs: 34-39), 39 (BmpA; group (ii) SEQ ID NOs: 21-26), 41 (FlaB; group (iii) SEQ ID NOs: 32 and 33), 45 (group (ix) SEQ ID NO: 31), 58 (group (viii) SEQ ID NO: 30), 66 (group (vii) SEQ ID NO: 29), and 83-93 (group (iv) SEQ ID NOs: 27 and 28). The following bands (in kDa) were scored for IgM reactivity: 23 (OspC; group (i) SEQ ID NOs: 1-10), 31 (Osp A; group (v) SEQ ID NOs: 11-20), 34 (Osp B; group (vi) SEQ ID NOs: 34-39), 39 (BmpA; group (ii) SEQ ID NOs: 21-26), 41 (FlaB; group (iii) SEQ ID NOs: 32 and 33) and 93 (group (iv) SEQ ID NOs: 27 and 28). Interpretation of immunoblots was determined by two different criteria: CDC criteria, and in-house criteria, as previously described [Liu et al., *Healthcare* (2018) 6(3) pii: E99]. By CDC criteria, IgM reactivity was interpreted as positive if two of the three antigen bands 23, 39, and 41 kDa were positive, and IgG reactivity was interpreted as positive if five of the ten antigen bands 18, 23, 28, 30, 39, 41, 45, 58, 66, and 83-93 were positive. By in-house criteria, IgM reactivity was considered positive if two of the four bands of 23, 31, 39, and 41 kDa were present, and IgG reactivity was considered positive if two out of the six bands of 23, 31, 34, 39, 41, and 83-93 kDa were present.

Results

Figure 2:
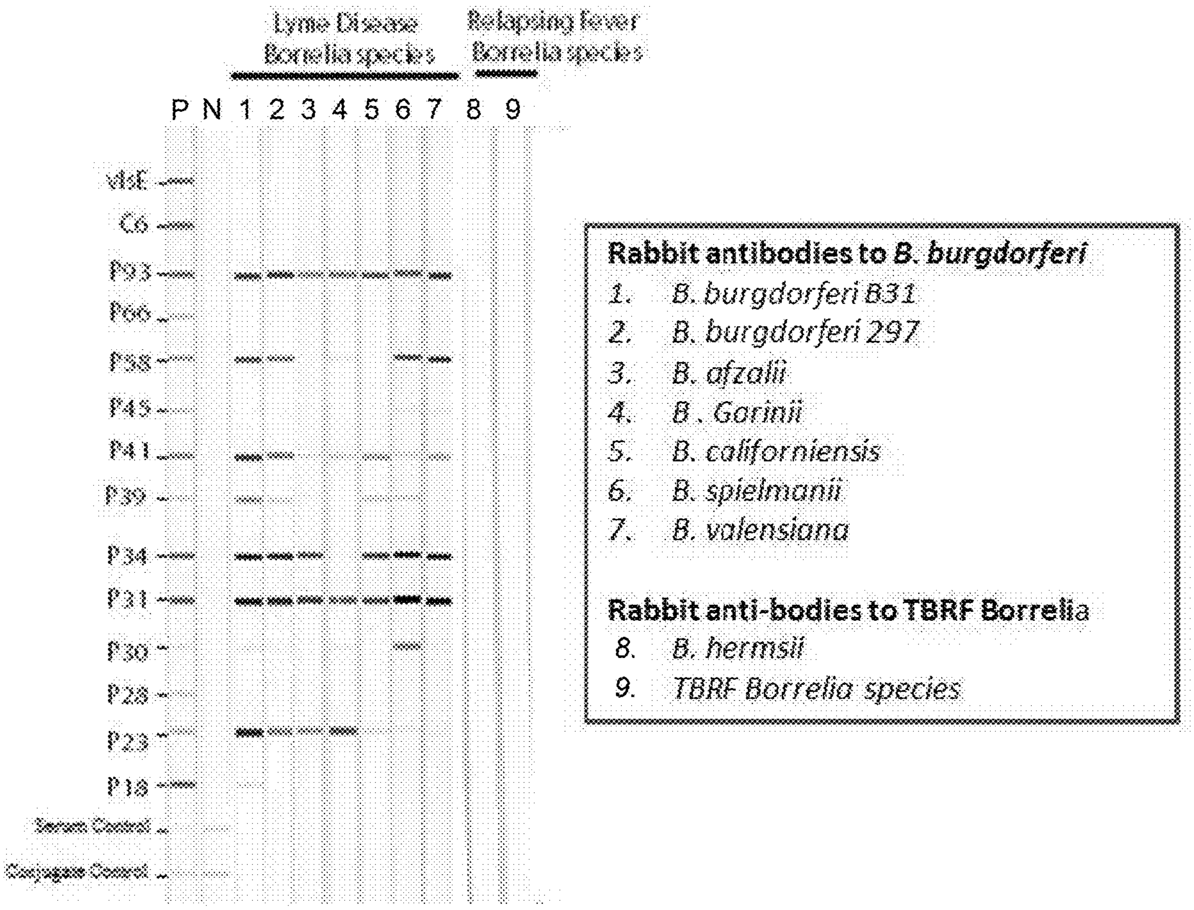
FIG. 2 presents a photomicrographic image showing that Lyme ImmunoBlot strips were tested with rabbit anti-*Borrelia burgdorferi* serum samples and rabbit anti-TBRF *Borrelia* serum samples. Rabbit sera with antibodies to the following *B. burgdorferi* species were tested: *B. burgdorferi* sensu lato species *B. burgdorferi* B31 (1) and *B. burgdorferi* 297 (2); and *B. burgdorferi* sensu stricto species *B. californiensis* (3), *B. afzalii* (4), *B. garinii* (5), *B. spielmanii* (6), and *B. valensiana* (7). Rabbit sera with antibodies to the following TBRF *Borrelia* species were used as controls: *B. hermsii* (8) and TBRF *Borrelia* species *B. coriaceae* (9).

As shown in FIG. 2, antibodies to *B. burgdorferi* species were detected, indicating that the Lyme ImmunoBlot is specific for the detection of *B. burgdorferi* group antibodies. A low signal to only 41 kDa was detected with rabbit anti-TBRF *Borrelia* specific serum samples.

Example 2. Lyme ImmunoBlots Validation Study for Clinical Sensitivity and Specificity A total of 178 patient samples were tested as per Lyme ImmunoBlot IgM and IgG protocols to determine clinical sensitivity and specificity. The following patient samples were tested as per Lyme Immunoblot IgM and IgG test protocols. The ImmunoBlots were read by in-house criteria and CDC criteria.

Methods

Antigen Preparation

Antigens were prepared substantially as described in Example 1. The targeted Bbsl species were were Bbss (*B. burgdorferi* B31 and *B. burgdorferi* 297), *B. californiensis, B. spielmanii, B. afzelii, B. garinii*, and *B. mayonii.*

Preparation of Antigen Strips

Antigen strips were prepared substantially as described in Example 1. Protein L (Sigma, St, Louis, MO, USA) and mixed human IgM and IgG (Sigma, St. Louis, MO, USA) were used as control proteins for detecting the addition of human serum and for detecting the addition of alkaline phosphatase conjugated anti-human antibodies.

Detection of Antibody Reactivity

Serological immunoblot testing and detection of antibody reactivity were performed substantially as described in Example 1. Human sera from patients with confirmed *Borrelia* infection were used as positive controls and sera from uninfected persons were used as negative controls. All immunoblot testing of patient samples was performed with simultaneous testing of positive and negative control serum samples.

Scoring of Immunoblots

Figure 3:
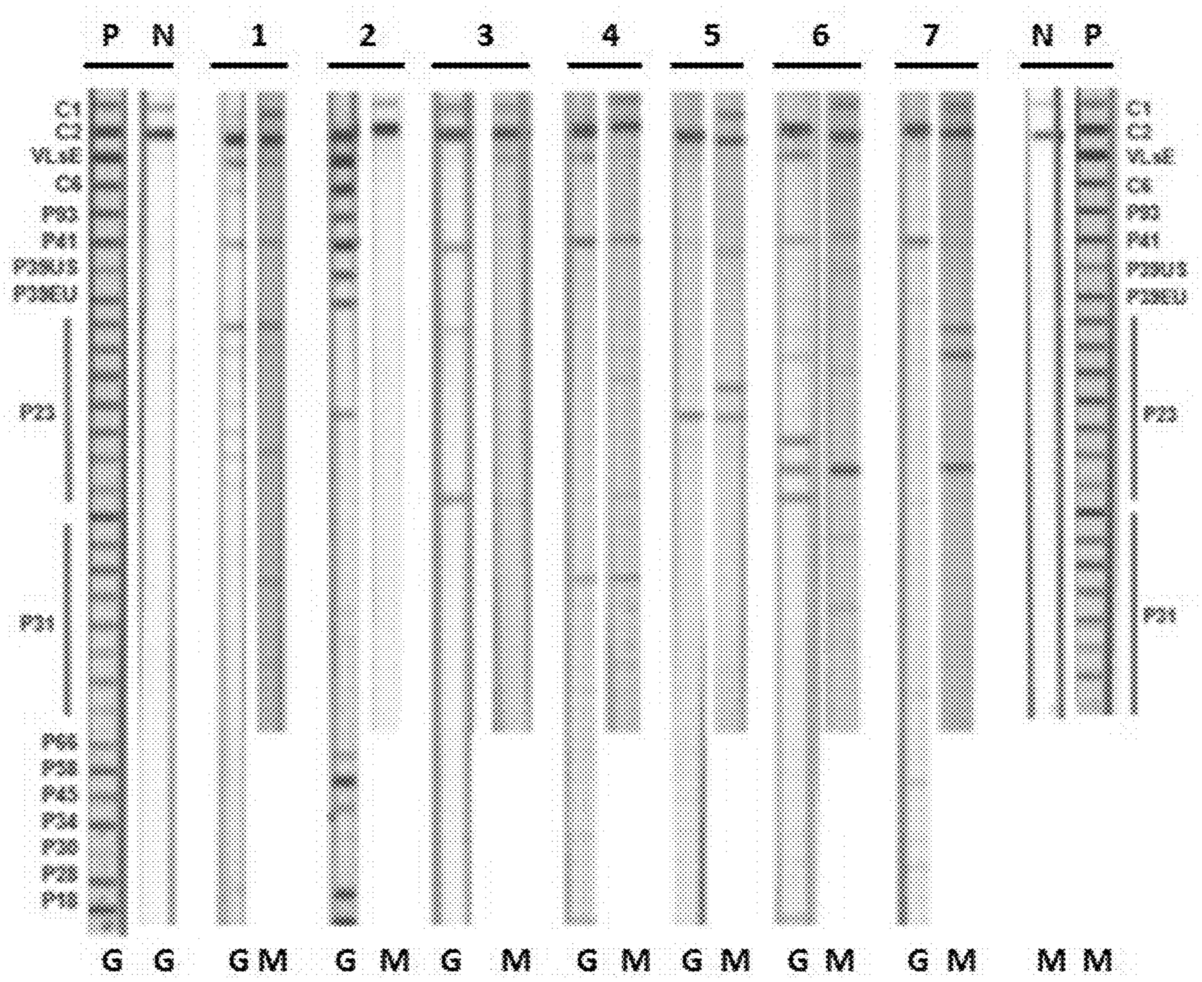
FIG. 3 presents a photomicrographic image showing immunoblot reactivity of patient serum samples for *Borrelia burgdorferi* sensu lato (Bbsl) species. Immunoblot strips with recombinant *Borrelia* antigens were incubated with representative patient serum samples. Lanes are identified as follows: P, positive control; N, negative control; 1, *B. burgdorferi* B31 positive IgM & IgG; 2, *B. mayonii* positive IgG; 3, *B. speilmanii* positive IgG; 4, *B. californiensis* positive IgM & IgG; 5, mixed infection *B. mayonii* and *B. californiensis* positive IgM; 6, *B. burgdorferi* European species (*B. burgdorferi* sensu stricto, *B. afzelli* and *B. garinii* and *B. speilmanii*) positive IgM & IgG; 7, Bbss and *B. burgdorferi* European species positive IgM. G indicates a Bbsl Immunoblot IgG test; M indicates a Bbsl Immunoblot IgM test.

Bbsl immunoblots were scored substantially as described in Example 1. Immunoblot reactivity for Bbsl in representative patient serum samples is shown in FIG. 3.

Patients and Data Collection

The patient cohort was recruited from a medical practice located in San Francisco, CA, specializing in the diagnosis and treatment of tick-borne diseases. The Western Institutional Review Board (WIRB), Puyallup, WA approved the anonymous retrospective data collection protocol and consent form. Patients of either sex qualified for the study provided they were at least 18 years of age, had a medical history of musculoskeletal, neuropsychiatric and/or cardiac symptoms consistent with LD, and gave written informed consent for data collection. Subjects were included in the study if they met the case definition of untreated or previously treated chronic LD with symptoms lasting more than six months, as described in detail elsewhere [Cameron et al., *Expert Rev Anti Infect Ther*. (2014) 12:1103-1135; Stricker et al., *Am J Infect Dis* (2018) 14:1-44]. Patients were not required to have had a documented tick bite or erythema migrans rash for participation in the study because serological testing was used to detect exposure rather than active infection. De-identified patient samples were coded according to the patient's place of residence. Blood was drawn and serum was separated at independent laboratories including BioReference®, LabCorp®, and AnyLabTestNow®, and serum samples were transported to the reference laboratory for immunoblot testing.

A total of 175 human sera expected to be negative for Bbsl and TBRF were obtained from the Centers for Disease Control and Prevention (CDC), College of American Pathologists, New York State Department of Health, New York Biologics (Southampton, N.Y., USA) and IGeneX Reference Laboratory (Milpitas, CA, USA). The IGeneX samples were leftover sera received for routine testing for tick-borne diseases that would otherwise be discarded. Testing of control sera was performed by laboratory personnel in a blinded fashion in the same manner as testing of clinical samples from Bbsl and TBRF patients. Results are reported in Table 1, Table 2A-C, and Table 3.

Chronic Lyme Disease Cohort

To assess the ability of the Lyme Irrimunipblot to identify *Borrelia* seroreactivity in patients with chronic Lyme disease (CLD), an additional study was performed with serum samples from a cohort of 90 patients who met the clinical case definition of CLD, as recently described [Stricker et al.,

*Am J Infect Dis* (2018) 14:1-44]. Immunoblot testing was performed as described previously herein. Results are reported in Table 4.

Results

TABLE 1

| Patient Samples Tested | | | | |
|---|---|---|---|---|
| | | | Expected Result | |
| Source | Samples | n | Positives | Negatives |
| CDC | CDC - Set 1 | 10 | 5 | 5 |
| CDC | CDC - Set 2 | 32 | 12 | 20 |
| Proficiency Samples | PT Samples | 20 | 9 | 11 |
| Proficiency Samples | Autoimmune(22 Reumatoid arthritis) | 42 | 0 | 42 |
| New York Biologics | Viruses | 46 | 0 | 46 |
| New York Biologics | RPR (+) | 28 | 0 | 28 |
| Total Samples | | 178 | 26 | 152 |

TABLE 2A

| Determination of Clinical Sensitivity | | | | | | | | | | | | | |
|---|---|---|---|---|---|---|---|---|---|---|---|---|---|
| | | Lyme WB (in-house) | | | Lyme WB (CDC) | | | Lyme IB (in-house) | | | Lyme IB (CDC) | | |
| Samples | Positives | IgM | IgG | G + M | IgM | IgG | G + M | IgM | IgG | G + M | IgM | IgG | G + M |
| CDC - Set 1 | 5 | 2 | 4 | 4 | 2 | 3 | 4 | 2 | 5 | 5 | 2 | 4 | 4 |
| CDC - Set 2 | 12 | 7 | 8 | 9 | 7 | 5 | 9 | 10 | 7 | 10 | 9 | 5 | 9 |
| PT Samples | 9 | 9 | 6 | 9 | 9 | 6 | 9 | 9 | 6 | 9 | 9 | 6 | 9 |
| Total Positives | 26 | 18 | 18 | 22 | 18 | 14 | 22 | 21 | 18 | 24 | 20 | 15 | 22 |
| Sensitivity | | 69.2% | 69.2% | 84.6% | 69.2% | 53.8% | 84.6% | 80.8% | 69.2% | 92.3% | 76.9% | 57.7% | 84.6% |

TABLE 2B

| Detailed Information on Lyme Positive Patients Samples (CDC Samples Panel 1 and 2 combined) | | | | | | | | | | | | | |
|---|---|---|---|---|---|---|---|---|---|---|---|---|---|
| | | Lyme WB (in-house) | | | Lyme WB (CDC) | | | Lyme IB (In-house) | | | Lyme IB (CDC) | | |
| CDC Samples | Positives | IgM | IgG | G + M | IgM | IgG | G + M | IgM | IgG | G + M | IgM | IgG | G + M |
| Early Lyme | 10 | 6 | 5 | 6 | 5 | 1 | 6 | 7 | 5 | 8 | 6 | 3 | 6 |
| Lyme Arthritis | 4 | 0 | 4 | 4 | 0 | 4 | 4 | 3 | 4 | 4 | 2 | 4 | 4 |
| Neurologic Lyme | 3 | 3 | 3 | 3 | 3 | 3 | 3 | 3 | 3 | 3 | 3 | 2 | 3 |
| Total Positives | 17 | 9 | 12 | 13 | 8 | 8 | 13 | 13 | 12 | 15 | 11 | 9 | 13 |
| Sensitivity | | 52.9% | 70.6% | 76.5% | 47.1% | 47.1% | 76.5% | 76.5% | 70.6% | 88.2% | 64.7% | 52.9% | 76.5% |

TABLE 3A

| Determination of Clinical Specificity | | | | | | | | | | | | | |
|---|---|---|---|---|---|---|---|---|---|---|---|---|---|
| | | Lyme WB (in-house) | | | Lyme WB CDC data (CDC) | | | Lyme IB (in-house) | | | Lyme IB (CDC) | | |
| Samples | Negatives | IgM | IgG | G + M | IgM | IgG | G + M | IgM | IgG | G + M | IgM | IgG | G + M |
| CDC - Set 1* | 5 | 0 | 1 | 1 | 0 | 0 | 0 | 0 | 0 | 0 | 0 | 0 | 0 |
| CDC - Set 2* | 20 | 0 | 1 | 1 | 0 | 0 | 0 | 3 | 1 | 4 | 0 | 0 | 0 |
| PT Samples | 11 | 0 | 0 | 0 | 0 | 0 | 0 | 0 | 0 | 0 | 0 | 0 | 0 |
| Autoimmune (22 RA) | 42 | 0 | 0 | 0 | 0 | 0 | 0 | 0 | 0 | 0 | 0 | 0 | 0 |
| Viruses (11 CMV) | 46 | 10 | 5 | 15 | 2 | 0 | 2 | 0 | 0 | 0 | 0 | 0 | 0 |
| RPR (+) | 28 | 6 | 3 | 7 | 1 | 0 | 1 | 0 | 1 | 1 | 0 | 0 | 0 |
| False Positives | | 16 | 10 | 24 | 3 | 0 | 3 | 3 | 2 | 5 | 0 | 0 | 0 |
| True Negatives | 152 | 136 | 142 | 128 | 149 | 152 | 149 | 149 | 150 | 147 | 152 | 152 | 152 |
| Specificity | | 89.5% | 93.4% | 84.2% | 98.0% | 100.0% | 98.0% | 98.0% | 98.7% | 96.7% | 100.0% | 100.0% | 100.0% |

*Western blot results provided by CDC

TABLE 3B

Detailed Summary of viral antibody positive samples

| | | Lyme WB (in-house) | | | Lyme WB (CDC) | | | Lyme IB (in-house) | | | Lyme IB (CDC) | | |
|---|---|---|---|---|---|---|---|---|---|---|---|---|---|
| Antibodies to | n | IgM | IgG | G + M | IgM | IgG | G + M | IgM | IgG | G + M | IgM | IgG | G + M |
| EBV | 24 | 6 | 4 | 10 | 2 | 0 | 2 | 0 | 0 | 0 | 0 | 0 | 0 |
| HSV | 7 | 2 | 0 | 2 | 0 | 0 | 0 | 0 | 0 | 0 | 0 | 0 | 0 |
| CMV | 11 | 0 | 1 | 1 | 0 | 0 | 0 | 0 | 0 | 0 | 0 | 0 | 0 |
| HCV | 4 | 9 | 0 | 2 | 0 | 0 | 0 | 0 | 0 | 0 | 0 | 0 | 0 |
| Viruses | 46 | 10 | 5 | 15 | 2 | 0 | 9 | 0 | 0 | 0 | 0 | 0 | 0 |
| Specificity | | 78.3% | 89.1% | 67.4% | 95.7% | 100.0% | 95.7% | 100.0% | 100.0% | 100.0% | 100.0% | 100.0% | 100.0% |

TABLE 3C

CDC Specificity Samples - Summary

| | | Lyme WB (in-house) | | | Lyme WB (CDC) | | | Lyme IB (in-house) | | | Lyme IB (CDC) | | |
|---|---|---|---|---|---|---|---|---|---|---|---|---|---|
| CDC Samples | Negatives | IgM | IgG | G + M | IgM | IgG | G + M | IgM | IgG | G + M | IgM | IgG | G + M |
| Fibromyalgia | 2 | 0 | 0 | 0 | 0 | 0 | 0 | 0 | 0 | 0 | 0 | 0 | 0 |
| Healthy endemic | 7 | 0 | 1 | 1 | 0 | 0 | 0 | 0 | 1 | 0 | 0 | 0 | 0 |
| Healthy non-endemic | 6 | 0 | 1 | 1 | 0 | 0 | 0 | 0 | 0 | 1 | 0 | 0 | 0 |
| Mononucelosis | 2 | 0 | 0 | 0 | 0 | 0 | 0 | 1 | 0 | 1 | 0 | 0 | 0 |
| MS | 2 | 0 | 0 | 0 | 0 | 0 | 0 | 0 | 0 | 0 | 0 | 0 | 0 |
| RA | 2 | 0 | 0 | 0 | 0 | 0 | 0 | 1 | 0 | 1 | 0 | 0 | 0 |
| Severe Peridontitis | 2 | 0 | 0 | 0 | 0 | 0 | 0 | 1 | 0 | 1 | 0 | 0 | 0 |
| Syphilis | 2 | 0 | 0 | 0 | 0 | 0 | 0 | 0 | 0 | 0 | 0 | 0 | 0 |
| False Positives | | 0 | 2 | 2 | 0 | 0 | 0 | 3 | 1 | 4 | 0 | 0 | 0 |
| True Negatives | 25 | 25 | 23 | 23 | 0 | 0 | 0 | 22 | 2 | 21 | 0 | 0 | 0 |
| Specificity | | 100.0% | 92.0% | 92.0% | 0.0% | 0.0% | 0.0% | 88.0% | 8.0% | 84.0% | 0.0% | 0.0% | 0.0% |

Western blot results provided by CDC

As shown in Table 1, 14/42 patients (33%) in the Bbsl group had antibodies to Bbss based on reactivity with Bbss-specific antigens derived from the B31 and/or 297 strains. Four had antibodies to Bbss only, while the remaining ten patients reacted with Bbss and other Bbsl species. In five samples (8, 12, 51, 86, and 88) the signal intensity with multiple species including Bbss was strong. In the remaining five samples (22, 31, 52, 63, and 64) the signal with other Bbsl species was much stronger than Bbss.

The results obtained with the 175 control sera that were expected to be negative for Bbsl and TBRF yielded a false positive rate of 2.3% (4/175 samples) for the Bbsl immunoblot and 2.7% (5/175 samples) for the TBRF immunoblot (Table 3). False positive tests for Bbsl were seen with a healthy endemic serum (one control), viral infection (one control) and syphilis (two controls). False positive tests for TBRF were seen with an allergy patient serum (one control), multiple sclerosis (one control), viral infection (one control) and syphilis (two controls).

Based on the data shown in Table 1, Table 2A-B, and Tables 3A-C, the sensitivity of the Lyme ImmunoBlot is 92.3%, and the specificity is 98% for IgM and 98.7% for IgG. Interestingly, all 3 patients with false positive IgM results—one with mononucleosis, one with rheumatoid arthritis, and one with severe periodontitis—had antibodies to Osp C (23 kDa) and Osp A (31 kDa), whereas none of the 11 patients positive for antibodies to CMV or the 22 patients with rheumatoid arthritis were negative on the Lyme ImmunoBlot IgM. Thus it is possible that these three patients could have been exposed to *B. burgdorferi* but did not have active disease. Based on the data obtained in this study, Lyme ImmunoBlots can be used in place of Lyme Western Blots.

FIG. 3 shows ImmunoBlots of representative patient serum samples and interpreted according to in-house criteria. These results illustrate how detection of antigens from multiple Bbsl species identifies patients that would otherwise be missed by only testing for Bbss antigens.

TABLE 4

Summary of seroreactivity for CLD cohort subjects in Group 1 (Bbsl), Group 2 (TBRF) or both

| ImmunoBlot | Total |
|---|---|
| Group 1 (*B. burgdorferi* sensu lato Positive) | 42 |
| Group 2 (Tiek-Borae Relapsing Fever *Borrelia* Positive) | 56 |
| Dual Group 1 and 2 Positive | 8 |
| Group 1 Bbsl Positive Samples | 34 (38%) |
| *B. bugdorferi* sensu lato | 8 |
| BB sensu stricto (B31 and/or B297) | 4 |
| *B. afzelii/garinii* | 6 |
| *B. californiensis* | 6 |
| *B. spielmanii* | 6 |
| *B. mayonii* + *B. speilmanii* | 2 |
| *B. spielmanii* + *B. afzelii/garinii* | 1 |
| *B. afzelii/garinii*, *B. californiensis*, *B. mayonii* | 1 |
| Dual Group 1 and 2 | 8 (9%) |
| *B. burgdorferi* sensu lato + Tick-Borne Relapsing Fever *borrelia* | 2 |
| *B. burgdorferi* sensu lato + *B. hermsii* | 1 |
| *B. californiensis* + Tick-Borne Relapsing Fever *borrelia* | 2 |
| *B. spielmanii* + Tick-Borne Relapsing Fever *borrelia* | 1 |

TABLE 4-continued

| Summary of seroreactivity for CLD cohort subjects in Group 1 (Bbsl), Group 2 (TBRF) or both | |
|---|---|
| ImmunoBlot | Total |
| *B. afzelii/garinii* + Tick-Borne Relapsing Fever *borrelia* | 1 |
| *B. afzelii/garinii* + *B. turicatae* | 1 |

In the CLD cohort (Table 4), ImmunoBlot testing revealed that out of the 90 subjects with suspected LD, a total of 42 patients (47%) were seropositive for Bbsl (Group 1). Seroreactivity within Group 1 was as follows: Bbss (14), *B. californiensis* (8), *B. spielmanii* (10), *B. afzelii/B. garinii* (10), and mixed infections that included *B. mayonii* (3). Thirty-four patients (38%) were seropositive for Bbsl alone, 48 patients (53%) were seropositive for TBRF alone, and 8 patients (9%) were positive for both Bbsl and TBRF. Sera from 4 patients in Group 1 were seropositive for 2 or more species of Bbsl. Seroreactivity to the exact *Borrelia* species in the remaining Group 1 and Group 2 patients could not be defined using the immunoblot technique.

Forty-eight patients were positive for *B. burgdorferi*-specific antibodies. In contrast, if only *B. burgdorferi* sensu stricto (B31 and 297) were used as antigens, only 14 patients would be identified as positive. This data demonstrates that antigens from multiple species are required for an inclusive test.

Discussion

Using the Lyme ImmunoBlot test described Examples 1 and 2, this study of patients who met the CLD case definition revealed that all had exposure to either Bb or TBRF species. Positive immunoblots were further characterized at the species level for the following Bbsl: *B. californiensis, B. spielmanii, B. afzelii/B. garinii*, and *B. mayonii*. Most sera were reactive to either Bb species alone (38%) or to TBRF species alone (53%), with few seropositive to both Bb species and TBRF species (9%). The lack of widespread dual reactivity suggests that cross-reactivity in our immunoblots between TBRF and Bb species is unlikely. Immunoblot testing of control sera demonstrated excellent specificities of 97.7% for the Bbsl assay and 97.1% for the TBRF assay (Table 3).

Spirochetes falling into the Bbsl complex are distributed worldwide, with most cases reported in the USA, Europe, and Asia. The CDC states that approximately 30,000 cases of LD are reported in the USA each year using surveillance criteria featuring two-tier Bbss testing, but when tracked by other methods it is estimated that more than 300,000 people develop LD in the USA annually. The fact that CDC surveillance criteria featuring two-tier Bbss testing captures less than one out of every ten cases shows that LD is underreported, and the results of our study suggest that some people with suspected LD who have failed to meet surveillance criteria may be infected by Bbsl that are not crossreactive with Bbss on two-tier testing.

The immunoblot testing used in this study enabled differentiation of Bbsl into 5 specific categories: *B. californiensis, B. spielmanii, B. mayonii*, the European species *B. afzelii/B. garinii*, and undifferentiated Bb species Based on surveillance reporting in the USA, the distribution pattern of Bbss is characterized by human cases reported in all 50 states with the majority reported in the Northeast, upper Midwest and northern California. Importantly, however, other Bbsl species are not detected by commercial testing in the USA. Until recently, Bbss, *B. garinii* and *B. afzelii* were considered to be the only etiologic agents of LD. Currently, nine species are said to have pathogenic potential: *B. afzelii, B. bavariensis, B. bissettii*, Bbss, *B. garinii, B. kurtenbachii, B. lusitaniae, B. spielmanii* and *B. valaisiana*. Nine other species including *B. californiensis* have not been isolated from humans. *B. afzelii, B. garinii* and *B. spielmanii* are considered to be *Borrelia* species primarily found in Eurasia, while *B. californiensis* is considered to be a North American species. The understanding in the art of the pathogenicity of *Borrelia* species is evolving, and some species that have not been isolated from humans and are not considered to be pathogenic may be capable of causing illness.

The genetic diversity of *Borrelia* spirochetes, and the symptoms of infection that are as diverse as the organisms causing them, makes it challenging to diagnose *Borrelia*-associated disease. It is important to recognize that classification is a human concept and the organisms encompassing the genus *Borrelia* fall within a. continuous spectrum of organisms rather than into well-defined genetically-distinct groups that are easily categorized.

This study highlights the dire need for a diagnostic approach that acknowledges the complexity and genetic diversity of *Borrelia* spirochetes. Commercially available serological testing kits, as endorsed by the CDC, are highly specific for Bbss, and have poor sensitivity. The CDC case definition for LD is narrowly drawn and the laboratory criteria needed to qualify as a positive case are rigid. Commercial serological tests are based on antigens of just one Bbss strain, B31, and this test protocol is therefore not capable of detecting antibody reactivity to *Borrelia* species and strains that lack crossreactivity with B31—a limitation that excludes detection of many *Borrelia* pathogens.

Microscopy is nonspecific: spirochetes are only visible when there are high bacterial loads in the blood, and artifacts such as pseudospirochetes (filaments derived from erythrocytes) can be mistaken for spirochetes. Ideally, a microscopic diagnosis should be confirmed by testing using other methodologies such as serological assays. In contrast, the immunoblot testing described herein detected exposure to a variety of Bbsl species.

Bb-seropositive patients tended to be more frequently IgM positive than IgG or dual IgM/IgG positive. Prolonged IgM reactivity has been demonstrated in patients with late or longstanding LD. Furthermore, IgM reactivity has been demonstrated in human subjects with persistent Bb infection despite treatment with antibiotics. The cohort studied herein met the case description for CLD and had symptoms consistent with LD and other tickborne co-infections, such as musculoskeletal, neuropsychiatric and/or cardiac manifestations. The instant study corroborates the findings of previous studies showing that prolonged IgM reactivity is associated with Bb infections and suggests that these infections may be persistent. The fact that IgM reactivity in *Borrelia* infections is likely to persist long after the onset of symptoms should be recognized when designing testing protocols for diagnosis.

In summary, exposure to Bbsl is a cause for concern, and Bbsl may explain LD symptoms in patients who are seronegative for Bbss. Some patients may demonstrate dual exposure to both Bb and TBRF species, further complicating diagnosis and treatment. Immunoblot testing for Bbsl has allowed the detection of a diverse group of *Borreila* serotypes and has provided a greater understanding of human exposure to pathogenic *Borrelia.*

Example 3. Lyme IGXSpot Test

IGXSpot is an enzyme-linked immunosorbent spot (ELISPOT) based assay used for monitoring cellular immune responses. ELISPOT assay is highly sensitive and accurate in detecting rare antigen-specific T cells [Jin et al., *Cells* (2013) 2:607-620].

Methods

IGXSpot Lyme Disease (LD) test uses the following *B. burgdorferi* sensu lato species-specific antigens (mixture of Osp A, Osp B, Osp C, P39, P41, P93, C6 (SEQ ID NO: 45), and VslE (SEQ ID NO: 44)) to stimulate T cells isolated from patient whole blood that are cultured inside each well of the 96-well plates. If the patient has recently been infected by *B. burgdorferi*, isolated patient T cells will respond to the stimulation by secreting Interferon gamma (IFNγ). IFNγ is captured at the bottom of the well and detected by biotinylated IFNγ antibody bound to streptavidin conjugated alkaline phosphatase (AP). When the substrate of AP is added to each well, bright blue dots will appear if IFNγ is present. Any patient sample with 3 or more blue dots is considered positive. The number of blue dots therefore represents the likelihood of the patient being infected by *B. burgdorferi* sensu lato.

Patient Sample Collection and Preparation

A set of 97 blood samples from patients with Lyme-like symptoms were collected in sodium heparin tubes. All the blood samples were processed as per Lyme IGXSpot procedure [Jin et al., *Cells* (2013) 2:607-620]. In addition, serum samples from all patients were tested by IgM and IgG Western blots. Detailed results are presented in Tables 5 and 6.

Results

TABLE 5

IgXSpot Lyme Test Data Summary

| Critiera | Lyme IGXSpot | Lyme Positive WB/PCR/IFA | Lyme WB IgM | Lyme WB IgG |
|---|---|---|---|---|
| IGXSpot Pos. | 22 | 10 | 6 | 1 |
| IGXSpot Neg. | 75 | 45 | 21 | 14 |
| WB/PCR/EFA & IGXSpot Neg. (Total 30 Samples) | 0 | 0 | 0 | 0 |
| 14 All tests Negative Samples (Normal Samples) | 0 | 0 | 0 | 0 |
| Sensitivity | | 18.2% | | |
| Specificity | | 100.0% | | |

TABLE 6

22 IGXSpot Positives

| | n | PCR (+) | WB (+) | Band 31 | Band 23 | Band 23, 31 |
|---|---|---|---|---|---|---|
| WB - IgM | 6 | 1 | 6 | 5 | 2 | 2 |
| WB - IgG | 1 | 0 | 1 | 1 | 0 | 0 |
| PCR | 3 | 3 | 0 | 2 | 1 | 0 |
| WB & PCR (−) | 12 | 0 | 0 | 3 | 2 | 0 |
| Total | 22 | 4 | 7 | 11 | 5 | 2 |

As shown in Table 5, 22/97 samples were positive by IGXSpot. This included one positive by Western blot and PCR (Table 5), 6 positive by Western blot only, and 3 positive by PCR. The remaining 12 samples were negative by both Western blot and PCR. Interestingly, Band 31 was present in 11/22 patients tested. This included 6 Western blot positive samples, 1 Western blot and PCR positive sample, 2 PCR positive samples and 3 Western blot and PCR negative patients samples. Five samples were positive for band 23; 2 also had band 31 present.

Of the remaining 44 Lyme negative samples, 9 samples had antibodies to other tick-borne pathogens. This included 5 with antibodies to *B. duncani;* 2 with antibodies to *Analplasma phagocytophilum;* 1 with antibodies to *Ehrlichia chaffeenssis* and 1 with antibodies to *Rickettssia.*

Based on these data, of the 55 patients positive by other tests, 10 patients (18.2%) were positive by IGXSpot. The remaining 12 patients positive by IGXSpot were negative by all other tests. Of those 12 patients, 3 had band 31 kDa present on their Western blot and 2 had band 23 kDA present on the Western blot. If these are considered true positives, then IGXSpot sensitivity is 23.8%. An additional 7 patients were positive by IgXSpot. All 44 patients negative for Lyme disease were negative by IGXSpot test. Thus the specificity was 100%. These data suggest that IGXSpot is positive in patients with late disease, who produce very low antibody levels or no antibodies. Therefore, the IGXSpot may identify patients missed by other tests.

Example 4. Lyme ImmunoBLOT Validation Study with Blinded CDC Samples

A set of 280 blinded serum samples were provided by CDC. Of these 90 were from patients confirmed positive for infection with *Borrelai burgdorferi* group. The remaining 190 were from non-Lyme patients. All samples were tested by Lyme ImmunoBlots IgM and IgG to determine clinical sensitivity and specificity.

Methods

Recombinant proteins derived from several US and European species of Bbsl were used to prepare antigen strips for Lyme IBs. The recombinant proteins selected included all the proteins used in scoring WBs by the CDC and in-house criteria described below. P23 (OspC) and P31 (OspA) proteins from several different BBsl species were used as target antigens in the Lyme IB. Separate P39 (BmpA) antigens derived from European and US Bbsl species were included in the panel of test antigens. Additionally, a hybrid protein containing the immunodominant region of VslE from different Bbsl species referred to elsewhere herein as C6 (SEQ ID NO: 45) and also termed "Tier 1 antigen" was used in the Lyme IBs as a target antigen. Recombinant antigens were prepared by cloning the hybrid gene constructs or portions of the selected genes into pET vectors, and then expressing the proteins in *Escherichia coli* (GenScript, Piscataway, NJ, USA). The *E. coli*-produced recombinant Bbsl proteins were then purified using metal affinity chromatography followed by gel filtration. All the recombinant proteins were >90% pure by Coomassie blue staining after SDS PAGE.

Preparation of Lyme ImmunoBlot Strips

Purified proteins and two control proteins, diluted to yield 7-19 ng of protein as a line in each 3 mm strip of membrane were sprayed in straight lines onto nitrocellulose membrane (Amersham Protran, GE Healthcare Life Science) using a BioDot liquid dispenser (BioDot, Irvine, CA). The two control proteins were Protein L (Sigma, St. Louis, MO) for detecting the addition of human serum (termed serum control), and a mixture of human IgM and IgG (Sigma, St. Louis, MO) for detecting the addition of alkaline phosphatase conjugated anti-human antibodies (termed conjugate control). The membranes were then blocked with 5% non-fat dry milk and sliced into 3 mm wide strips.

Procedure for Detection of *Borrelia* Specific Antibodies on Lyme Immunoblots and Western Blots with Test Sera Prior to use, each strip was labeled and then soaked in 1 mL of diluent (100 mM Tris, 0.9% NaCl, 0.1% Tween-20 and 1% non-fat dry milk) for 5 min in a trough. A 10 μL aliquot of the test or control serum was added to a corresponding IB or WB strip in the trough. The strips were then incubated at room temperature for one hour with serum, followed by three washes with wash buffer (KPL, Gaithersburg, MD, USA) at room temperature. After aspirating the final wash solution, strips for detecting IgG and IgM were incubated with alkaline phosphatase-conjugated goat anti-human IgG at 1:10,000 dilution and IgM at 1:6000 dilution respectively (KPL, Gaithersburg, MD, USA) for one hour. After three washes, bands were visualized by reaction with 5-bromo-4-chloro-3-indolylphosphatenitro-blue tetrazolium (BCIP/NBT, KPL, Gaithersburg, MD, USA). The reactions were terminated by washing with distilled water when a calibration control produced a visible band at 39 kDa. Alkaline phosphatase-conjugated rabbit antibody to the 39/93 kDa. BBsl antigens (Strategic Biosciences, Stow, MA, USA) diluted in human serum was used as the calibration control as previously described. Bands with lower intensity than the calibration control were reported as negative. The Lyme IB strips were also reacted with a mixture of human sera from patients with confirmed Lyme disease as a positive control and sera from uninfected persons as a negative control.

Scoring and Interpretation of Positive Serological Reactions

The following antigen bands in kDa were scored on the Lyme IB strips: for IgG—C6/Tier 1 antigen (SEQ ID NO: 45), 18 (group (xii) SEQ ID NO: 43), 23 (OspC; group (i) SEQ ID NOs: 1-10), 28 (group (xi) SEQ ID NOs: 41 and 42), 30 (group (x) SEQ ID NO: 40), 31 (OspA; group (v) SEQ ID NOs: 11-20), 34 (OspB, group (vi) SEQ ID NOs: 34-39), 39 (BmpA, group (ii) SEQ ID NOs: 21-26), 41 (FlaB; group (iii) SEQ ID NOs: 32 and 33), 45 (group (ix) SEQ ID NO: 31), 58 (group (viii) SEQ ID NO: 30), 66 (group (vii) SEQ ID NO: 29), and 93 (group (iv) SEQ ID NOs: 27 and 28); for IgM—C6/Tier 1 antigen (SEQ ID NO: 45), 23 (OspC; group (i) SEQ ID NOs: 1-10), 31 (Osp A; group (v) SEQ ID NOs: 11-20), 34 (OspB; group (vi) SEQ ID NOs: 34-39), 39 (BmpA; group (ii) SEQ ID NOs: 21-26), 41 (FlaB; group (iii) SEQ ID NOs: 32 and 33), and 93 (group (iv) SEQ ID NOs: 27 and 28). Tier 1 scoring: the sample was considered positive for Tier 1 if either IgM or IgG IB had a positive Tier-1 antigen band. Tier 2 scoring: IgG was considered positive if two from the following six antigens bands were present: 23, 31, 34, 39, 41 and 93 kDa. IgM IB was considered positive if two out of the five following bands were present: 23, 31, 34, 39 and 41 kDa. Results are summarized in Tables 7 and 8.

A sample was considered two-tier IgM-positive if positive by Tier 1 and IgM-positive by Tier 2. A sample was considered two-tier IgG positive if positive by Tier 1 and IgG-positive by Tier 2. A sample was considered two-tier IgM and IgG positive if positive by Tier 1 and IgM and IgG positive by Tier 2.

Results and Discussion

As shown in Tables 7 and 8, using the two-tier scoring criteria described above herein, the sensitivity of Lyme IgM immunoblot was 78.9%; the sensitivity of Lyme IgG immunoblot 65.6%; and the overall sensitivity, 88.9%. The specificity was 97.9% for IgM; 100% for IgG; and 97.9% overall.

TABLE 7

Sensitivity of two-tier Lyme ImmunoBlot IgM and IgG (N = 90)

| Disease | N | IgM | IgG | IgM and IgG | Overall |
|---|---|---|---|---|---|
| Early Lyme | 60 | 21 | 4 | 27 | 52 |
| Cardiac Lyme | 3 | 0 | 0 | 2 | 2 |

TABLE 7-continued

Sensitivity of two-tier Lyme ImmunoBlot IgM and IgG (N = 90)

| Disease | N | IgM | IgG | IgM and IgG | Overall |
|---|---|---|---|---|---|
| Lyme arthritis | 20 | 0 | 5 | 15 | 20 |
| Lyme arthritis | 7 | 0 | 0 | 6 | 6 |
| Total Lyme (+) | 90 | 21 | 9 | 50 | 80 |
| Total Lyme (+) | 90 | 71 | 59 | | 80 |
| Sensitivity | | 78.9% | 65.6% | | 88.9% |

TABLE 8

Specificity of two-tier Lyme ImmunoBlot IgM and IgG (N = 190)

| Disease | N | IgM | IgG | IgM and IgG | Overall |
|---|---|---|---|---|---|
| Fibromyalgia | 15 | 1 | 0 | 0 | 1 |
| Mononucleosis | 15 | 0 | 0 | 0 | 0 |
| Multiple sclerosis | 15 | 0 | 0 | 0 | 0 |
| Periodontitis | 15 | 0 | 0 | 0 | 0 |
| Rheumatoid arthritis | 15 | 1 | 0 | 0 | 1 |
| Syphilis | 15 | 1 | 0 | 0 | 1 |
| Endemic Negative Controls | 50 | 0 | 0 | 0 | 0 |
| Non-Endemic Negative Controls | 50 | 1 | 0 | 0 | 1 |
| False Positive | 0 | 4 | 0 | 0 | 4 |
| True Negative | 190 | 186 | 190 | 190 | 186 |
| Specificity | | 97.9% | 100.0% | 100% | 97.9% |

Conclusion

Based on the data presented, two-tier Lyme ImmunoBlots have the sensitivity and specificity for clinical use, for detection of *B. burgdorferi* sensu lato antibodies in patients' sera.

Equivalents

Although several aspects of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific aspects of the disclosure described herein. It is, therefore, to be understood that the foregoing aspects are presented by way of example only and that, within the scope of the appended claims and equivalents thereto; the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A panel for detecting IgM- or IgG-class antibodies, the panel comprising:

a C6 chimera consisting of SEQ ID NO: 45; and a plurality of groups of labelled and/or tagged and/or bound amino acid sequences, wherein labelled and/or tagged amino acid sequence is labelled and/or tagged with a detectable moiety, and wherein the plurality of groups of labelled and/or tagged and/or bound amino acid sequences is selected from the following groups:

(i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, (ii) SEQ ID NO: 21, SEQ ID NO: 22, SEQ ID NO: 23, SEQ ID NO: 24, SEQ ID NO: 25, and SEQ ID NO: 26, (iii) SEQ ID NO: 32 and SEQ ID NO: 33, (iv) SEQ ID NO: 27 and SEQ ID NO: 28;

(v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20, (vi) SEQ ID NO: 34, SEQ ID NO: 35, SEQ ID NO: 36, SEQ ID NO: 37, SEQ ID NO: 38, and SEQ ID NO: 39, (vii) SEQ ID NO: 29, (viii) SEQ ID NO: 30, (ix) SEQ ID NO: 31, (x) SEQ ID NO: 40, (xi) SEQ ID NOs: 41 and 42, and (xii) SEQ ID NO: 43.

2. The panel of claim 1, wherein the labelled and/or tagged and/or bound amino acid sequences are bound to a substance selected from the group consisting of nitrocellulose, nylon, polyvinylidene difluoride (PVDF), magnetic beads, and agarose.

3. The panel of claim 1 further comprising one or more of SEQ ID NO: 44 and SEQ ID NO: 46.

4. The panel of claim 1, wherein each of the one or more amino acid sequences are tagged with an antibody with specificity for the amino acid sequence.

5. A method for detecting IgM- or IgG-class antibodies resulting from infection by one or more *Borrelia burgdorferi* sensu lato (Bbsl) species, if present in a biological sample obtained from a subject suspected of having Lyme disease, the method comprising:

(a) providing a screening panel comprising:

a C6 chimera consisting of SEQ ID NO: 45; and a plurality of groups of labelled and/or tagged and/or bound amino acid sequences, wherein the plurality of groups of labelled and/or tagged and/or bound amino acid sequences is selected from the following groups:

(i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, (ii) SEQ ID NO: 21, SEQ ID NO: 22, SEQ ID NO: 23, SEQ ID NO: 24, SEQ ID NO: 25, and SEQ ID NO: 26, (iii) SEQ ID NO: 32 and SEQ ID NO: 33, (iv) SEQ ID NO: 27 and SEQ ID NO: 28;

(v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20, (vi) SEQ ID NO: 34, SEQ ID NO: 35, SEQ ID NO: 36, SEQ ID NO: 37, SEQ ID NO: 38, and SEQ ID NO: 39, (vii) SEQ ID NO: 29, (viii) SEQ ID NO: 30, (ix) SEQ ID NO: 31, (x) SEQ ID NO: 40, (xi) SEQ ID NOs: 41 and 42, and (xii) SEQ ID NO: 43;

(b) providing the biological sample obtained from the subject suspected of having Lyme disease;

(c) contacting the biological sample with the screening panel of step (a) under conditions appropriate for specific antibody binding to an epitope; and (d) detecting specific binding of IgM- or IgG-class antibodies, if present in the biological sample, with amino acid sequences included in the selected groups of the screening panel of step (a), wherein the sample is scored as positive for infection by one or more Bbsl species when:

(1) a positive immunobinding reaction with IgM-class antibodies is detected for SEQ ID NO: 45 and for at least one amino acid sequence from at least two of groups (i)-(iii), (2) a positive immunobinding reaction with IgG-class antibodies is detected for SEQ ID NO: 45 and for at least one amino acid sequence from at least five of groups (i)-(iv) and (vii)-(xii), (3) a positive immunobinding reaction with IgM-class antibodies is detected for SEQ ID NO: 45 and for at least one amino acid sequence from at least two of groups (i)-(iii) and (v), or (4) a positive immunobinding reaction with IgG-class antibodies is detected for SEQ ID NO: 45 and for at least one amino acid sequence from at least two of groups (i)-(vi), and wherein a positive score for infection indicates the presence of antibodies to one or more Bbsl species in the subject.

6. The method of claim 5 wherein the binding of IgM-class antibodies is detected through the use of an anti-human IgM antibody linked to a detectable moiety.

7. The method of claim 5 wherein the binding of IgG-class antibodies is detected through the use of an anti-human IgG antibody linked to a detectable moiety.

8. The method of claim 6 or 7, wherein the detectable moiety is selected from the group consisting of chromophores, radioactive moieties, and enzymes.

9. The method of claim 8, wherein the detectable moiety comprises alkaline phosphatase.

10. The method of claim 8, wherein the detectable moiety comprises biotin.

11. The method of claim 5, wherein the one or more Bbsl species comprise *B. afzelii, B. garinii, B. californiensis, B. spielmanii, B. mayonii, B. valaisiana, B. bavariensis, B. burgdorferi* B31, and *B. burgdorferi* 297.

12. The method of claim 5, wherein the screening panel of step (a) further comprises at least one or more of SEQ ID NO: 44 and SEQ ID NO: 46.

13. A method for detecting IgM-class and IgG-class antibodies resulting from infection by one or more *Borrelia burgdorferi* sensu lato (Bbsl) species, if present in a biological sample obtained from a subject suspected of having Lyme disease, the method comprising:

(a) providing a screening panel comprising:
a C6 chimera consisting of SEQ ID NO: 45; and
a plurality of groups of labelled and/or tagged and/or bound amino acid sequences, wherein the plurality of groups of labelled and/or tagged and/or bound amino acid sequences is selected from the following groups:
(i) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10,
(ii) SEQ ID NO: 21, SEQ ID NO: 22, SEQ ID NO: 23, SEQ ID NO: 24, SEQ ID NO: 25, and SEQ ID NO: 26,
(iii) SEQ ID NO: 32 and SEQ ID NO: 33,
(iv) SEQ ID NO: 27 and SEQ ID NO: 28;
(v) SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20,
(vi) SEQ ID NO: 34, SEQ ID NO: 35, SEQ ID NO: 36, SEQ ID NO: 37, SEQ ID NO: 38, and SEQ ID NO: 39,
(vii) SEQ ID NO: 29,
(viii) SEQ ID NO: 30,
(ix) SEQ ID NO: 31,
(x) SEQ ID NO: 40,
(xi) SEQ ID NOs: 41 and 42, and
(xii) SEQ ID NO: 43;
(b) providing the biological sample obtained from the subject suspected of having Lyme disease;
(c) contacting the biological sample with the screening panel of step (a) under conditions appropriate for specific antibody binding to an epitope; and
(d) detecting specific binding of IgM-class and IgG-class antibodies, if present in the biological sample, with amino acid sequences included in the selected groups of the screening panel of step (a), wherein the sample is scored as positive for infection by one or more Bbsl species when a positive immunobinding reaction with IgM-class or IgG-class antibodies is detected for SEQ ID NO: 45 and:
(1) (A) a positive immunobinding reaction with IgM-class antibodies is detected for at least one amino acid sequence from at least two of groups (i)-(iii), and
(1) (B) a positive immunobinding reaction with IgG-class antibodies is detected for at least one amino acid sequence from at least five of groups (i)-(iv) and (vii)-(xii); or
(2) (A) a positive immunobinding reaction with IgM-class antibodies is detected for at least one amino acid sequence from at least two of groups (i)-(v), and
(2) (B) a positive immunobinding reaction with IgG-class antibodies is detected for at least one amino acid sequence from at least two of groups (i)-(vi),
and wherein a positive score for infection indicates the presence of antibodies to one or more Bbsl species in the subject.

14. The method of claim 13 wherein the binding of IgM-class antibodies is detected through the use of an anti-human IgM antibody linked to a detectable moiety.

15. The method of claim 13 wherein the binding of IgG-class antibodies is detected through the use of an anti-human IgG antibody linked to a detectable moiety.

16. The method of claim 14 or 15, wherein the detectable moiety is selected from the group consisting of chromophores, radioactive moieties, and enzymes.

17. The method of claim 16, wherein the detectable moiety comprises alkaline phosphatase.

18. The method of claim 16, wherein the detectable moiety comprises biotin.

19. The method of claim 13, wherein the one or more Bbsl species comprise *B. afzelii, B. garinii, B. californiensis, B. spielmanii, B. mayonii, B. valaisiana, B. bavariensis, B. burgdorferi* B31, and *B. burgdorferi* 297.

20. The method of claim 13, wherein the screening panel of step (a) further comprises at least one or more of SEQ ID NO: 44 and SEQ ID NO: 46.

* * * * *

SEQUENCE LISTING

```
<160> NUMBER OF SEQ ID NOS: 73

<210> SEQ ID NO 1
<211> LENGTH: 198
<212> TYPE: PRT
<213> ORGANISM: Borrelia burgdorferi B31

<400> SEQUENCE: 1

Met Phe Leu Phe Ile Ser Cys Asn Asn Ser Gly Lys Asp Gly Asn Thr
1               5                   10                  15

Ser Ala Asn Ser Ala Asp Glu Ser Val Lys Gly Pro Asn Leu Thr Glu
            20                  25                  30

Ile Ser Lys Lys Ile Thr Asp Ser Asn Ala Val Leu Leu Ala Val Lys
        35                  40                  45

Glu Val Glu Ala Leu Leu Ser Ser Ile Asp Glu Ile Ala Ala Lys Ala
    50                  55                  60

Ile Gly Lys Lys Ile His Gln Asn Asn Gly Leu Asp Thr Glu Asn Asn
65                  70                  75                  80

His Asn Gly Ser Leu Leu Ala Gly Ala Tyr Ala Ile Ser Thr Leu Ile
                85                  90                  95

Lys Gln Lys Leu Asp Gly Leu Lys Asn Glu Gly Leu Lys Glu Lys Ile
            100                 105                 110

Asp Ala Ala Lys Lys Cys Ser Glu Thr Phe Thr Asn Lys Leu Lys Glu
        115                 120                 125

Lys His Thr Asp Leu Gly Lys Glu Gly Val Thr Asp Ala Asp Ala Lys
    130                 135                 140

Glu Ala Ile Leu Lys Thr Asn Gly Thr Lys Thr Lys Gly Ala Glu Glu
145                 150                 155                 160

Leu Gly Lys Leu Phe Glu Ser Val Glu Val Leu Ser Lys Ala Ala Lys
                165                 170                 175

Glu Met Leu Ala Asn Ser Val Lys Glu Leu Thr Ser Pro Val Val Ala
            180                 185                 190

Glu Ser Pro Lys Lys Pro
        195


<210> SEQ ID NO 2
<211> LENGTH: 204
<212> TYPE: PRT
<213> ORGANISM: Borrelia burgdorferi 297

<400> SEQUENCE: 2

Met Phe Leu Phe Ile Ser Cys Asn Asn Ser Gly Lys Asp Gly Asn Thr
1               5                   10                  15

Ser Ala Asn Ser Ala Asp Glu Ser Val Lys Gly Pro Asn Leu Thr Glu
            20                  25                  30

Ile Ser Lys Lys Ile Thr Glu Ser Asn Ala Val Val Leu Ala Val Lys
        35                  40                  45

Glu Val Glu Thr Leu Leu Thr Ser Ile Asp Glu Leu Ala Lys Ala Ile
```

```
    50                  55                  60

Gly Lys Lys Ile Lys Asn Asp Val Ser Leu Asp Asn Glu Ala Asp His
65                  70                  75                  80

Asn Gly Ser Leu Ile Ser Gly Ala Tyr Leu Ile Ser Thr Leu Ile Thr
                85                  90                  95

Lys Lys Ile Ser Ala Ile Lys Asp Ser Gly Glu Leu Lys Ala Glu Ile
            100                 105                 110

Glu Lys Ala Lys Lys Cys Ser Glu Glu Phe Thr Ala Lys Leu Lys Gly
        115                 120                 125

Glu His Thr Asp Leu Gly Lys Glu Gly Val Thr Asp Asp Asn Ala Lys
    130                 135                 140

Lys Ala Ile Leu Lys Thr Asn Asn Asp Lys Thr Lys Gly Ala Asp Glu
145                 150                 155                 160

Leu Glu Lys Leu Phe Glu Ser Val Lys Asn Leu Ser Lys Ala Ala Lys
                165                 170                 175

Glu Met Leu Thr Asn Ser Val Lys Glu Leu Thr Ser Pro Val Val Ala
            180                 185                 190

Glu Ser Pro Lys Asn Pro Gly Ser Val Asp Lys Leu
        195                 200


<210> SEQ ID NO 3
<211> LENGTH: 200
<212> TYPE: PRT
<213> ORGANISM: Borrelia bissettii

<400> SEQUENCE: 3

Met Phe Leu Phe Ile Ser Cys Asn Asn Ser Gly Lys Asp Gly Asn Ser
1               5                   10                  15

Ala Ser Thr Asn Pro Ala Asp Glu Ser Ala Lys Gly Pro Asn Leu Thr
            20                  25                  30

Glu Ile Ser Lys Lys Ile Thr Asp Ser Asn Ala Ile Val Leu Ala Val
        35                  40                  45

Lys Glu Val Glu Thr Leu Leu Leu Ser Ile Asp Glu Leu Ala Lys Ala
    50                  55                  60

Ile Gly Lys Lys Ile Asn Asn Asn Gly Leu Asp Val Leu Gln Asn Phe
65                  70                  75                  80

Asn Ala Ser Leu Leu Gly Gly Ala His Thr Ile Ser Lys Leu Ile Thr
                85                  90                  95

Glu Lys Leu Ser Lys Leu Asn Gly Ser Glu Glu Leu Lys Glu Lys Ile
            100                 105                 110

Glu Ala Ala Lys Lys Cys Ser Asp Asp Phe Thr Lys Lys Leu Gln Ser
        115                 120                 125

Ser His Ala Glu Leu Gly Val Ala Gly Gly Ala Thr Thr Asp Glu Asn
    130                 135                 140

Ala Lys Lys Ala Ile Leu Lys Ser Asn Ala Asp Lys Thr Lys Gly Ala
145                 150                 155                 160

Asp Glu Leu Gly Lys Leu Phe Glu Ser Val Glu Ser Leu Ala Lys Ala
                165                 170                 175

Ala Lys Glu Met Leu Ala Asn Ser Val Lys Glu Leu Thr Ser Pro Val
            180                 185                 190

Val Ala Glu Thr Pro Lys Lys Pro
        195                 200


<210> SEQ ID NO 4
<211> LENGTH: 205
```

<212> TYPE: PRT
<213> ORGANISM: Borrelia californiensis

<400> SEQUENCE: 4

```
Met Phe Leu Phe Ile Ser Cys Asn Asn Ser Gly Lys Asp Gly Asn Ser
1               5                   10                  15

Ala Ser Thr Asn Pro Ala Asp Glu Ser Lys Gly Pro Asn Leu Thr Glu
            20                  25                  30

Ile Ser Lys Lys Ile Thr Asp Ser Asn Ala Val Val Leu Ala Val Lys
        35                  40                  45

Glu Val Glu Thr Leu Leu Ala Ser Ile Asp Glu Leu Ala Glu Lys Ala
    50                  55                  60

Ile Gly Lys Lys Ile Gln Gln Asn Asn Gly Leu Gly Ala Glu Ala Asn
65                  70                  75                  80

Lys Asn Gly Ser Leu Leu Ala Gly Val Tyr Ser Ile Ser Thr Leu Ile
                85                  90                  95

Thr Glu Lys Leu Ser Ala Met Lys Asp Ser Gly Gly Leu Lys Ala Glu
            100                 105                 110

Ile Glu Lys Ala Lys Asp Cys Ser Glu Lys Phe Thr Lys Lys Leu Glu
        115                 120                 125

Thr Ser His Ala Glu Leu Gly Lys Asn Glu Ala Thr Asp Asp Asp Ala
    130                 135                 140

Lys Lys Ala Ile Leu Arg Thr Asn Gly Asp Lys Thr Lys Gly Ala Glu
145                 150                 155                 160

Glu Leu Gln Lys Leu Phe Glu Ser Val Gly Gly Leu Ala Lys Ala Ala
                165                 170                 175

Lys Glu Met Leu Thr Asn Ser Val Lys Glu Leu Thr Ser Pro Val Val
            180                 185                 190

Ala Glu Thr Pro Lys Lys Pro Gly Ser Val Asp Lys Leu
        195                 200                 205
```

<210> SEQ ID NO 5
<211> LENGTH: 196
<212> TYPE: PRT
<213> ORGANISM: Borrelia mayonii

<400> SEQUENCE: 5

```
Met Phe Leu Phe Ile Ser Cys Asn Asn Ser Gly Lys Asp Gly Asn Ala
1               5                   10                  15

Ser Asn Ser Ala Asp Glu Ser Ala Lys Gly Pro Asn Leu Thr Glu Ile
            20                  25                  30

Ser Lys Lys Ile Thr Asp Ser Asn Ala Val Val Leu Ala Val Lys Glu
        35                  40                  45

Val Glu Ala Leu Val Ala Ser Ile Asp Glu Leu Ala Lys Ala Ile Gly
    50                  55                  60

Lys Lys Ile Gln Gln Asn Asn Gly Leu Gly Asn Glu Ala Gly Lys Asn
65                  70                  75                  80

Gly Ser Leu Leu Ser Gly Ile Tyr Thr Ile Ser Thr Val Ile Thr Gln
                85                  90                  95

Lys Leu Gly Ala Leu Asn Asn Glu Glu Leu Lys Glu Arg Ile Lys Glu
            100                 105                 110

Ala Lys Glu Cys Ser Glu Ala Phe Thr Lys Lys Leu Glu Thr Asn His
        115                 120                 125

Thr Asp Leu Gly Lys His Asp Ala Ser Asp Asp Asp Ala Lys Lys Ala
    130                 135                 140
```

```
Ile Leu Arg Thr Asn Gly Asp Lys Thr Lys Gly Ala Glu Glu Leu Glu
145                 150                 155                 160

Lys Leu Phe Lys Ala Val Glu Ser Leu Ser Thr Glu Ala Lys Gly Met
                165                 170                 175

Leu Thr Asn Ser Val Lys Gln Leu Thr Ser Pro Val Val Ala Glu Thr
            180                 185                 190

Pro Lys Lys Pro
        195


<210> SEQ ID NO 6
<211> LENGTH: 197
<212> TYPE: PRT
<213> ORGANISM: Borrelia garinii

<400> SEQUENCE: 6

Met Phe Leu Phe Ile Ser Cys Asn Asn Ser Gly Gly Asp Thr Ala Ser
1               5                   10                  15

Thr Asn Pro Asp Glu Ser Val Lys Gly Pro Asn Leu Thr Glu Ile Ser
            20                  25                  30

Lys Lys Ile Thr Asp Ser Asn Ala Phe Val Leu Ala Val Lys Glu Val
        35                  40                  45

Glu Ala Leu Ile Ser Ser Ile Asp Glu Leu Ala Lys Ala Ile Gly Gln
    50                  55                  60

Arg Ile Gln Gln Asn Gly Leu Val Ala Asp Ala Gly His Asn Ser Ala
65                  70                  75                  80

Leu Leu Ala Gly Ala His Glu Ile Ser Ile Leu Ile Thr Gln Lys Leu
                85                  90                  95

Asp Gly Leu Lys Gly Leu Glu Gly Leu Lys Ala Glu Ile Ala Glu Ala
            100                 105                 110

Lys Lys Tyr Ser Glu Ala Phe Thr Lys Lys Leu Lys Asp Asn His Ala
        115                 120                 125

Gln Leu Gly Ile Gln Asn Gly Ala Ser Leu Asp Asp Glu Ala Lys Lys
    130                 135                 140

Ala Ile Leu Lys Thr Asn Val Asp Lys Thr Lys Gly Ala Glu Glu Leu
145                 150                 155                 160

Glu Lys Leu Phe Lys Ser Val Glu Ser Leu Ser Lys Ala Ala Gln Glu
                165                 170                 175

Ala Leu Thr Asn Ser Val Lys Glu Leu Thr Asn Pro Val Val Ala Glu
            180                 185                 190

Thr Pro Lys Lys Pro
        195


<210> SEQ ID NO 7
<211> LENGTH: 203
<212> TYPE: PRT
<213> ORGANISM: Borrelia afzelii

<400> SEQUENCE: 7

Met Phe Leu Phe Ile Ser Cys Asn Asn Ser Gly Lys Gly Gly Asp Ile
1               5                   10                  15

Ala Ser Thr Asn Pro Asp Glu Ser Ala Lys Gly Pro Asn Leu Thr Glu
            20                  25                  30

Ile Ser Lys Lys Ile Thr Asp Ser Asn Ala Val Val Leu Ala Val Lys
        35                  40                  45

Glu Val Glu Ala Leu Leu Ser Ser Ile Asp Glu Leu Ala Lys Thr Ile
    50                  55                  60
```

-continued

```
Gly Lys Lys Ile Glu Ala Asn Gly Leu Gly Asn Glu Ala Asp Lys Asn
65                  70                  75                  80

Gly Ser Leu Leu Ala Gly Ala Tyr Ala Ile Ser Thr Leu Ile Lys Gln
                85                  90                  95

Lys Leu Asp Gly Leu Lys Gly Leu Glu Gly Leu Asn Lys Glu Ile Ala
            100                 105                 110

Glu Ala Lys Lys Cys Ser Glu Ala Phe Thr Lys Lys Leu Gln Asp Ser
        115                 120                 125

Asn Ala Asp Leu Gly Lys His Asn Ala Thr Asp Ala Asp Ser Lys Glu
    130                 135                 140

Ala Ile Leu Lys Thr Asn Gly Thr Lys Thr Lys Gly Ala Lys Glu Leu
145                 150                 155                 160

Glu Glu Leu Phe Lys Ser Val Glu Ser Leu Ser Lys Ala Ala Lys Glu
                165                 170                 175

Ala Leu Ser Asn Ser Val Lys Glu Leu Thr Ser Pro Val Val Ala Glu
            180                 185                 190

Ser Pro Lys Asn Pro Gly Ser Val Asp Lys Leu
        195                 200


<210> SEQ ID NO 8
<211> LENGTH: 206
<212> TYPE: PRT
<213> ORGANISM: Borrelia spielmanii

<400> SEQUENCE: 8

Met Phe Leu Phe Ile Ser Cys Asn Asn Ser Gly Gly Asp Ser Thr Ser
1               5                   10                  15

Thr Lys Pro Val Asp Glu Pro Ala Lys Gly Pro Asn Leu Ala Glu Ile
            20                  25                  30

Ser Lys Lys Ile Thr Asp Ser Asn Thr Phe Val Leu Ala Val Lys Glu
        35                  40                  45

Val Glu Thr Leu Val Ser Ser Ile Asp Glu Leu Ala Lys Lys Ala Ile
    50                  55                  60

Gly Gln Lys Ile Asp Gln Asn Ser Gly Leu Gly Ala Leu Gln Asn Gln
65                  70                  75                  80

Asn Gly Ser Leu Leu Ala Gly Val Tyr Ala Ile Ser Thr Leu Ile Thr
                85                  90                  95

Asp Lys Leu Ser Lys Leu Lys Asn Ser Glu Glu Leu Lys Ala Glu Ile
            100                 105                 110

Ala Lys Ala Lys Lys Cys Ser Glu Asp Phe Thr Asn Lys Leu Lys Leu
        115                 120                 125

Ser His Ala Asp Leu Gly Ala Val Asn Gly Ala Thr Thr Asp Asp His
    130                 135                 140

Ala Lys Ala Ala Ile Leu Lys Thr Asn Ala Pro Asp Asp Lys Gly Ala
145                 150                 155                 160

Lys Glu Phe Lys Gly Leu Phe Glu Ser Val Glu Ser Leu Ser Lys Ala
                165                 170                 175

Ala Lys Ala Ala Leu Ala Asn Ser Val Lys Glu Leu Thr Ser Pro Val
            180                 185                 190

Ala Ala Glu Ala Pro Lys Lys Pro Gly Ser Val Asp Lys Leu
        195                 200                 205


<210> SEQ ID NO 9
<211> LENGTH: 187
<212> TYPE: PRT
<213> ORGANISM: Borrelia valaisiana
```

<400> SEQUENCE: 9

Met Gly Asp Thr Ala Ser Thr Asn Pro Val Asp Glu Ser Ala Lys Gly
1               5                   10                  15

Pro Asn Leu Thr Glu Ile Ser Lys Lys Ile Thr Asp Ser Asn Ala Ile
            20                  25                  30

Val Leu Ala Val Lys Glu Val Glu Thr Leu Leu Ala Ser Ile Asn Glu
        35                  40                  45

Ile Ala Asn Lys Gly Ile Gly Lys Lys Ile Asn Gln Asn Gly Leu Asp
    50                  55                  60

Asn Leu Thr Asp His Asn Gly Ser Leu Ile Ala Gly Ala Tyr Val Ile
65                  70                  75                  80

Ser Thr Leu Ile Thr Glu Lys Leu Asn Asn Leu Lys Asn Ser Glu Gly
                85                  90                  95

Leu Lys Glu Lys Ile Lys Lys Val Lys Glu Cys Ser Asp Lys Phe Thr
            100                 105                 110

Lys Lys Leu Thr Thr Ser Asn Gly Asp Leu Gly Lys Glu Asn Val Thr
        115                 120                 125

Asp Ala His Ala Gln Ala Ala Ile Leu Lys Thr Asn Pro Thr Asn Asp
    130                 135                 140

Lys Gly Ala Lys Glu Leu Gly Glu Leu Phe Glu Ser Val Glu Ile Leu
145                 150                 155                 160

Ser Lys Ala Ala Gln Glu Ala Leu Thr Asn Ser Ile Ala Glu Leu Thr
                165                 170                 175

Ser Pro Val Val Ala Glu Asn Pro Lys Asn Pro
            180                 185

<210> SEQ ID NO 10
<211> LENGTH: 195
<212> TYPE: PRT
<213> ORGANISM: Borrelia bavariensis

<400> SEQUENCE: 10

Met Phe Leu Phe Ile Ser Cys Asn Asn Ser Gly Gly Asp Ser Ala Ser
1               5                   10                  15

Thr Asn Pro Asp Glu Ser Ala Lys Gly Pro Asn Leu Thr Val Ile Ser
            20                  25                  30

Lys Lys Ile Thr Asp Ser Asn Ala Phe Leu Leu Ala Val Lys Glu Val
        35                  40                  45

Glu Ala Leu Leu Ser Ser Ile Asp Glu Leu Ser Lys Ala Ile Gly Lys
    50                  55                  60

Lys Ile Lys Asn Asp Gly Thr Leu Asp Asn Glu Ala Asn Arg Asn Glu
65                  70                  75                  80

Ser Leu Ile Ala Gly Ala Tyr Glu Ile Ser Lys Leu Ile Thr Gln Lys
                85                  90                  95

Leu Ser Val Leu Asn Ser Glu Glu Leu Lys Glu Lys Ile Lys Glu Ala
            100                 105                 110

Lys Asp Cys Ser Glu Lys Phe Thr Thr Lys Leu Lys Asp Ser His Ala
        115                 120                 125

Glu Leu Gly Ile Gln Ser Val Gln Asp Asp Asn Ala Lys Lys Ala Ile
    130                 135                 140

Leu Lys Thr His Gly Thr Lys Asp Lys Gly Ala Lys Glu Leu Glu Glu
145                 150                 155                 160

Leu Phe Lys Ser Leu Glu Ser Leu Ser Lys Ala Ala Gln Ala Ala Leu
                165                 170                 175

```
Thr Asn Ser Val Lys Glu Leu Thr Asn Pro Val Val Ala Glu Thr Pro
            180                 185                 190

Lys Lys Pro
        195


<210> SEQ ID NO 11
<211> LENGTH: 258
<212> TYPE: PRT
<213> ORGANISM: Borrelia burgdorferi B31

<400> SEQUENCE: 11

Met Ala Lys Gln Asn Val Ser Ser Leu Asp Glu Lys Asn Ser Val Ser
1               5                   10                  15

Val Asp Leu Pro Gly Glu Met Lys Val Leu Val Ser Lys Glu Lys Asn
            20                  25                  30

Lys Asp Gly Lys Tyr Asp Leu Ile Ala Thr Val Asp Lys Leu Glu Leu
        35                  40                  45

Lys Gly Thr Ser Asp Lys Asn Asn Gly Ser Gly Val Leu Glu Gly Val
    50                  55                  60

Lys Ala Asp Lys Ser Lys Val Lys Leu Thr Ile Ser Asp Asp Leu Gly
65                  70                  75                  80

Gln Thr Thr Leu Glu Val Phe Lys Glu Asp Gly Lys Thr Leu Val Ser
                85                  90                  95

Lys Lys Val Thr Ser Lys Asp Lys Ser Ser Thr Glu Glu Lys Phe Asn
            100                 105                 110

Glu Lys Gly Glu Val Ser Glu Lys Ile Ile Thr Arg Ala Asp Gly Thr
        115                 120                 125

Arg Leu Glu Tyr Thr Gly Ile Lys Ser Asp Gly Ser Gly Lys Ala Lys
    130                 135                 140

Glu Val Leu Lys Gly Tyr Val Leu Glu Gly Thr Leu Thr Ala Glu Lys
145                 150                 155                 160

Thr Thr Leu Val Val Lys Glu Gly Thr Val Thr Leu Ser Lys Asn Ile
                165                 170                 175

Ser Lys Ser Gly Glu Val Ser Val Glu Leu Asn Asp Thr Asp Ser Ser
            180                 185                 190

Ala Ala Thr Lys Lys Thr Ala Ala Trp Asn Ser Gly Thr Ser Thr Leu
        195                 200                 205

Thr Ile Thr Val Asn Ser Lys Lys Thr Lys Asp Leu Val Phe Thr Lys
    210                 215                 220

Glu Asn Thr Ile Thr Val Gln Gln Tyr Asp Ser Asn Gly Thr Lys Leu
225                 230                 235                 240

Glu Gly Ser Ala Val Glu Ile Thr Lys Leu Asp Glu Ile Lys Asn Ala
                245                 250                 255

Leu Lys


<210> SEQ ID NO 12
<211> LENGTH: 245
<212> TYPE: PRT
<213> ORGANISM: Borrelia burgdorferi 297

<400> SEQUENCE: 12

Met Ala Lys Gln Asn Val Ser Ser Leu Asp Glu Lys Asn Ser Val Ser
1               5                   10                  15

Val Asp Leu Pro Gly Glu Met Asn Val Leu Val Ser Lys Glu Lys Asn
            20                  25                  30
```

-continued

```
Lys Asp Gly Lys Tyr Asp Leu Ile Ala Thr Val Asp Lys Leu Glu Leu
        35                  40                  45

Lys Gly Thr Ser Asp Lys Asn Asn Gly Ser Gly Val Leu Glu Gly Val
    50                  55                  60

Lys Ala Asp Lys Ser Lys Val Lys Leu Thr Ile Ser Asp Asp Leu Gly
65                  70                  75                  80

Gln Thr Thr Leu Glu Val Phe Lys Glu Asp Gly Lys Thr Leu Val Ser
                85                  90                  95

Lys Lys Val Thr Ser Lys Asp Lys Ser Ser Thr Glu Glu Lys Phe Asn
            100                 105                 110

Glu Lys Gly Glu Val Ser Glu Lys Ile Ile Thr Arg Ala Asp Gly Thr
        115                 120                 125

Arg Leu Glu Tyr Thr Glu Ile Lys Ser Asp Gly Ser Gly Lys Ala Lys
    130                 135                 140

Glu Val Leu Lys Gly Tyr Val Leu Glu Gly Thr Leu Thr Ala Glu Lys
145                 150                 155                 160

Thr Thr Leu Val Val Lys Glu Gly Thr Val Thr Leu Ser Lys Asn Ile
                165                 170                 175

Ser Lys Ser Gly Glu Val Ser Val Glu Leu Asn Asp Thr Asp Ser Ser
            180                 185                 190

Ala Ala Thr Lys Lys Thr Ala Ala Trp Asn Ser Gly Thr Ser Thr Leu
        195                 200                 205

Thr Ile Thr Val Asn Ser Lys Lys Thr Lys Asp Leu Val Phe Thr Lys
    210                 215                 220

Glu Asn Thr Ile Thr Val Gln Gln Tyr Asp Ser Asn Gly Thr Lys Leu
225                 230                 235                 240

Glu Gly Ser Ala Val
                245


<210> SEQ ID NO 13
<211> LENGTH: 257
<212> TYPE: PRT
<213> ORGANISM: Borrelia bissettii

<400> SEQUENCE: 13

Met Lys Gln Asn Val Ser Gly Leu Asp Glu Lys Asn Ser Val Ser Val
1               5                   10                  15

Asp Leu Pro Gly Glu Met Lys Val Leu Val Ser Lys Glu Lys Asp Lys
            20                  25                  30

Asp Gly Lys Tyr Ser Leu Met Ala Thr Val Asp Lys Leu Glu Leu Lys
        35                  40                  45

Gly Thr Ser Asp Lys Asn Asn Gly Ser Gly Ile Leu Glu Gly Val Lys
    50                  55                  60

Ala Asp Lys Ser Lys Val Lys Leu Thr Val Ser Glu Asp Leu Ser Thr
65                  70                  75                  80

Thr Thr Leu Glu Val Leu Lys Glu Asp Gly Lys Thr Leu Val Ser Lys
                85                  90                  95

Lys Thr Thr Ser Lys Asp Lys Ser Ser Thr Glu Glu Lys Phe Asn Asp
            100                 105                 110

Lys Gly Glu Leu Ala Glu Lys Thr Ile Val Arg Ala Asn Gly Thr Arg
        115                 120                 125

Leu Glu Tyr Thr Glu Val Lys Ser Asp Gly Ser Gly Lys Ala Lys Glu
    130                 135                 140

Thr Leu Lys Asp Tyr Ala Leu Glu Gly Thr Leu Thr Ala Glu Lys Ala
145                 150                 155                 160
```

```
Thr Leu Val Val Lys Glu Gly Thr Val Thr Leu Ser Lys His Ile Ser
                165                 170                 175

Lys Ser Gly Glu Val Thr Ala Glu Leu Asn Asp Thr Asp Ser Ala Gln
            180                 185                 190

Ala Thr Lys Lys Thr Gly Lys Trp Asp Ala Gly Thr Ser Thr Leu Thr
        195                 200                 205

Ile Ser Val Asn Ser Lys Lys Thr Lys Asn Leu Val Phe Thr Lys Gln
    210                 215                 220

Asp Thr Ile Thr Val Gln Lys Tyr Asp Ser Ala Gly Thr Asn Leu Glu
225                 230                 235                 240

Gly Thr Ala Val Glu Ile Lys Thr Leu Asp Glu Leu Lys Asn Ala Leu
                245                 250                 255

Lys


<210> SEQ ID NO 14
<211> LENGTH: 258
<212> TYPE: PRT
<213> ORGANISM: Borrelia californiensis

<400> SEQUENCE: 14

Met Ala Lys Gln Asn Val Ser Ser Leu Asp Glu Lys Asn Ser Val Ser
1               5                   10                  15

Val Asp Leu Pro Gly Glu Met Lys Val Leu Val Ser Lys Glu Lys Asp
            20                  25                  30

Lys Asp Gly Lys Tyr Ser Leu Met Ala Thr Val Asp Lys Leu Glu Leu
        35                  40                  45

Lys Gly Thr Ser Asp Lys Asn Asn Gly Ser Gly Val Leu Glu Gly Val
    50                  55                  60

Lys Asp Asp Lys Ser Lys Val Lys Leu Thr Val Ser Asp Asp Leu Ser
65                  70                  75                  80

Thr Thr Thr Leu Glu Val Leu Lys Glu Asp Gly Lys Thr Leu Val Ser
                85                  90                  95

Arg Lys Glu Thr Ser Lys Asp Lys Ser Ser Thr Glu Glu Lys Phe Asn
            100                 105                 110

Glu Lys Gly Glu Leu Thr Glu Lys Ile Met Glu Arg Ser Asn Gly Thr
        115                 120                 125

Arg Leu Glu Tyr Thr Glu Ile Lys Thr Asp Gly Ser Gly Lys Ala Lys
    130                 135                 140

Glu Thr Leu Lys Asp Phe Val Leu Glu Gly Thr Leu Thr Thr Glu Lys
145                 150                 155                 160

Ala Ile Leu Thr Val Lys Glu Gly Thr Val Thr Leu Asn Lys Asn Ile
                165                 170                 175

Ser Lys Ser Gly Glu Val Thr Val Asp Leu Asn Asp Thr Ser Thr Thr
            180                 185                 190

Ala Ala Thr Lys Lys Thr Gly Lys Trp Asp Ser Ser Thr Ser Thr Leu
        195                 200                 205

Thr Val Ser Val Asn Ser Lys Lys Thr Lys Asp Leu Val Phe Thr Lys
    210                 215                 220

Gln Asp Thr Ile Thr Val Gln Lys Tyr Asp Ser Ala Gly Thr Asn Leu
225                 230                 235                 240

Glu Gly Thr Ala Val Glu Ile Lys Thr Leu Asp Glu Ile Lys Asn Ala
                245                 250                 255

Leu Lys
```

<210> SEQ ID NO 15
<211> LENGTH: 258
<212> TYPE: PRT
<213> ORGANISM: Borrelia mayonii

<400> SEQUENCE: 15

```
Met Ala Lys Gln Asn Val Ser Ser Leu Asp Glu Lys Asn Ser Val Ser
1               5                   10                  15

Val Asp Leu Pro Gly Glu Ile Lys Val Leu Val Ser Lys Glu Lys Asp
            20                  25                  30

Lys Asp Gly Lys Tyr Ser Leu Met Ala Thr Val Asp Lys Leu Glu Leu
        35                  40                  45

Lys Gly Thr Ser Asp Lys Asn Asn Gly Ser Gly Val Leu Glu Gly Val
    50                  55                  60

Lys Ala Asp Lys Ser Lys Val Lys Leu Thr Val Ser Asp Asp Leu Ser
65                  70                  75                  80

Lys Thr Thr Leu Glu Val Leu Lys Glu Asp Gly Lys Thr Leu Val Ser
                85                  90                  95

Arg Lys Val Thr Ser Lys Asp Lys Ser Ser Thr Glu Glu Lys Phe Asn
            100                 105                 110

Glu Lys Gly Glu Leu Ala Glu Lys Thr Met Thr Arg Ala Asp Glu Thr
        115                 120                 125

Arg Leu Glu Tyr Thr Glu Ile Lys Ser Asp Gly Ser Gly Lys Ala Lys
    130                 135                 140

Glu Val Leu Lys Gly Tyr Ala Leu Glu Gly Thr Leu Thr Ala Glu Lys
145                 150                 155                 160

Thr Thr Leu Val Val Lys Glu Gly Thr Val Thr Leu Ser Lys Asn Ile
                165                 170                 175

Ser Lys Ser Gly Glu Val Thr Ala Glu Leu Asn Asp Thr Asp Ser Ala
            180                 185                 190

Ala Ala Thr Lys Lys Thr Gly Ala Trp Asn Ser Gly Thr Ser Thr Leu
        195                 200                 205

Thr Ile Thr Ala Asn Ser Lys Lys Thr Lys Asp Leu Val Phe Thr Lys
    210                 215                 220

Glu Asn Thr Ile Thr Val Gln Lys Tyr Asp Thr Ala Gly Ile Lys Leu
225                 230                 235                 240

Glu Gly Ser Ala Val Glu Ile Lys Thr Leu Asp Glu Leu Lys Asn Ala
                245                 250                 255

Leu Lys
```

<210> SEQ ID NO 16
<211> LENGTH: 258
<212> TYPE: PRT
<213> ORGANISM: Borrelia garinii

<400> SEQUENCE: 16

```
Met Lys Gln Asn Val Ser Ser Leu Asp Glu Lys Asn Ser Val Ser Val
1               5                   10                  15

Asp Leu Pro Gly Gly Met Gln Val Leu Val Ser Lys Glu Lys Asp Lys
            20                  25                  30

Asp Gly Lys Tyr Ser Leu Met Ala Thr Val Asp Lys Leu Glu Leu Lys
        35                  40                  45

Gly Thr Ser Asp Lys Asn Asn Gly Ser Gly Thr Leu Glu Gly Glu Lys
    50                  55                  60

Thr Asp Lys Ser Lys Ala Lys Leu Thr Ile Ala Glu Asp Leu Ser Lys
```

```
65                  70                  75                  80

Thr Thr Phe Glu Ile Phe Lys Glu Asp Gly Lys Thr Leu Val Ser Lys
                85                  90                  95

Lys Val Thr Leu Lys Asp Lys Ser Ser Thr Glu Glu Lys Phe Asn Ala
            100                 105                 110

Lys Gly Glu Ala Ser Glu Lys Thr Ile Val Arg Ala Asn Gly Thr Arg
        115                 120                 125

Leu Glu Tyr Thr Asp Ile Lys Ser Asp Lys Thr Gly Lys Ala Lys Glu
    130                 135                 140

Val Leu Lys Asp Phe Ala Leu Glu Gly Thr Leu Ala Ala Asp Gly Lys
145                 150                 155                 160

Thr Thr Leu Lys Val Thr Glu Gly Thr Val Val Leu Ser Lys His Ile
                165                 170                 175

Ser Asn Ser Gly Glu Ile Thr Val Glu Leu Asn Asp Ser Asp Thr Thr
            180                 185                 190

Gln Ala Thr Lys Lys Thr Gly Thr Trp Asp Ser Lys Thr Ser Thr Leu
        195                 200                 205

Thr Ile Ser Val Asn Ser Arg Lys Thr Lys Asn Leu Val Phe Thr Lys
    210                 215                 220

Glu Asp Thr Ile Thr Val Gln Lys Tyr Asp Ser Ala Gly Thr Asn Leu
225                 230                 235                 240

Glu Gly Lys Ala Val Glu Ile Thr Thr Leu Lys Glu Leu Lys Asp Ala
                245                 250                 255

Leu Lys


<210> SEQ ID NO 17
<211> LENGTH: 258
<212> TYPE: PRT
<213> ORGANISM: Borrelia afzelii

<400> SEQUENCE: 17

Met Ala Lys Gln Asn Val Ser Ser Leu Asp Glu Lys Asn Ser Ala Ser
1               5                   10                  15

Val Asp Leu Pro Gly Glu Met Lys Val Leu Val Ser Lys Glu Lys Asp
            20                  25                  30

Lys Asp Gly Lys Tyr Ser Leu Lys Ala Thr Val Asp Lys Ile Glu Leu
        35                  40                  45

Lys Gly Thr Ser Asp Lys Asp Asn Gly Ser Gly Val Leu Glu Gly Thr
    50                  55                  60

Lys Asp Asp Lys Ser Lys Ala Lys Leu Thr Ile Ala Asp Asp Leu Ser
65                  70                  75                  80

Lys Thr Thr Phe Glu Leu Phe Lys Glu Asp Gly Lys Thr Leu Val Ser
                85                  90                  95

Arg Lys Val Ser Ser Lys Asp Lys Thr Ser Thr Asp Glu Met Phe Asn
            100                 105                 110

Glu Lys Gly Glu Leu Ser Ala Lys Thr Met Thr Arg Glu Asn Gly Thr
        115                 120                 125

Lys Leu Glu Tyr Thr Glu Met Lys Ser Asp Gly Thr Gly Lys Ala Lys
    130                 135                 140

Glu Val Leu Lys Asn Phe Thr Leu Glu Gly Lys Val Ala Asn Asp Lys
145                 150                 155                 160

Val Thr Leu Glu Val Lys Glu Gly Thr Val Thr Leu Ser Lys Glu Ile
                165                 170                 175

Ala Lys Ser Gly Glu Val Thr Val Ala Leu Asn Asp Thr Asn Thr Thr
```

-continued

```
            180                 185                 190

Gln Ala Thr Lys Lys Thr Gly Ala Trp Asp Ser Lys Thr Ser Thr Leu
        195                 200                 205

Thr Ile Ser Val Asn Ser Lys Lys Thr Thr Gln Leu Val Phe Thr Lys
    210                 215                 220

Gln Asp Thr Ile Thr Val Gln Lys Tyr Asp Ser Ala Gly Thr Asn Leu
225                 230                 235                 240

Glu Gly Thr Ala Val Glu Ile Lys Thr Leu Asp Glu Leu Lys Asn Ala
                245                 250                 255

Leu Lys


<210> SEQ ID NO 18
<211> LENGTH: 258
<212> TYPE: PRT
<213> ORGANISM: Borrelia spielmanii

<400> SEQUENCE: 18

Met Ala Lys Gln Asn Val Ser Gly Leu Asp Glu Lys Asn Ser Thr Ser
1               5                   10                  15

Val Asp Val Pro Gly Glu Leu Lys Val Leu Val Ser Lys Glu Lys Asp
            20                  25                  30

Lys Asp Gly Lys Tyr Ser Leu Met Ala Thr Val Asp Lys Leu Glu Leu
        35                  40                  45

Lys Gly Thr Ser Asp Lys Asn Asp Gly Ser Gly Val Leu Glu Gly Val
    50                  55                  60

Lys Ala Asp Lys Ser Lys Val Lys Leu Thr Ile Ser Asp His Leu Ser
65                  70                  75                  80

Lys Thr Thr Phe Glu Val Phe Lys Glu Asp Gly Lys Thr Leu Val Ser
                85                  90                  95

Arg Asn Val Asn Ser Lys Asp Lys Ser Ser Thr Lys Glu Lys Phe Asn
            100                 105                 110

Glu Lys Gly Glu Leu Ser Glu Lys Thr Leu Val Arg Ala Asn Gly Thr
        115                 120                 125

Lys Leu Glu Tyr Thr Glu Ile Lys Ser Asp Gly Thr Gly Lys Ala Lys
    130                 135                 140

Glu Val Leu Lys Asp Phe Thr Leu Glu Gly Thr Leu Ala Asn Glu Lys
145                 150                 155                 160

Ala Thr Leu Thr Val Lys Glu Gly Thr Val Thr Leu Ser Lys Asn Ile
                165                 170                 175

Asp Lys Ser Gly Glu Val Thr Val Ala Leu Asn Asp Thr Asp Ser Thr
            180                 185                 190

Ala Ala Thr Lys Lys Thr Gly Ala Trp Asp Ser Lys Thr Ser Thr Leu
        195                 200                 205

Thr Ile Thr Val Asn Ser Lys Lys Thr Lys Asp Leu Val Phe Thr Lys
    210                 215                 220

Gln Asp Thr Ile Thr Val Gln Lys Tyr Asp Ser Ala Gly Thr Asn Leu
225                 230                 235                 240

Glu Gly Ser Ala Val Glu Ile Lys Thr Leu Asp Glu Leu Lys Asn Ala
                245                 250                 255

Leu Lys


<210> SEQ ID NO 19
<211> LENGTH: 259
<212> TYPE: PRT
<213> ORGANISM: Borrelia valaisiana
```

-continued

<400> SEQUENCE: 19

```
Met Ala Lys Gln Asn Val Ser Ser Leu Asp Glu Lys Asn Ser Ala Ser
1               5                   10                  15

Val Asp Leu Pro Gly Glu Met Lys Val Leu Val Ser Lys Glu Lys Asp
            20                  25                  30

Lys Asp Gly Lys Tyr Ser Leu Val Ala Thr Val Asp Lys Val Glu Leu
        35                  40                  45

Lys Gly Thr Ser Asp Lys Asn Asn Gly Ser Gly Thr Leu Glu Gly Val
    50                  55                  60

Lys Asp Asp Lys Ser Lys Val Lys Leu Thr Ile Ser Asp Asp Leu Gly
65                  70                  75                  80

Glu Thr Lys Leu Glu Thr Phe Lys Glu Asp Gly Thr Leu Val Ser Arg
                85                  90                  95

Lys Val Asn Phe Lys Asp Lys Ser Phe Thr Glu Glu Lys Phe Asn Glu
            100                 105                 110

Lys Gly Glu Val Ser Glu Lys Ile Leu Thr Arg Ser Asn Gly Thr Thr
        115                 120                 125

Leu Glu Tyr Ser Gln Met Thr Asp Ala Glu Asn Ala Thr Lys Ala Val
    130                 135                 140

Glu Thr Leu Lys Asn Gly Ile Lys Leu Pro Gly Asn Leu Val Gly Gly
145                 150                 155                 160

Lys Thr Thr Leu Lys Ile Thr Glu Gly Thr Val Thr Leu Ser Lys His
                165                 170                 175

Ile Ala Lys Ser Gly Glu Val Thr Val Glu Ile Asn Asp Thr Ser Ser
            180                 185                 190

Thr Pro Asn Thr Lys Lys Thr Gly Lys Trp Asp Ala Arg Asn Ser Thr
        195                 200                 205

Leu Thr Ile Ile Val Asp Ser Lys Asn Lys Thr Lys Leu Val Phe Thr
    210                 215                 220

Lys Gln Asp Thr Ile Thr Val Gln Ser Tyr Asn Pro Ala Gly Asn Lys
225                 230                 235                 240

Leu Glu Gly Thr Ala Val Glu Ile Lys Thr Leu Gln Glu Leu Lys Asn
                245                 250                 255

Ala Leu Lys
```

<210> SEQ ID NO 20
<211> LENGTH: 257
<212> TYPE: PRT
<213> ORGANISM: Borrelia bavariensis

<400> SEQUENCE: 20

```
Met Lys Gln Asn Val Ser Ser Leu Asp Glu Lys Asn Ser Val Ser Val
1               5                   10                  15

Asp Leu Pro Gly Glu Met Lys Val Leu Val Ser Lys Glu Lys Asp Lys
            20                  25                  30

Asp Gly Lys Tyr Ser Leu Met Ala Thr Val Asp Lys Leu Glu Leu Lys
        35                  40                  45

Gly Thr Ser Asp Lys Ser Asn Gly Ser Gly Thr Leu Glu Gly Glu Lys
    50                  55                  60

Ser Asp Lys Ser Lys Ala Lys Leu Thr Ile Ser Glu Asp Leu Ser Lys
65                  70                  75                  80

Thr Thr Phe Glu Ile Phe Lys Glu Asp Gly Lys Thr Leu Val Ser Lys
                85                  90                  95
```

-continued

Lys Val Asn Ser Lys Asp Lys Ser Ser Ile Glu Glu Lys Phe Asn Ala
100 105 110

Lys Gly Glu Leu Ser Glu Lys Thr Ile Leu Arg Ala Asn Gly Thr Arg
115 120 125

Leu Glu Tyr Thr Glu Ile Lys Ser Asp Gly Thr Gly Lys Ala Lys Glu
130 135 140

Val Leu Lys Asp Phe Ala Leu Glu Gly Thr Leu Ala Ala Asp Lys Thr
145 150 155 160

Thr Leu Lys Val Thr Glu Gly Thr Val Val Leu Ser Lys His Ile Pro
165 170 175

Asn Ser Gly Glu Ile Thr Val Glu Leu Asn Asp Ser Asn Ser Thr Gln
180 185 190

Ala Thr Lys Lys Thr Gly Lys Trp Asp Ser Asn Thr Ser Thr Leu Thr
195 200 205

Ile Ser Val Asn Ser Lys Lys Thr Lys Asn Ile Val Phe Thr Lys Glu
210 215 220

Asp Thr Ile Thr Val Gln Lys Tyr Asp Ser Ala Gly Thr Asn Leu Glu
225 230 235 240

Gly Asn Ala Val Glu Ile Lys Thr Leu Asp Glu Leu Lys Asn Ala Leu
245 250 255

Lys

<210> SEQ ID NO 21
<211> LENGTH: 320
<212> TYPE: PRT
<213> ORGANISM: Borrelia burgdorferi B31

<400> SEQUENCE: 21

Met Lys Gly Ser Leu Gly Ser Glu Ile Pro Lys Val Ser Leu Ile Ile
1 5 10 15

Asp Gly Thr Phe Asp Asp Lys Ser Phe Asn Glu Ser Ala Leu Asn Gly
20 25 30

Val Lys Lys Val Lys Glu Glu Phe Lys Ile Glu Leu Val Leu Lys Glu
35 40 45

Ser Ser Ser Asn Ser Tyr Leu Ser Asp Leu Glu Gly Leu Lys Asp Ala
50 55 60

Gly Ser Asp Leu Ile Trp Leu Ile Gly Tyr Arg Phe Ser Asp Val Ala
65 70 75 80

Lys Val Ala Ala Leu Gln Asn Pro Asp Met Lys Tyr Ala Ile Ile Asp
85 90 95

Pro Ile Tyr Ser Asn Asp Pro Ile Pro Ala Asn Leu Val Gly Met Thr
100 105 110

Phe Arg Ala Gln Glu Gly Ala Phe Leu Thr Gly Tyr Ile Ala Ala Lys
115 120 125

Leu Ser Lys Thr Gly Lys Ile Gly Phe Leu Gly Gly Ile Glu Gly Glu
130 135 140

Ile Val Asp Ala Phe Arg Tyr Gly Tyr Glu Ala Gly Ala Lys Tyr Ala
145 150 155 160

Asn Lys Asp Ile Lys Ile Ser Thr Gln Tyr Ile Gly Ser Phe Ala Asp
165 170 175

Leu Glu Ala Gly Arg Ser Val Ala Thr Arg Met Tyr Ser Asp Glu Ile
180 185 190

Asp Ile Ile His His Ala Ala Ser Leu Gly Gly Ile Gly Ala Ile Glu
195 200 205

-continued

```
Val Pro Lys Glu Leu Gly Ser Gly His Tyr Ile Ile Gly Val Asp Glu
    210                 215                 220

Asp Gln Ala Tyr Leu Ala Pro Asp Asn Val Ile Thr Ser Thr Thr Lys
225                 230                 235                 240

Asp Val Gly Arg Ala Leu Asn Ile Phe Thr Ser Asn His Leu Lys Thr
                245                 250                 255

Asn Thr Phe Glu Gly Gly Lys Leu Ile Asn Tyr Gly Leu Lys Glu Gly
            260                 265                 270

Val Val Gly Phe Val Arg Asn Pro Lys Met Ile Ser Phe Glu Leu Glu
        275                 280                 285

Lys Glu Ile Asp Asn Leu Ser Ser Lys Ile Ile Asn Lys Glu Ile Ile
    290                 295                 300

Val Pro Ser Asn Lys Glu Ser Tyr Glu Lys Phe Leu Lys Glu Phe Ile
305                 310                 315                 320


<210> SEQ ID NO 22
<211> LENGTH: 320
<212> TYPE: PRT
<213> ORGANISM: Borrelia burgdorferi 297

<400> SEQUENCE: 22

Met Lys Gly Ser Leu Gly Ser Glu Ile Pro Lys Val Ser Leu Ile Ile
1               5                   10                  15

Asp Gly Thr Phe Asp Asp Lys Ser Phe Asn Glu Ser Ala Leu Asn Gly
            20                  25                  30

Val Lys Lys Val Lys Glu Glu Phe Lys Ile Glu Leu Val Leu Lys Glu
        35                  40                  45

Ser Ser Ser Asn Ser Tyr Leu Ser Asp Leu Glu Gly Leu Lys Asp Ala
    50                  55                  60

Gly Ser Asp Leu Ile Trp Leu Ile Gly Tyr Arg Phe Ser Asp Val Ala
65                  70                  75                  80

Lys Val Ala Ala Leu Gln Asn Pro Asp Met Lys Tyr Ala Ile Ile Asp
                85                  90                  95

Pro Ile Tyr Ser Asn Asp Pro Ile Pro Ala Asn Leu Val Gly Met Thr
            100                 105                 110

Phe Arg Ala Gln Glu Gly Ala Phe Leu Thr Gly Tyr Ile Ala Ala Lys
        115                 120                 125

Leu Ser Lys Thr Gly Lys Ile Gly Phe Leu Gly Gly Ile Glu Gly Glu
    130                 135                 140

Ile Val Asp Ala Phe Arg Tyr Gly Tyr Glu Ala Gly Ala Lys Tyr Ala
145                 150                 155                 160

Asn Lys Asp Ile Lys Ile Ser Thr Gln Tyr Ile Gly Ser Phe Ala Asp
                165                 170                 175

Leu Glu Ala Gly Arg Ser Val Ala Thr Arg Met Tyr Ser Asp Glu Ile
            180                 185                 190

Asp Ile Ile His His Ala Ala Ser Leu Gly Gly Ile Gly Ala Ile Glu
        195                 200                 205

Val Pro Lys Glu Leu Gly Ser Gly His Tyr Ile Ile Gly Val Asp Glu
    210                 215                 220

Asp Gln Ala Tyr Leu Ala Pro Asp Asn Val Ile Thr Ser Thr Thr Lys
225                 230                 235                 240

Asp Val Gly Arg Ala Leu Asn Ile Phe Thr Ser Asn His Leu Lys Thr
                245                 250                 255

Asn Thr Ser Glu Gly Gly Lys Leu Ile Asn Tyr Gly Leu Lys Glu Gly
            260                 265                 270
```

-continued

Val Val Gly Phe Val Arg Asn Pro Lys Met Ile Ser Phe Glu Leu Glu
275 280 285

Lys Glu Ile Asp Asn Leu Ser Ser Lys Ile Ile Asn Lys Glu Ile Ile
290 295 300

Val Pro Ser Asn Lys Glu Ser Tyr Glu Lys Phe Leu Lys Glu Phe Ile
305 310 315 320

<210> SEQ ID NO 23
<211> LENGTH: 318
<212> TYPE: PRT
<213> ORGANISM: Borrelia garinii

<400> SEQUENCE: 23

Met Lys Gly Ser Leu Glu Ser Glu Ile Pro Lys Val Ser Leu Ile Ile
1 5 10 15

Asp Gly Thr Phe Asp Asp Lys Ser Phe Asn Glu Ser Ala Leu Asn Gly
20 25 30

Ile Lys Lys Val Lys Glu Glu Phe Lys Ile Glu Pro Val Leu Lys Glu
35 40 45

Ser Ser Ile Asn Ser Tyr Leu Ser Asp Leu Glu Gly Leu Lys Asp Thr
50 55 60

Gly Ser Asn Leu Ile Trp Leu Ile Gly Tyr Lys Phe Ser Asp Val Ala
65 70 75 80

Lys Ala Val Ser Leu Gln Asn Pro Glu Ile Lys Tyr Ala Ile Ile Asp
85 90 95

Pro Ile Tyr Ser Asp Glu Pro Ile Pro Ala Asn Leu Val Gly Met Thr
100 105 110

Phe Arg Ser Gln Glu Gly Ala Phe Leu Thr Gly Tyr Ile Ala Ala Lys
115 120 125

Val Ser Lys Thr Gly Lys Ile Gly Phe Leu Gly Gly Ile Glu Gly Glu
130 135 140

Ile Val Asp Ser Phe Arg Tyr Gly Tyr Glu Ala Gly Ala Lys Tyr Ala
145 150 155 160

Asn Lys Asp Ile Lys Ile Ser Ala Tyr Tyr Ile Gly Ser Phe Ala Asp
165 170 175

Leu Glu Ala Gly Arg Ser Val Ala Thr Lys Met Tyr Ser Asp Gly Ile
180 185 190

Asp Ile Ile His His Ala Ala Gly Leu Gly Gly Ile Gly Ala Ile Glu
195 200 205

Val Ala Lys Glu Leu Gly Ser Gly His Tyr Ile Ile Gly Val Asp Glu
210 215 220

Asp Gln Ser Tyr Leu Ala Pro Asn Asn Ile Ile Thr Ser Ala Thr Lys
225 230 235 240

Asp Val Gly Arg Ser Leu Asn Ile Phe Thr Ser Asn Tyr Leu Lys Thr
245 250 255

Asn Thr Phe Glu Gly Gly Arg Leu Ile Asn Tyr Gly Leu Lys Glu Gly
260 265 270

Val Val Gly Phe Val Lys Asn Pro Lys Met Ile Pro Phe Glu Leu Glu
275 280 285

Lys Glu Ile Asp Asn Leu Ser Ser Lys Ile Ile Asn Lys Glu Ile Ile
290 295 300

Val Pro Tyr Asn Lys Glu Ser Tyr Glu Lys Phe Leu Lys Glu
305 310 315

<210> SEQ ID NO 24
<211> LENGTH: 320
<212> TYPE: PRT
<213> ORGANISM: Borrelia afzelii

<400> SEQUENCE: 24

```
Met Lys Ser Gly Leu Glu Ser Gly Ile Pro Lys Val Ser Leu Val Ile
1               5                   10                  15

Asp Gly Thr Phe Asp Asp Lys Ser Phe Asn Glu Ser Ala Leu Asn Gly
            20                  25                  30

Val Lys Lys Leu Lys Glu Glu Phe Glu Ile Glu Leu Val Leu Lys Glu
        35                  40                  45

Ser Ser Thr Asn Ser Tyr Leu Ser Asp Leu Glu Gly Leu Lys Asp Ala
    50                  55                  60

Gly Ser Asn Leu Ile Trp Leu Ile Gly Tyr Lys Phe Ser Asp Val Ala
65                  70                  75                  80

Lys Ala Val Ser Leu Gln Asn Ser Glu Met Lys Tyr Ala Ile Ile Asp
                85                  90                  95

Pro Val Tyr Ser Asn Glu Pro Ile Pro Ala Asn Leu Val Gly Met Thr
            100                 105                 110

Phe Arg Ala Gln Glu Gly Ala Phe Leu Thr Gly Tyr Ile Ala Ala Lys
        115                 120                 125

Val Ser Lys Thr Gly Lys Ile Gly Phe Leu Gly Gly Ile Glu Gly Asp
    130                 135                 140

Ile Val Asp Ala Phe Arg Tyr Gly Tyr Glu Ala Gly Ala Lys Tyr Ala
145                 150                 155                 160

Asn Lys Asp Ile Lys Ile Phe Ser Gln Tyr Ile Gly Ser Phe Ser Asp
                165                 170                 175

Leu Glu Ala Gly Arg Ser Val Ala Thr Lys Met Tyr Ser Asp Gly Ile
            180                 185                 190

Asp Ile Ile His His Ala Ala Gly Leu Gly Gly Ile Gly Ala Ile Glu
        195                 200                 205

Val Ala Lys Glu Leu Gly Ser Gly His Tyr Ile Ile Gly Val Asp Glu
    210                 215                 220

Asp Gln Ser Tyr Leu Ala Pro Asn Asn Val Ile Thr Ser Thr Thr Lys
225                 230                 235                 240

Asp Val Gly Arg Ser Leu Asn Leu Phe Thr Ser Asn Tyr Leu Lys Thr
                245                 250                 255

Asn Thr Phe Glu Gly Gly Lys Leu Ile Asn Tyr Gly Leu Lys Glu Gly
            260                 265                 270

Val Val Gly Phe Val Arg Asn Pro Lys Met Ile Pro Phe Glu Val Glu
        275                 280                 285

Lys Glu Ile Asp Ser Leu Ser Ser Lys Ile Ile Asn Lys Glu Val Ile
    290                 295                 300

Val Pro Tyr Asn Lys Glu Ser Tyr Glu Lys Phe Leu Lys Glu Phe Ile
305                 310                 315                 320
```

<210> SEQ ID NO 25
<211> LENGTH: 320
<212> TYPE: PRT
<213> ORGANISM: Borrelia spielmanii

<400> SEQUENCE: 25

```
Met Lys Gly Gly Leu Glu Asn Lys Ile Pro Lys Val Ser Leu Ile Ile
1               5                   10                  15

Asp Gly Thr Phe Asp Asp Lys Ser Phe Asn Glu Ser Ala Leu Asn Gly
```

-continued

```
            20                  25                  30

Val Lys Lys Leu Lys Glu Glu Phe Glu Ile Asp Leu Val Leu Lys Glu
        35                  40                  45

Ser Ser Thr Asn Ser Tyr Val Ser Asp Leu Glu Gly Leu Lys Asp Ala
    50                  55                  60

Gly Ser Asn Leu Ile Trp Leu Ile Gly Tyr Lys Phe Ser Asp Val Ala
65                  70                  75                  80

Lys Ala Val Ser Leu Gln Asn Ser Glu Met Lys Tyr Ala Ile Ile Asp
                85                  90                  95

Pro Val Tyr Ser Ser Glu Pro Ile Pro Ala Asn Leu Val Gly Met Thr
            100                 105                 110

Phe Arg Ala Gln Glu Gly Ala Phe Leu Thr Gly Tyr Ile Ala Ser Lys
        115                 120                 125

Val Ser Lys Thr Gly Lys Ile Gly Phe Leu Gly Gly Ile Glu Gly Asp
    130                 135                 140

Ile Val Asp Ala Phe Arg Tyr Gly Tyr Glu Ala Gly Ala Lys Tyr Ala
145                 150                 155                 160

Asn Lys Asp Ile Lys Ile Phe Ser Gln Tyr Ile Gly Ser Phe Ala Asp
                165                 170                 175

Ile Glu Ala Gly Arg Ser Val Ala Thr Lys Met Tyr Ser Asp Gly Ile
            180                 185                 190

Asp Ile Ile His His Ala Ala Gly Leu Gly Gly Ile Gly Ala Ile Glu
        195                 200                 205

Val Ala Lys Glu Leu Gly Ser Gly His Tyr Ile Ile Gly Val Asp Glu
    210                 215                 220

Asp Gln Ser Tyr Leu Ala Pro Asn Asn Val Ile Thr Ser Ser Thr Lys
225                 230                 235                 240

Asp Val Gly Arg Ser Leu Asn Leu Phe Thr Ser Asn Tyr Leu Lys Thr
                245                 250                 255

Asn Asn Phe Glu Gly Gly Lys Leu Ile Asn Tyr Gly Leu Lys Glu Gly
            260                 265                 270

Val Val Gly Phe Val Arg Asn Pro Lys Met Ile Pro Phe Glu Val Glu
        275                 280                 285

Lys Glu Ile Asp Ser Leu Ser Gly Lys Ile Ile Asn Lys Glu Val Ile
    290                 295                 300

Val Pro Tyr Asn Lys Glu Ser Tyr Glu Lys Phe Leu Lys Glu Phe Leu
305                 310                 315                 320


<210> SEQ ID NO 26
<211> LENGTH: 320
<212> TYPE: PRT
<213> ORGANISM: Borrelia valaisiana

<400> SEQUENCE: 26

Met Lys Gly Ser Leu Glu Gly Gly Ile Pro Lys Val Ser Val Ile Ile
1               5                   10                  15

Asp Gly Thr Phe Asp Asp Lys Ser Phe Asn Glu Ser Ala Leu Asn Gly
            20                  25                  30

Ile Lys Lys Val Lys Glu Glu Phe Lys Val Glu Phe Val Leu Lys Glu
        35                  40                  45

Ser Ser Ser Asn Ser Tyr Leu Ser Asp Leu Glu Gly Leu Lys Asp Thr
    50                  55                  60

Gly Ser Asn Leu Ile Trp Leu Ile Gly Tyr Arg Phe Ser Asp Val Ala
65                  70                  75                  80
```

Lys Val Val Ser Leu Gln Asn Ser Glu Val Lys Tyr Ala Ile Ile Asp
85 90 95

Pro Val Tyr Ser Asn Glu Pro Ile Pro Ala Asn Leu Val Gly Met Thr
100 105 110

Phe Arg Ala Gln Glu Gly Ala Phe Leu Thr Gly Tyr Ile Ala Ser Lys
115 120 125

Val Ser Lys Thr Gly Lys Ile Gly Phe Leu Gly Gly Ile Lys Ser Glu
130 135 140

Ile Val Asp Ala Phe Arg Tyr Gly Tyr Glu Ala Gly Ala Lys Tyr Ala
145 150 155 160

Asn Lys Asp Ile Lys Ile Phe Thr His Tyr Ile Gly Ser Phe Ala Asp
165 170 175

Leu Glu Ala Ser Arg Ser Ile Ala Ile Lys Met Tyr Ser Asp Gly Ile
180 185 190

Asp Ile Ile His His Ala Ala Gly Leu Gly Gly Ile Gly Ala Ile Glu
195 200 205

Val Ala Lys Glu Leu Gly Ser Gly His Tyr Ile Ile Gly Val Asp Glu
210 215 220

Asp Gln Ser Tyr Leu Ala Pro Asp Asn Val Ile Thr Ser Ser Thr Lys
225 230 235 240

Asp Val Gly Arg Ala Leu Asn Ile Phe Thr Ser Asn Tyr Leu Lys Thr
245 250 255

Asn Thr Phe Glu Gly Gly Lys Leu Ile Asn Tyr Gly Leu Lys Glu Gly
260 265 270

Val Val Gly Phe Val Arg Asn Pro Lys Met Ile Pro Phe Glu Leu Glu
275 280 285

Lys Glu Ile Asp Ser Ile Ser Ser Lys Ile Ile Asn Lys Glu Val Ile
290 295 300

Val Pro Tyr Asn Lys Gly Ser Tyr Glu Lys Phe Leu Lys Glu Phe Ile
305 310 315 320

<210> SEQ ID NO 27
<211> LENGTH: 696
<212> TYPE: PRT
<213> ORGANISM: Borrelia burgdorferi B31

<400> SEQUENCE: 27

Met Phe Leu Asn Gly Phe Pro Leu Asn Ala Arg Lys Val Asp Lys Glu
1 5 10 15

Lys Leu Lys Asp Phe Val Asn Met Asp Leu Glu Phe Val Asn Tyr Lys
20 25 30

Gly Pro Tyr Asp Ser Thr Asn Thr Tyr Glu Gln Ile Val Gly Ile Gly
35 40 45

Glu Phe Leu Ala Arg Pro Leu Thr Asn Ser Asn Ser Asn Ser Ser Tyr
50 55 60

Tyr Gly Lys Tyr Phe Ile Asn Arg Phe Ile Asp Asp Gln Asp Lys Lys
65 70 75 80

Ala Ser Val Asp Val Phe Ser Ile Ser Ser Lys Ser Glu Leu Asp Ser
85 90 95

Ile Leu Asn Leu Arg Arg Ile Leu Thr Gly Tyr Ile Ile Lys Ser Phe
100 105 110

Asp Tyr Asp Arg Ser Ser Ala Glu Leu Ile Ala Lys Val Ile Thr Ile
115 120 125

Tyr Asn Ala Val Tyr Arg Gly Asp Leu Asp Tyr Tyr Lys Gly Phe Tyr
130 135 140

-continued

```
Ile Glu Pro Ala Leu Lys Ser Leu Thr Lys Glu Asn Ala Gly Leu Ser
145                 150                 155                 160

Arg Val Tyr Ser Gln Trp Ala Gly Lys Thr Gln Ile Phe Ile Pro Leu
                165                 170                 175

Lys Lys Asp Ile Leu Ser Gly Asn Ile Glu Ser Asp Ile Asp Ile Asp
            180                 185                 190

Ser Leu Val Thr Asp Lys Val Ile Ala Ala Leu Leu Ser Glu Asn Glu
        195                 200                 205

Ala Gly Val Asn Phe Ala Arg Asp Ile Thr Asp Ile Gln Gly Glu Thr
    210                 215                 220

His Lys Ala Asp Gln Asp Lys Ile Asp Thr Glu Leu Asp Asn Ile His
225                 230                 235                 240

Glu Ser Asp Ser Asn Ile Thr Glu Thr Ile Glu Asn Leu Arg Asp Gln
                245                 250                 255

Leu Glu Lys Ala Thr Asp Glu Glu His Lys Lys Glu Ile Glu Ser Gln
            260                 265                 270

Val Asp Ala Lys Lys Lys Glu Lys Glu Glu Leu Asp Lys Lys Ala Ile
        275                 280                 285

Asn Leu Asp Lys Ala Gln Gln Lys Leu Asp Ser Ala Glu Asp Asn Leu
    290                 295                 300

Asp Val Gln Arg Asp Thr Val Arg Glu Lys Ile Gln Glu Asp Ile Asn
305                 310                 315                 320

Glu Ile Asn Lys Glu Lys Asn Leu Pro Lys Pro Gly Asp Val Ser Ser
                325                 330                 335

Pro Lys Val Asp Lys Gln Leu Gln Ile Lys Glu Ser Leu Glu Asp Leu
            340                 345                 350

Gln Glu Gln Leu Lys Glu Ala Gly Asp Glu Asn Gln Lys Arg Glu Ile
        355                 360                 365

Glu Lys Gln Ile Glu Ile Lys Lys Arg Asp Glu Glu Leu Leu Lys Ser
    370                 375                 380

Lys Asp Gly Lys Val Ser Lys Asp Tyr Glu Ala Leu Asp Leu Asp Arg
385                 390                 395                 400

Glu Leu Ser Lys Ala Ser Ser Lys Glu Lys Ser Lys Val Lys Glu Glu
                405                 410                 415

Glu Ile Thr Lys Gly Lys Ser Arg Ala Ser Leu Gly Asp Leu Asn Asn
            420                 425                 430

Asp Lys Asn Leu Met Leu Pro Glu Asp Gln Lys Leu Pro Glu Asp Lys
        435                 440                 445

Lys Leu Asp Ser Lys Leu Asp Gly Lys Lys Glu Phe Lys Pro Val Ser
    450                 455                 460

Glu Val Glu Lys Leu Asp Lys Ile Ser Lys Ser Asn Asn Asn Glu Val
465                 470                 475                 480

Gly Lys Leu Ser Pro Leu Asp Lys Pro Ser Tyr Asp Asp Ile Asp Ser
                485                 490                 495

Lys Glu Glu Val Asp Asn Lys Ala Ile Asn Leu Gln Lys Ile Asp Pro
            500                 505                 510

Lys Val Lys Asp Gln Thr Thr Ser Leu Asn Glu Asp Leu Asp Lys Asp
        515                 520                 525

Leu Thr Thr Met Ser Ile Asp Ser Ser Ser Pro Val Phe Leu Glu Val
    530                 535                 540

Ile Asp Pro Ile Thr Asn Leu Gly Thr Leu Gln Leu Ile Asp Leu Asn
545                 550                 555                 560
```

-continued

```
Thr Gly Val Arg Leu Lys Glu Ser Thr Gln Gln Gly Ile Gln Arg Tyr
                565                 570                 575

Gly Ile Tyr Glu Arg Glu Lys Asp Leu Val Val Ile Lys Met Asp Ser
            580                 585                 590

Gly Lys Ala Lys Leu Gln Ile Leu Asn Lys Leu Glu Asn Leu Lys Val
        595                 600                 605

Val Ser Glu Ser Asn Phe Glu Ile Asn Lys Asn Ser Ser Leu Tyr Val
    610                 615                 620

Asp Ser Lys Met Ile Leu Ala Ala Val Arg Asp Lys Asp Asp Ser Asn
625                 630                 635                 640

Ala Trp Arg Leu Ala Lys Phe Ser Pro Lys Asn Leu Asp Glu Phe Ile
                645                 650                 655

Leu Ser Glu Asn Lys Ile Leu Pro Phe Thr Ser Phe Ser Val Arg Lys
            660                 665                 670

Asn Phe Ile Tyr Leu Gln Asp Glu Leu Lys Asn Leu Val Ile Leu Asp
        675                 680                 685

Val Asn Thr Leu Lys Lys Val Lys
    690                 695
```

<210> SEQ ID NO 28
<211> LENGTH: 688
<212> TYPE: PRT
<213> ORGANISM: Borrelia burgdorferi 297

<400> SEQUENCE: 28

```
Met Phe Leu Asn Gly Phe Pro Val Ser Ala Arg Glu Val Asp Arg Glu
1               5                   10                  15

Lys Leu Lys Asp Phe Val Asn Met Asp Leu Glu Phe Val Asn Tyr Lys
            20                  25                  30

Gly Pro Tyr Asp Ser Thr Asn Thr Tyr Glu Gln Ile Val Gly Ile Gly
        35                  40                  45

Glu Phe Leu Ala Arg Pro Leu Thr Asn Ser Asn Ser Asn Ser Ser Tyr
    50                  55                  60

Tyr Gly Lys Tyr Phe Ile Asn Arg Phe Ile Asp Asp Gln Asp Lys Lys
65                  70                  75                  80

Ala Ser Val Asp Val Phe Ser Ile Gly Ser Lys Ser Glu Leu Asp Ser
                85                  90                  95

Ile Leu Asn Leu Arg Arg Ile Leu Thr Gly Tyr Leu Ile Lys Ser Phe
            100                 105                 110

Asp Tyr Asp Arg Ser Ser Ala Glu Leu Ile Ala Lys Val Ile Thr Ile
        115                 120                 125

Tyr Asn Ala Val Tyr Arg Gly Asp Leu Asp Tyr Tyr Lys Gly Phe Tyr
    130                 135                 140

Ile Glu Ala Ala Leu Lys Ser Leu Ser Lys Glu Asn Ala Gly Leu Ser
145                 150                 155                 160

Arg Val Tyr Ser Gln Trp Ala Gly Lys Thr Gln Ile Phe Ile Pro Leu
                165                 170                 175

Lys Lys Asp Ile Leu Ser Gly Asn Ile Glu Ser Asp Ile Asp Ile Asp
            180                 185                 190

Ser Leu Val Thr Asp Lys Val Val Ala Ala Leu Leu Ser Glu Asn Glu
        195                 200                 205

Ala Gly Val Asn Phe Ala Arg Asp Ile Thr Asp Ile Gln Gly Glu Thr
    210                 215                 220

His Lys Ala Asp Gln Asp Lys Ile Asp Ile Glu Leu Asp Asn Ile His
225                 230                 235                 240
```

-continued

```
Glu Ser Asp Ser Asn Ile Thr Glu Thr Ile Glu Asn Leu Arg Asp Gln
                245                 250                 255

Leu Glu Lys Ala Thr Asp Glu Glu His Lys Lys Glu Ile Glu Ser Gln
            260                 265                 270

Val Asp Ala Lys Lys Lys Gln Lys Glu Glu Leu Asp Lys Lys Ala Ile
        275                 280                 285

Asn Leu Asp Lys Ala Gln Gln Lys Leu Asp Ser Ala Glu Asp Asn Leu
    290                 295                 300

Asp Val Gln Arg Asn Thr Val Arg Glu Lys Ile Gln Glu Asp Ile Asn
305                 310                 315                 320

Glu Ile Asn Lys Glu Lys Asn Leu Pro Lys Pro Gly Asp Val Ser Ser
                325                 330                 335

Pro Lys Val Asp Lys Gln Leu Gln Ile Lys Glu Ser Leu Glu Asp Leu
            340                 345                 350

Gln Glu Gln Leu Lys Glu Thr Gly Asp Glu Asn Gln Lys Arg Glu Ile
        355                 360                 365

Glu Lys Gln Ile Glu Ile Lys Lys Ser Asp Glu Lys Leu Leu Lys Ser
    370                 375                 380

Lys Asp Asp Lys Ala Ser Lys Asp Gly Lys Ala Leu Asp Leu Asp Arg
385                 390                 395                 400

Glu Leu Asn Ser Lys Ala Ser Ser Lys Glu Lys Ser Lys Ala Lys Glu
                405                 410                 415

Glu Glu Ile Thr Lys Gly Lys Ser Gln Lys Ser Leu Gly Asp Leu Asn
            420                 425                 430

Asn Asp Glu Asn Leu Met Met Pro Glu Asp Gln Lys Leu Pro Glu Val
        435                 440                 445

Lys Lys Leu Asp Ser Lys Lys Glu Phe Lys Pro Val Ser Glu Val Asp
    450                 455                 460

Lys Leu Asp Lys Ile Ser Lys Ser Asn Asn Asn Val Gly Glu Leu Ser
465                 470                 475                 480

Pro Leu Asp Lys Ser Ser Tyr Lys Asp Ile Asp Ser Lys Glu Glu Thr
                485                 490                 495

Val Asn Lys Asp Val Asn Leu Gln Lys Thr Lys Pro Gln Val Lys Asp
            500                 505                 510

Gln Val Thr Ser Leu Asn Glu Asp Leu Thr Thr Met Ser Ile Asp Ser
        515                 520                 525

Ser Ser Pro Val Phe Leu Glu Val Ile Asp Pro Ile Thr Asn Leu Gly
    530                 535                 540

Thr Leu Gln Leu Ile Asp Leu Asn Thr Gly Val Arg Leu Lys Glu Ser
545                 550                 555                 560

Thr Gln Gln Gly Ile Gln Arg Tyr Gly Ile Tyr Glu Arg Glu Lys Asp
                565                 570                 575

Leu Val Val Ile Lys Met Asp Ser Gly Lys Ala Lys Leu Gln Ile Leu
            580                 585                 590

Asp Lys Leu Lys Asn Leu Lys Val Val Ser Glu Ser Asn Phe Glu Ile
        595                 600                 605

Asn Lys Asn Ser Ser Leu Tyr Val Asp Ser Lys Met Ile Leu Val Ala
    610                 615                 620

Ile Arg Asp Lys Asp Ser Ser Asn Asp Trp Arg Leu Ala Lys Phe Ser
625                 630                 635                 640

Pro Lys Asn Leu Asp Glu Phe Ile Leu Ser Glu Asn Lys Ile Met Pro
                645                 650                 655
```

Phe Thr Ser Phe Ser Val Arg Lys Asn Phe Ile Tyr Leu Gln Asp Glu
660 665 670

Phe Lys Ser Leu Val Ile Leu Asp Val Asn Thr Leu Lys Lys Val Lys
675 680 685

<210> SEQ ID NO 29
<211> LENGTH: 594
<212> TYPE: PRT
<213> ORGANISM: Borrelia burgdorferi B31

<400> SEQUENCE: 29

Met Lys Glu Lys Asp Ile Phe Lys Ile Asn Pro Trp Met Pro Thr Phe
1 5 10 15

Gly Phe Glu Asn Thr Ser Glu Phe Arg Leu Asp Met Asp Glu Leu Val
20 25 30

Pro Gly Phe Glu Asn Lys Ser Lys Ile Thr Ile Lys Leu Lys Pro Phe
35 40 45

Glu Ala Asn Pro Glu Leu Gly Lys Asp Asp Pro Phe Ser Ala Tyr Ile
50 55 60

Lys Val Glu Asp Leu Ala Leu Lys Ala Glu Gly Lys Lys Gly Asp Gln
65 70 75 80

Phe Lys Ile Asp Val Gly Asp Ile Thr Ala Gln Ile Asn Met Tyr Asp
85 90 95

Phe Phe Ile Lys Ile Ser Thr Met Thr Asp Phe Asp Phe Asn Lys Glu
100 105 110

Ser Leu Phe Ser Phe Ala Pro Met Thr Gly Phe Lys Ser Thr Tyr Tyr
115 120 125

Gly Phe Pro Ser Asn Asp Arg Ala Val Arg Gly Thr Ile Leu Ala Arg
130 135 140

Gly Thr Ser Lys Asn Ile Gly Thr Ile Gln Leu Gly Tyr Lys Leu Pro
145 150 155 160

Lys Leu Asp Leu Thr Phe Ala Ile Gly Gly Thr Gly Thr Gly Asn Arg
165 170 175

Asn Gln Glu Asn Asp Lys Asp Thr Pro Tyr Asn Lys Thr Tyr Gln Gly
180 185 190

Ile Leu Tyr Gly Ile Gln Ala Thr Trp Lys Pro Ile Lys Asn Leu Leu
195 200 205

Asp Gln Asn Glu Asp Thr Lys Ser Val Ile Ala Glu Thr Pro Phe Glu
210 215 220

Leu Asn Phe Gly Leu Ser Gly Ala Tyr Gly Asn Glu Thr Phe Asn Asn
225 230 235 240

Ser Ser Ile Thr Tyr Ser Leu Lys Asp Lys Ser Val Val Gly Asn Asp
245 250 255

Leu Leu Ser Pro Thr Leu Ser Asn Ser Ala Ile Leu Ala Ser Phe Gly
260 265 270

Ala Lys Tyr Lys Leu Gly Leu Thr Lys Ile Asn Asp Lys Asn Thr Tyr
275 280 285

Leu Ile Leu Gln Met Gly Thr Asp Phe Gly Ile Asp Pro Phe Ala Ser
290 295 300

Asp Phe Ser Ile Phe Gly His Ile Ser Lys Ala Ala Asn Phe Lys Lys
305 310 315 320

Glu Thr Pro Ser Asp Pro Asn Lys Lys Ala Glu Ile Phe Asp Pro Asn
325 330 335

Gly Asn Ala Leu Asn Phe Ser Lys Asn Thr Glu Leu Gly Ile Ala Phe
340 345 350

```
Ser Thr Gly Ala Ser Ile Gly Phe Ala Trp Asn Lys Asp Thr Gly Glu
        355                 360                 365

Lys Glu Ser Trp Ala Ile Lys Gly Ser Asp Ser Tyr Ser Thr Arg Leu
    370                 375                 380

Phe Gly Glu Gln Asp Lys Lys Ser Gly Val Ala Leu Gly Ile Ser Tyr
385                 390                 395                 400

Gly Gln Asn Leu Tyr Arg Ser Lys Asp Thr Glu Lys Arg Leu Lys Thr
                405                 410                 415

Ile Ser Glu Asn Ala Phe Gln Ser Leu Asn Val Glu Ile Ser Ser Tyr
            420                 425                 430

Glu Asp Asn Lys Lys Gly Ile Ile Asn Gly Leu Gly Trp Ile Thr Ser
        435                 440                 445

Ile Gly Leu Tyr Asp Ile Leu Arg Gln Lys Ser Val Glu Asn Tyr Pro
    450                 455                 460

Thr Thr Ile Ser Ser Thr Thr Glu Asn Asn Gln Thr Glu Gln Ser Ser
465                 470                 475                 480

Thr Ser Thr Lys Thr Thr Thr Pro Asn Leu Thr Phe Glu Asp Ala Met
                485                 490                 495

Lys Leu Gly Leu Ala Leu Tyr Leu Asp Tyr Ala Ile Pro Ile Ala Ser
            500                 505                 510

Ile Ser Thr Glu Ala Tyr Val Val Pro Tyr Ile Gly Ala Tyr Ile Leu
        515                 520                 525

Gly Pro Ser Asn Lys Leu Ser Ser Asp Ala Thr Lys Ile Tyr Leu Lys
    530                 535                 540

Thr Gly Leu Ser Leu Glu Lys Leu Ile Arg Phe Thr Thr Ile Ser Leu
545                 550                 555                 560

Gly Trp Asp Ser Asn Asn Ile Ile Glu Leu Ala Asn Lys Asn Thr Asn
                565                 570                 575

Asn Ala Ala Ile Gly Ser Ala Phe Leu Gln Phe Lys Ile Ala Tyr Ser
            580                 585                 590

Gly Ser
```

<210> SEQ ID NO 30
<211> LENGTH: 508
<212> TYPE: PRT
<213> ORGANISM: Borrelia burgdorferi B31

<400> SEQUENCE: 30

```
Met Lys Glu Arg Lys Glu Gly Val Ser Phe Lys Ile Ser Leu Gly Ala
1               5                   10                  15

Glu Pro Ser Ser Leu Asp Pro Gln Leu Ala Glu Asp Asn Val Ala Ser
            20                  25                  30

Lys Met Ile Asp Thr Met Phe Arg Gly Ile Val Thr Gly Asp Pro Asn
        35                  40                  45

Thr Gly Gly Asn Lys Pro Gly Leu Ala Lys Gly Trp Asp Ile Ser Ser
    50                  55                  60

Asp Gly Thr Val Tyr Thr Phe Asn Leu Arg Glu Lys Ile Thr Trp Ser
65                  70                  75                  80

Asp Gly Val Ala Ile Thr Ala Glu Gly Ile Arg Lys Ser Tyr Leu Arg
                85                  90                  95

Ile Leu Asn Lys Glu Thr Gly Ser Lys Tyr Val Glu Met Val Lys Ser
            100                 105                 110

Val Ile Lys Asn Gly Gln Lys Tyr Phe Asp Gly Gln Val Thr Asp Ser
        115                 120                 125
```

```
Glu Leu Gly Ile Arg Ala Ile Asp Glu Lys Thr Leu Glu Ile Thr Leu
    130                 135                 140

Glu Ser Pro Lys Pro Tyr Phe Ile Asp Met Leu Val His Gln Ser Phe
145                 150                 155                 160

Ile Pro Val Pro Val His Val Thr Glu Lys Tyr Gly Gln Asn Trp Thr
                165                 170                 175

Ser Pro Glu Asn Met Val Thr Ser Gly Pro Phe Lys Leu Lys Glu Arg
            180                 185                 190

Ile Pro Asn Glu Lys Tyr Val Phe Glu Lys Asn Asn Lys Tyr Tyr Asp
        195                 200                 205

Ser Asn Glu Val Glu Leu Glu Glu Ile Thr Phe Tyr Thr Thr Asn Asp
    210                 215                 220

Ser Ser Thr Ala Tyr Lys Met Tyr Glu Asn Glu Glu Leu Asp Ala Ile
225                 230                 235                 240

Phe Gly Ser Ile Pro Pro Asp Leu Ile Lys Asn Leu Lys Leu Arg Ser
                245                 250                 255

Asp Tyr Tyr Ser Ser Ala Val Asn Ala Ile Tyr Phe Tyr Ala Phe Asn
            260                 265                 270

Thr His Ile Lys Pro Leu Asp Asn Val Lys Ile Arg Lys Ala Leu Thr
        275                 280                 285

Leu Ala Ile Asp Arg Glu Thr Leu Thr Tyr Lys Val Leu Asp Asn Gly
    290                 295                 300

Thr Thr Pro Thr Arg Arg Ala Thr Pro Asn Phe Ser Ser Tyr Ser Tyr
305                 310                 315                 320

Ala Lys Ser Leu Glu Leu Phe Asn Pro Glu Ile Ala Lys Thr Leu Leu
                325                 330                 335

Ala Glu Ala Gly Tyr Pro Asn Gly Asn Gly Phe Pro Ile Leu Lys Leu
            340                 345                 350

Lys Tyr Asn Thr Asn Glu Ala Asn Lys Lys Ile Cys Glu Phe Ile Gln
        355                 360                 365

Asn Gln Trp Lys Lys Asn Leu Asn Ile Asp Val Glu Leu Glu Asn Glu
    370                 375                 380

Glu Trp Thr Thr Tyr Leu Asn Thr Lys Ala Asn Gly Asn Tyr Glu Ile
385                 390                 395                 400

Ala Arg Ala Gly Trp Ile Gly Asp Tyr Ala Asp Pro Leu Thr Phe Leu
                405                 410                 415

Ser Ile Phe Thr Gln Gly Tyr Thr Gln Phe Ser Ser His Asn Tyr Ser
            420                 425                 430

Asn Pro Glu Tyr Asn Glu Leu Ile Lys Lys Ser Asp Leu Glu Leu Asp
        435                 440                 445

Pro Ile Lys Arg Gln Asp Ile Leu Arg Gln Ala Glu Glu Ile Ile Ile
    450                 455                 460

Glu Lys Asp Phe Pro Ile Ala Pro Ile Tyr Ile Tyr Gly Asn Ser Tyr
465                 470                 475                 480

Leu Phe Arg Asn Asp Lys Trp Thr Gly Trp Asn Thr Asn Ile Leu Glu
                485                 490                 495

Arg Phe Asp Leu Ser Gln Leu Lys Leu Lys Asn Lys
            500                 505
```

<210> SEQ ID NO 31
<211> LENGTH: 331
<212> TYPE: PRT
<213> ORGANISM: Borrelia burgdorferi B31

<400> SEQUENCE: 31

Met Arg Tyr Glu Met Lys Glu Glu Ser Pro Gly Leu Phe Asp Lys Gly
1 5 10 15

Asn Ser Ile Leu Glu Thr Ser Glu Glu Ser Ile Lys Lys Pro Met Asn
20 25 30

Lys Lys Gly Lys Gly Lys Ile Ala Arg Lys Lys Gly Lys Ser Lys Val
35 40 45

Ser Arg Lys Glu Pro Tyr Ile His Ser Leu Lys Arg Asp Ser Ala Asn
50 55 60

Lys Ser Asn Phe Leu Gln Lys Asn Val Ile Leu Glu Glu Glu Ser Leu
65 70 75 80

Lys Thr Glu Leu Leu Lys Glu Gln Ser Glu Thr Arg Lys Glu Lys Ile
85 90 95

Gln Lys Gln Gln Asp Glu Tyr Lys Gly Met Thr Gln Gly Ser Leu Asn
100 105 110

Ser Leu Ser Gly Glu Ser Gly Glu Leu Glu Glu Pro Ile Glu Ser Asn
115 120 125

Glu Ile Asp Leu Thr Ile Asp Ser Asp Leu Arg Pro Lys Ser Ser Leu
130 135 140

Gln Gly Ile Ala Gly Ser Asn Ser Ile Ser Tyr Thr Asp Glu Ile Glu
145 150 155 160

Glu Glu Asp Tyr Asp Gln Tyr Tyr Leu Asp Glu Tyr Asp Glu Glu Asp
165 170 175

Glu Glu Glu Ile Arg Leu Ser Asn Arg Tyr Gln Ser Tyr Leu Glu Gly
180 185 190

Val Lys Tyr Asn Val Asp Ser Ala Ile Gln Thr Ile Thr Lys Ile Tyr
195 200 205

Asn Thr Tyr Thr Leu Phe Ser Thr Lys Leu Thr Gln Met Tyr Ser Thr
210 215 220

Arg Leu Asp Asn Phe Ala Lys Ala Lys Ala Lys Glu Glu Ala Ala Lys
225 230 235 240

Phe Thr Lys Glu Asp Leu Glu Lys Asn Phe Lys Thr Leu Leu Asn Tyr
245 250 255

Ile Gln Val Ser Val Lys Thr Ala Ala Asn Phe Val Tyr Ile Asn Asp
260 265 270

Thr His Ala Lys Arg Lys Leu Glu Asn Ile Glu Ala Glu Ile Lys Thr
275 280 285

Leu Ile Ala Lys Ile Lys Glu Gln Ser Asn Leu Tyr Glu Ala Tyr Lys
290 295 300

Ala Ile Val Thr Ser Ile Leu Leu Met Arg Asp Ser Leu Lys Glu Val
305 310 315 320

Gln Gly Ile Ile Asp Lys Asn Gly Val Trp Tyr
325 330

<210> SEQ ID NO 32
<211> LENGTH: 324
<212> TYPE: PRT
<213> ORGANISM: Borrelia burgdorferi B31

<400> SEQUENCE: 32

Met Arg Asn Asn Gly Ile Asn Ala Ala Asn Leu Ser Lys Thr Gln Glu
1 5 10 15

Lys Leu Ser Ser Gly Tyr Arg Ile Asn Arg Ala Ser Asp Asp Ala Ala
20 25 30

-continued

```
Gly Met Gly Val Ser Gly Lys Ile Asn Ala Gln Ile Arg Gly Leu Ser
        35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Lys Val Leu Val Arg Met Lys Glu
65                  70                  75                  80

Leu Ala Val Gln Ser Gly Asn Gly Thr Tyr Ser Asp Ala Asp Arg Gly
                85                  90                  95

Ser Ile Gln Ile Glu Ile Glu Gln Leu Thr Asp Glu Ile Asn Arg Ile
            100                 105                 110

Ala Asp Gln Ala Gln Tyr Asn Gln Met His Met Leu Ser Asn Lys Ser
        115                 120                 125

Ala Ser Gln Asn Val Arg Thr Ala Glu Glu Leu Gly Met Gln Pro Ala
    130                 135                 140

Lys Ile Asn Thr Pro Ala Ser Leu Ser Gly Ser Gln Ala Ser Trp Thr
145                 150                 155                 160

Leu Arg Val His Val Gly Ala Asn Gln Asp Glu Ala Ile Ala Val Asn
                165                 170                 175

Ile Tyr Ala Ala Asn Val Ala Asn Leu Phe Ser Gly Glu Gly Ala Gln
            180                 185                 190

Thr Ala Gln Ala Ala Pro Val Gln Glu Gly Val Gln Gln Glu Gly Ala
        195                 200                 205

Gln Gln Pro Ala Pro Ala Thr Ala Pro Ser Gln Gly Gly Val Asn Ser
    210                 215                 220

Pro Val Asn Val Thr Thr Thr Val Asp Ala Asn Thr Ser Leu Ala Lys
225                 230                 235                 240

Ile Glu Asn Ala Ile Arg Met Ile Ser Asp Gln Arg Ala Asn Leu Gly
                245                 250                 255

Ala Phe Gln Asn Arg Leu Glu Ser Ile Lys Asn Ser Thr Glu Tyr Ala
            260                 265                 270

Ile Glu Asn Leu Lys Ala Ser Tyr Ala Gln Ile Lys Asp Ala Thr Met
        275                 280                 285

Thr Asp Glu Val Val Ala Ala Thr Thr Asn Ser Ile Leu Thr Gln Ser
    290                 295                 300

Ala Met Ala Met Ile Ala Gln Ala Asn Gln Val Pro Gln Tyr Val Leu
305                 310                 315                 320

Ser Leu Leu Arg


<210> SEQ ID NO 33
<211> LENGTH: 324
<212> TYPE: PRT
<213> ORGANISM: Borrelia mayonii

<400> SEQUENCE: 33

Met Arg Asn Asn Gly Ile Asn Ala Ala Asn Leu Ser Lys Thr Gln Glu
1               5                   10                  15

Lys Leu Ser Ser Gly Tyr Arg Ile Asn Arg Ala Ser Asp Asp Ala Ala
            20                  25                  30

Gly Met Gly Val Ser Gly Lys Ile Asn Ala Gln Ile Arg Gly Leu Ser
        35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Lys Val Leu Val Arg Met Lys Glu
65                  70                  75                  80
```

```
Leu Ala Val Gln Ser Gly Asn Gly Thr Tyr Ser Asp Ala Asp Arg Gly
                85                  90                  95

Ser Ile Gln Ile Glu Ile Glu Gln Leu Thr Asp Glu Ile Asn Arg Ile
            100                 105                 110

Ala Asp Gln Ala Gln Tyr Asn Gln Met His Met Leu Ser Asn Lys Ser
        115                 120                 125

Ala Ser Gln Asn Val Arg Thr Ala Glu Glu Leu Gly Met Gln Pro Ala
    130                 135                 140

Lys Ile Asn Thr Pro Ser Ser Leu Ser Gly Ser Gln Ala Ser Trp Thr
145                 150                 155                 160

Leu Arg Val His Val Gly Ala Asn Gln Asp Glu Ala Ile Ala Val Asn
                165                 170                 175

Ile Tyr Ala Ala Asn Val Ala Asn Leu Phe Ser Gly Glu Gly Thr Gln
            180                 185                 190

Thr Ala Gln Val Ala Pro Val Gln Glu Gly Ala Gln Gln Glu Gly Ala
        195                 200                 205

Gln Gln Pro Ala Pro Ala Thr Ala Pro Ser Gln Gly Gly Val Asn Ser
    210                 215                 220

Pro Val Asn Val Thr Thr Thr Val Asp Ala Asn Thr Ser Leu Ala Lys
225                 230                 235                 240

Ile Glu Asn Ala Ile Arg Met Ile Ser Asp Gln Arg Ala Asn Leu Gly
                245                 250                 255

Ala Phe Gln Asn Arg Leu Glu Ser Ile Lys Asn Ser Thr Glu Tyr Ala
            260                 265                 270

Ile Glu Asn Leu Lys Ala Ser Tyr Ala Gln Ile Lys Asp Ala Thr Met
        275                 280                 285

Thr Asp Glu Val Val Ala Ala Thr Thr Asn Ser Ile Leu Thr Gln Ser
    290                 295                 300

Ala Met Ala Met Ile Ala Gln Ala Asn Gln Val Pro Gln Tyr Val Leu
305                 310                 315                 320

Ser Leu Leu Arg


<210> SEQ ID NO 34
<211> LENGTH: 284
<212> TYPE: PRT
<213> ORGANISM: Borrelia burgdorferi B31

<400> SEQUENCE: 34

Met Gly Ser Cys Ala Gln Lys Gly Ala Glu Ser Ile Gly Ser Gln Lys
1               5                   10                  15

Glu Asn Asp Leu Asn Leu Glu Asp Ser Ser Lys Lys Ser His Gln Asn
            20                  25                  30

Ala Lys Gln Asp Leu Pro Ala Val Thr Glu Asp Ser Val Ser Leu Phe
        35                  40                  45

Asn Gly Asn Lys Ile Phe Val Ser Lys Glu Lys Asn Ser Ser Gly Lys
    50                  55                  60

Tyr Asp Leu Arg Ala Thr Ile Asp Gln Val Glu Leu Lys Gly Thr Ser
65                  70                  75                  80

Asp Lys Asn Asn Gly Ser Gly Thr Leu Glu Gly Ser Lys Pro Asp Lys
                85                  90                  95

Ser Lys Val Lys Leu Thr Val Ser Ala Asp Leu Asn Thr Val Thr Leu
            100                 105                 110

Glu Ala Phe Asp Ala Ser Asn Gln Lys Ile Ser Ser Lys Val Thr Lys
        115                 120                 125
```

```
Lys Gln Gly Ser Ile Thr Glu Glu Thr Leu Lys Ala Asn Lys Leu Asp
    130                 135                 140

Ser Lys Lys Leu Thr Arg Ser Asn Gly Thr Thr Leu Glu Tyr Ser Gln
145                 150                 155                 160

Ile Thr Asp Ala Asp Asn Ala Thr Lys Ala Val Glu Thr Leu Lys Asn
                165                 170                 175

Ser Ile Lys Leu Glu Gly Ser Leu Val Gly Gly Lys Thr Thr Val Glu
            180                 185                 190

Ile Lys Glu Gly Thr Val Thr Leu Lys Arg Glu Ile Glu Lys Asp Gly
        195                 200                 205

Lys Val Lys Val Phe Leu Asn Asp Thr Ala Gly Ser Asn Lys Lys Thr
    210                 215                 220

Gly Lys Trp Glu Asp Ser Thr Ser Thr Leu Thr Ile Ser Ala Asp Ser
225                 230                 235                 240

Lys Lys Thr Lys Asp Leu Val Phe Leu Thr Asp Gly Thr Ile Thr Val
                245                 250                 255

Gln Gln Tyr Asn Thr Ala Gly Thr Ser Leu Glu Gly Ser Ala Ser Glu
            260                 265                 270

Ile Lys Asn Leu Ser Glu Leu Lys Asn Ala Leu Lys
        275                 280


<210> SEQ ID NO 35
<211> LENGTH: 296
<212> TYPE: PRT
<213> ORGANISM: Borrelia burgdorferi 297

<400> SEQUENCE: 35

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Gln Lys Glu Asn Asp Leu
            20                  25                  30

Asn Leu Glu Asp Ser Ser Lys Lys Ser His Gln Asn Ala Lys Gln Asp
        35                  40                  45

Leu Pro Ala Val Thr Glu Asp Ser Val Ser Leu Phe Asn Gly Asn Lys
    50                  55                  60

Ile Phe Val Ser Lys Glu Lys Asn Ser Ser Gly Lys Tyr Asp Leu Arg
65                  70                  75                  80

Ala Thr Ile Asp Gln Val Glu Leu Lys Gly Thr Ser Asp Lys Asn Asn
                85                  90                  95

Gly Ser Gly Thr Leu Glu Gly Ser Lys Pro Asp Lys Ser Lys Val Lys
            100                 105                 110

Leu Thr Val Ser Ala Asp Leu Asn Thr Val Thr Leu Glu Ala Phe Asp
        115                 120                 125

Ala Ser Asn Gln Lys Ile Ser Ser Lys Val Thr Lys Lys Gln Gly Ser
    130                 135                 140

Ile Thr Glu Glu Thr Leu Lys Ala Asn Lys Leu Asp Ser Lys Lys Leu
145                 150                 155                 160

Thr Arg Ser Asn Gly Thr Thr Leu Glu Tyr Ser Gln Ile Thr Asp Ala
                165                 170                 175

Asp Asn Ala Thr Lys Ala Val Glu Thr Leu Lys Asn Ser Ile Lys Leu
            180                 185                 190

Glu Gly Ser Leu Val Gly Gly Lys Thr Thr Val Glu Ile Lys Glu Gly
        195                 200                 205

Thr Val Thr Leu Lys Arg Glu Ile Glu Lys Asp Gly Lys Val Lys Val
    210                 215                 220
```

```
Phe Leu Asn Asp Thr Ala Gly Ser Asn Lys Lys Thr Gly Lys Trp Glu
225                 230                 235                 240

Asp Ser Thr Ser Thr Leu Thr Ile Ser Ala Asp Ser Thr Lys Thr Lys
                245                 250                 255

Asp Leu Val Phe Leu Thr Asp Gly Thr Ile Thr Val Gln Gln Tyr Asn
            260                 265                 270

Thr Ala Gly Thr Ser Leu Glu Gly Ser Ala Ser Glu Ile Lys Asn Leu
        275                 280                 285

Ser Glu Leu Lys Asn Ala Leu Lys
    290                 295


<210> SEQ ID NO 36
<211> LENGTH: 295
<212> TYPE: PRT
<213> ORGANISM: Borrelia valaisiana

<400> SEQUENCE: 36

Met Arg Gln Tyr Leu Ile Gly Phe Ala Leu Val Leu Ala Leu Leu Ala
1               5                   10                  15

Cys Ala Gln Lys Gly Ala Glu Pro Lys Thr Gln Asn Ser Asp Arg Glu
            20                  25                  30

Ile Met Asp Ser Asn Lys Asp Ser Ser Lys Asp Ser Lys Gln Val Leu
        35                  40                  45

Thr Thr Ser Thr Glu Lys Ala Val Ser Leu Phe Asn Gly Tyr Thr Ile
    50                  55                  60

Phe Val Ser Lys Glu Lys Asn Thr Ser Gly Lys Tyr Asp Leu Arg Ala
65                  70                  75                  80

Val Val Asp Gln Phe Glu Leu Lys Gly Thr Ser Asp Lys Asp Asn Gly
                85                  90                  95

Ser Gly Thr Leu Lys Gly Ser Lys Ala Asp Lys Thr Lys Met Thr Ile
            100                 105                 110

Ser Ile Thr Glu Asp Leu Asn Ser Val Thr Val Glu Thr Phe Asp Ser
        115                 120                 125

Gly Asn Lys Lys Val Ser Ser Lys Val Val Lys Lys His Gly Leu Leu
    130                 135                 140

Thr Glu Glu Asn Phe Lys Ala Asp Lys Leu Asp Ser Gln Lys Leu Thr
145                 150                 155                 160

Arg Ser Asn Gly Thr Thr Leu Glu Tyr Ser Gln Met Thr Asp Ala Glu
                165                 170                 175

Asn Ala Thr Lys Ala Val Glu Thr Leu Lys Asn Gly Ile Lys Leu Glu
            180                 185                 190

Gly Asn Leu Val Gly Gly Lys Thr Thr Leu Lys Ile Thr Val Gly Thr
        195                 200                 205

Val Thr Leu Thr Arg Glu Ile Glu Lys Asp Gly Arg Ile Lys Leu Phe
    210                 215                 220

Leu Asn Asp Thr Asp Ser Ser Pro Thr Lys Lys Thr Ala Lys Trp Glu
225                 230                 235                 240

Asp Ser Thr Asn Thr Leu Thr Ile Thr Ser Asn Arg Lys Lys Thr Lys
                245                 250                 255

Asp Leu Val Phe Leu Ile Asp Gly Thr Ile Thr Val Gln Asn Tyr Asn
            260                 265                 270

Ser Ala Gly Lys Leu Asp Gly Gln Ala Ser Glu Ile Lys Ser Leu Gly
        275                 280                 285

Glu Leu Gln Gly Ala Leu Lys
```

290 295

<210> SEQ ID NO 37
<211> LENGTH: 299
<212> TYPE: PRT
<213> ORGANISM: Borrelia spielmanii

<400> SEQUENCE: 37

Met Arg Gln Gln Tyr Leu Leu Val Phe Ala Leu Ile Leu Ala Leu Ile
1 5 10 15

Ala Cys Ser Gln Lys Gly Thr Glu Pro Lys Asp Asp Asn Tyr Asn Asp
20 25 30

Gln Glu Ile Ala Ser Gly Asp Lys Glu Pro Lys Ile Ser Lys Lys Glu
35 40 45

Leu Pro Arg Glu Thr Glu Thr Ala Val Ser Leu Phe Asn Gly Asn Glu
50 55 60

Ile Phe Ile Ser Lys Glu Lys Asn Ser Ala Gly Lys Tyr Asp Leu Arg
65 70 75 80

Ala Arg Val Asp Leu Val Glu Leu Lys Gly Thr Ser Asp Lys Asn Thr
85 90 95

Gly Ala Gly Lys Leu Glu Gly Leu Lys Ala Asp Lys Ser Lys Val Thr
100 105 110

Met Thr Ile Ser Asp Asp Leu Asn Thr Val Thr Val Glu Thr Tyr Asp
115 120 125

Ala Ser Asn Lys Lys Thr Gly Ser Glu Val Val Lys Lys Gln Gly Ser
130 135 140

Val Ile Lys Glu Ser Tyr Lys Ala Asn Lys Leu Asp Ser Lys Lys Leu
145 150 155 160

Thr Arg Ser Asn Asp Thr Thr Leu Glu Tyr Ser Gln Met Thr Asp Glu
165 170 175

Glu Asn Ala Thr Lys Ala Val Glu Thr Leu Lys Asn Gly Ile Lys Phe
180 185 190

Glu Gly Asn Leu Val Gly Gly Lys Thr Thr Val Lys Ile Thr Glu Gly
195 200 205

Thr Val Thr Leu Lys Arg Glu Ile Asp Lys Asp Gly Lys Ile Lys Val
210 215 220

Phe Leu Asp Asp Thr Ala Thr Asp Asn Thr Lys Lys Thr Gly Lys Trp
225 230 235 240

Asn Glu Asn Asn Asn Thr Leu Thr Val Thr Val Asp Ser Lys Lys Thr
245 250 255

Lys Asp Leu Val Phe Ser Asp Asp Gly Thr Ser Thr Ile Thr Val Gln
260 265 270

Lys Tyr Asn Thr Ala Gly Thr Asn Leu Glu Gly Asn Pro Ser Glu Ile
275 280 285

Lys Asp Leu Ala Ala Leu Lys Gly Ala Leu Lys
290 295

<210> SEQ ID NO 38
<211> LENGTH: 293
<212> TYPE: PRT
<213> ORGANISM: Borrelia garinii

<400> SEQUENCE: 38

Met Lys Lys Tyr Leu Leu Gly Phe Ala Leu Val Leu Ala Leu Ile Ala
1 5 10 15

Cys Gly Gln Lys Gly Ala Glu Pro Lys His Asn Asp Gln Glu Val Glu

```
            20                  25                  30

Asp Ser Lys Lys Asp Gln Lys Asp Ala Ser Lys Lys Asp Leu Pro Leu
        35                  40                  45

Val Thr Glu Asp Thr Val Lys Leu Phe Asn Asp Thr Glu Ile Phe Ile
    50                  55                  60

Ser Lys Glu Lys Asn Asn Ala Gly Lys Tyr Glu Leu Arg Ala Met Val
65                  70                  75                  80

Asp Thr Val Glu Leu Lys Gly Phe Ser Glu Lys Asn Thr Gly Ala Gly
                85                  90                  95

Asn Leu Glu Gly Leu Lys Ala Asp Lys Ser Lys Val Thr Met Leu Val
            100                 105                 110

Ser Asp Asp Leu Asn Thr Ile Thr Ile Glu Thr Tyr Asn Thr Ser Asn
        115                 120                 125

Lys Lys Val Ser Ser Gln Val Val Lys Lys Gln Gly Leu Leu Thr Glu
    130                 135                 140

Glu Ser Tyr Lys Ala Asp Lys Leu Asp Ser Lys Lys Leu Thr Arg Thr
145                 150                 155                 160

Asn Gly Thr Thr Leu Glu Tyr Ser Asp Met Thr Asp Ala Ala Asn Ala
                165                 170                 175

Thr Lys Ala Val Glu Thr Leu Lys Asn Gly Ile Glu Phe Glu Gly Asn
            180                 185                 190

Leu Val Gly Gly Lys Thr Thr Leu Asn Ile Lys Glu Gly Thr Val Thr
        195                 200                 205

Leu Thr Arg Glu Ile Asp Lys Asp Asp Lys Leu Lys Ile Tyr Leu Asn
    210                 215                 220

Asp Thr Ala Ser Ser Ser Lys Lys Thr Ala Ser Trp Asn Asp Thr Asp
225                 230                 235                 240

Thr Leu Thr Ile Ser Ala Glu Gly Lys Lys Thr Lys Asp Leu Val Phe
                245                 250                 255

Arg Thr Asp Gly Thr Ile Thr Val Gln Asn Tyr Asp Ser Ala Ser Gly
            260                 265                 270

Thr Lys Leu Glu Gly Thr Ala Thr Glu Ile Lys Asp Leu Glu Ala Leu
        275                 280                 285

Lys Ala Ala Leu Lys
    290


<210> SEQ ID NO 39
<211> LENGTH: 299
<212> TYPE: PRT
<213> ORGANISM: Borrelia afzelii

<400> SEQUENCE: 39

Met Lys Gln Tyr Leu Leu Val Phe Ala Leu Val Leu Ala Leu Ile Ala
1               5                   10                  15

Cys Ser Gln Lys Gly Thr Glu Pro Lys Ser Thr Ser Gln Asp His Asn
            20                  25                  30

Asp Gln Glu Ile Ile Asn Ser Asp Asn Thr Pro Lys Asp Ser Lys Lys
        35                  40                  45

Asp Leu Thr Val Leu Ala Glu Glu Asn Ser Val Pro Leu Phe Asn Gly
    50                  55                  60

Asn Lys Ile Phe Val Ser Lys Glu Lys Asn Ser Ala Gly Lys Tyr Glu
65                  70                  75                  80

Leu Arg Ala Thr Val Asp Thr Val Glu Leu Lys Gly Val Ser Asp Lys
                85                  90                  95
```

Asn Asn Gly Ser Gly Lys Leu Glu Gly Thr Lys Ala Asp Lys Thr Lys
            100                 105                 110

Val Ala Met Thr Ile Ala Asp Asp Leu Asn Thr Ile Thr Val Glu Thr
        115                 120                 125

Tyr Asp Ala Ser Asn Lys Lys Thr Gly Ser Glu Val Val Lys Lys Gln
    130                 135                 140

Gly Ser Val Ile Lys Glu Ser Tyr Lys Ala Asn Lys Leu Asp Ser Lys
145                 150                 155                 160

Lys Ile Thr Arg Glu Asn Glu Thr Thr Leu Glu Tyr Ser Glu Met Thr
                165                 170                 175

Asp Ser Ser Asn Ala Thr Lys Ala Val Glu Thr Leu Lys Asn Gly Ile
            180                 185                 190

Lys Leu Glu Gly Ser Leu Val Gly Gly Lys Thr Thr Val Lys Leu Thr
        195                 200                 205

Glu Gly Thr Ile Thr Leu Thr Arg Glu Ile Glu Gln Asp Gly Lys Val
    210                 215                 220

Lys Ile Tyr Leu Asn Asp Thr Thr Ser Gly Ser Thr Lys Lys Thr Ala
225                 230                 235                 240

Thr Trp Asn Glu Thr Thr Asn Thr Leu Thr Ile Ser Ala Asp Ser Lys
                245                 250                 255

Lys Thr Lys Asp Phe Val Phe Leu Thr Asp Gly Thr Ile Thr Val Gln
            260                 265                 270

Ala Tyr Asp Thr Ala Gly Thr Lys Leu Glu Gly Asn Ser Ser Glu Ile
        275                 280                 285

Lys Asp Leu Ala Ala Leu Lys Ala Ala Leu Lys
    290                 295

<210> SEQ ID NO 40
<211> LENGTH: 246
<212> TYPE: PRT
<213> ORGANISM: Borrelia burgdorferi B31

<400> SEQUENCE: 40

Met Phe Leu Leu Leu Ser Ile Ser Cys Val His Asp Lys Gln Glu Leu
1               5                   10                  15

Ser Ser Lys Ser Asn Leu Asn Asn Gln Lys Gly Tyr Leu Asp Asn Glu
            20                  25                  30

Gly Ala Asn Ser Asn Tyr Glu Ser Lys Lys Gln Ser Ile Leu Ser Glu
        35                  40                  45

Leu Asn Gln Leu Leu Lys Gln Thr Thr Asn Ser Leu Lys Glu Ala Lys
    50                  55                  60

Asn Thr Thr Asp Asn Leu Asn Ala Ser Asn Glu Ala Asn Lys Val Val
65                  70                  75                  80

Glu Ala Val Ile Asn Ala Val Asn Leu Ile Ser Ser Ala Ala Asp Gln
                85                  90                  95

Val Lys Ser Ala Thr Lys Asn Met His Asp Leu Ala Gln Met Ala Glu
            100                 105                 110

Ile Asp Leu Glu Lys Ile Lys Asn Ser Ser Asp Lys Ala Ile Phe Ala
        115                 120                 125

Ser Asn Leu Ala Lys Glu Ala Tyr Ser Leu Thr Lys Ala Ala Glu Gln
    130                 135                 140

Asn Met Gln Lys Leu Tyr Lys Glu Gln Gln Lys Ile Ser Glu Ser Glu
145                 150                 155                 160

Ser Glu Ser Asp Tyr Ser Asp Ser Ala Glu Ile Lys Gln Ala Lys Glu
                165                 170                 175

```
Ala Val Glu Ile Ala Trp Lys Ala Thr Val Glu Ala Lys Asp Lys Leu
            180                 185                 190

Ile Asp Val Glu Asn Thr Val Lys Glu Thr Leu Asp Lys Ile Lys Thr
        195                 200                 205

Glu Thr Thr Asn Asn Thr Lys Leu Ala Asp Ile Lys Glu Ala Ala Glu
    210                 215                 220

Leu Val Leu Gln Ile Ala Lys Asn Ala Lys Glu Ile Val Gln Glu Val
225                 230                 235                 240

Val Ala Leu Leu Asn Thr
                245


<210> SEQ ID NO 41
<211> LENGTH: 201
<212> TYPE: PRT
<213> ORGANISM: Borrelia burgdorferi B31

<400> SEQUENCE: 41

Met Thr Ser Lys Asp Leu Glu Gly Ala Val Lys Asp Leu Glu Ser Ser
1               5                   10                  15

Glu Gln Asn Val Lys Lys Thr Glu Gln Glu Ile Lys Lys Gln Val Glu
            20                  25                  30

Gly Phe Leu Glu Ile Leu Glu Thr Lys Asp Leu Asn Thr Leu Asp Thr
        35                  40                  45

Lys Glu Ile Glu Lys Gln Ile Gln Glu Leu Lys Asn Lys Ile Glu Lys
    50                  55                  60

Leu Asp Ser Lys Lys Thr Ser Ile Glu Thr Tyr Ser Gly Tyr Glu Glu
65                  70                  75                  80

Lys Ile Asn Lys Ile Lys Glu Lys Leu Asn Gly Lys Gly Leu Glu Asp
                85                  90                  95

Lys Leu Asn Glu Leu Ser Glu Ser Leu Lys Lys Arg Lys Glu Glu Arg
            100                 105                 110

Lys Lys Ala Leu Gln Glu Ala Lys Lys Lys Phe Glu Glu Tyr Lys Asn
        115                 120                 125

Gln Ala Glu Ser Ala Thr Gly Val Thr His Gly Ser Gln Val Gln Arg
    130                 135                 140

Gln Gly Gly Val Gly Leu Gln Ala Trp Gln Cys Ala Asn Ser Leu Gly
145                 150                 155                 160

Phe Lys Asn Met Thr Ser Gly Asn Asn Thr Ser Asp Met Thr Asn Glu
                165                 170                 175

Val Ile Thr Asn Ser Leu Lys Lys Ile Glu Glu Glu Leu Lys Asn Ile
            180                 185                 190

Gly Glu Thr Val Glu Gly Lys Lys Glu
        195                 200


<210> SEQ ID NO 42
<211> LENGTH: 206
<212> TYPE: PRT
<213> ORGANISM: Borrelia burgdorferi 297

<400> SEQUENCE: 42

Met Thr Ser Lys Asp Leu Glu Gly Val Val Gln Asp Leu Glu Ser Ser
1               5                   10                  15

Glu Gln Asn Val Lys Lys Thr Glu Gln Glu Ile Lys Lys Gln Val Glu
            20                  25                  30

Gly Phe Leu Glu Ile Leu Glu Thr Lys Asp Leu Asn Thr Leu Asp Thr
        35                  40                  45
```

```
Lys Glu Ile Glu Lys Gln Ile Gln Glu Leu Lys Asp Thr Ile Asn Lys
    50                  55                  60

Leu Glu Ala Lys Lys Thr Ser Leu Lys Thr Tyr Ser Glu Tyr Glu Glu
65                  70                  75                  80

Lys Leu Lys Gln Ile Lys Glu Lys Leu Lys Asp Lys Lys Glu Leu Glu
                85                  90                  95

Asp Lys Leu Lys Gly Leu Glu Asp Ser Leu Lys Lys Lys Lys Glu Asp
            100                 105                 110

Arg Lys Lys Ala Leu Glu Asp Ala Lys Lys Lys Phe Glu Glu Phe Lys
        115                 120                 125

Gly Gln Val Gly Ser Ala Thr Gly Val Thr Thr Gly His Arg Ala Gly
    130                 135                 140

Asn Gln Gly Ser Ile Gly Ala Gln Ala Trp Gln Cys Ala Asn Ser Leu
145                 150                 155                 160

Gly Leu Gly Val Ser Tyr Ser Ser Ser Thr Gly Thr Asp Ser Asn Glu
                165                 170                 175

Leu Ala Asn Lys Val Ile Asp Asp Ser Ile Lys Lys Ile Asp Glu Glu
            180                 185                 190

Leu Lys Asn Thr Ile Glu Asn Asn Gly Lys Val Lys Lys Glu
        195                 200                 205


<210> SEQ ID NO 43
<211> LENGTH: 161
<212> TYPE: PRT
<213> ORGANISM: Borrelia burgdorferi B31

<400> SEQUENCE: 43

Met Lys Ile Arg Leu Glu Arg Ser Ala Lys Asp Ile Thr Asp Glu Ile
1               5                   10                  15

Asp Ala Ile Lys Lys Asp Ala Ala Leu Lys Gly Val Asn Phe Asp Ala
            20                  25                  30

Phe Lys Asp Lys Lys Thr Gly Ser Gly Val Ser Glu Asn Pro Phe Ile
        35                  40                  45

Leu Glu Ala Lys Val Arg Ala Thr Thr Val Ala Glu Lys Phe Val Ile
    50                  55                  60

Ala Ile Glu Glu Glu Ala Thr Lys Leu Lys Glu Thr Gly Ser Ser Gly
65                  70                  75                  80

Glu Phe Ser Ala Met Tyr Asp Leu Met Phe Glu Val Ser Lys Pro Leu
                85                  90                  95

Gln Lys Leu Gly Ile Gln Glu Met Thr Lys Thr Val Ser Asp Ala Ala
            100                 105                 110

Glu Glu Asn Pro Pro Thr Thr Ala Gln Gly Val Leu Glu Ile Ala Lys
        115                 120                 125

Lys Met Arg Glu Lys Leu Gln Arg Val His Thr Lys Asn Tyr Cys Thr
    130                 135                 140

Leu Lys Lys Lys Glu Asn Ser Thr Phe Thr Asp Glu Lys Cys Lys Asn
145                 150                 155                 160

Asn


<210> SEQ ID NO 44
<211> LENGTH: 294
<212> TYPE: PRT
<213> ORGANISM: Borrelia burgdorferi B31

<400> SEQUENCE: 44
```

```
Met Asp Pro Lys Lys Ser Asp Val Lys Thr Tyr Phe Thr Thr Val Ala
1               5                   10                  15

Ala Lys Leu Glu Lys Thr Lys Thr Asp Leu Asn Ser Leu Pro Lys Glu
            20                  25                  30

Lys Ser Asp Ile Ser Ser Thr Thr Gly Lys Pro Asp Ser Thr Gly Ser
        35                  40                  45

Val Gly Thr Ala Val Glu Gly Ala Ile Lys Glu Val Ser Glu Leu Leu
    50                  55                  60

Asp Lys Leu Val Lys Ala Val Lys Thr Ala Glu Gly Ala Ser Ser Gly
65                  70                  75                  80

Thr Ala Ala Ile Gly Glu Val Val Ala Asp Ala Asp Ala Ala Lys Val
                85                  90                  95

Ala Asp Lys Ala Ser Val Lys Gly Ile Ala Lys Gly Ile Lys Glu Ile
            100                 105                 110

Val Glu Ala Ala Gly Gly Ser Glu Lys Leu Lys Ala Val Ala Ala Ala
        115                 120                 125

Lys Gly Glu Asn Asn Lys Gly Ala Gly Lys Leu Phe Gly Lys Ala Gly
    130                 135                 140

Ala Ala Ala His Gly Asp Ser Glu Ala Ala Ser Lys Ala Ala Gly Ala
145                 150                 155                 160

Val Ser Ala Val Ser Gly Glu Gln Ile Leu Ser Ala Ile Val Thr Ala
                165                 170                 175

Ala Asp Ala Ala Glu Gln Asp Gly Lys Lys Pro Glu Glu Ala Lys Asn
            180                 185                 190

Pro Ile Ala Ala Ala Ile Gly Asp Lys Asp Gly Gly Ala Glu Phe Gly
        195                 200                 205

Gln Asp Glu Met Lys Lys Asp Asp Gln Ile Ala Ala Ala Ile Ala Leu
    210                 215                 220

Arg Gly Met Ala Lys Asp Gly Lys Phe Ala Val Lys Asp Gly Glu Lys
225                 230                 235                 240

Glu Lys Ala Glu Gly Ala Ile Lys Gly Ala Ala Glu Ser Ala Val Arg
                245                 250                 255

Lys Val Leu Gly Ala Ile Thr Gly Leu Ile Gly Asp Ala Val Ser Ser
            260                 265                 270

Gly Leu Arg Lys Val Gly Asp Ser Val Lys Ala Ala Ser Lys Glu Thr
        275                 280                 285

Pro Pro Ala Leu Asn Lys
    290
```

<210> SEQ ID NO 45
<211> LENGTH: 143
<212> TYPE: PRT
<213> ORGANISM: Artificial Sequence
<220> FEATURE:
<223> OTHER INFORMATION: Synthetic Oligonucleotide

<400> SEQUENCE: 45

```
Met Lys Lys Asp Asp Gln Ile Ala Ala Ala Ile Ala Leu Arg Gly Met
1               5                   10                  15

Ala Lys Asp Gly Lys Phe Ala Val Lys Asp Gly Gly Gly Met Lys Lys
            20                  25                  30

Asn Asp Gln Ile Ala Ala Ala Ile Val Leu Arg Gly Met Ala Lys Asp
        35                  40                  45

Gly Glu Phe Ala Leu Lys Asn Glu Leu Gly Ser Met Lys Lys Asn Asp
    50                  55                  60
```

-continued

```
Gln Ile Ala Ala Ala Met Val Leu Arg Gly Met Ala Lys Asp Gly Gln
65                  70                  75                  80

Phe Ala Leu Thr Gly Gly Gly Gly Met Lys Lys Asp Asp Gln Ile Ala
                85                  90                  95

Ala Ala Ile Ala Leu Arg Gly Met Ala Lys Asp Gly Lys Phe Ala Val
            100                 105                 110

Lys Asp Gly Gly Gly Met Lys Lys Asp Ala Gln Ile Ala Ala Ala Ile
        115                 120                 125

Val Leu Arg Gly Met Ala Lys Asp Gly Lys Phe Ala Val Lys Lys
    130                 135                 140


<210> SEQ ID NO 46
<211> LENGTH: 110
<212> TYPE: PRT
<213> ORGANISM: Artificial Sequence
<220> FEATURE:
<223> OTHER INFORMATION: Synthetic Oligonucleotide

<400> SEQUENCE: 46

Met Pro Val Val Ala Glu Ser Pro Lys Lys Pro Gly Ser Pro Val Val
1               5                   10                  15

Ala Glu Thr Pro Lys Lys Pro Gly Ser Pro Val Val Ala Glu Ser Pro
            20                  25                  30

Lys Lys Pro Gly Ser Pro Ile Val Ala Glu Ser Pro Lys Asn Pro Gly
        35                  40                  45

Ser Pro Val Val Ala Glu Ser Pro Lys Lys Pro Gly Ser Pro Val Ala
    50                  55                  60

Ala Glu Ser Pro Lys Lys Pro Gly Ser Pro Val Val Ala Glu Ser Pro
65                  70                  75                  80

Lys Lys Pro Gly Ser Pro Val Val Ala Glu Thr Pro Lys Lys Pro Gly
                85                  90                  95

Ser Pro Val Val Ala Glu Ser Pro Lys Lys Pro Gly Ser Trp
            100                 105                 110


<210> SEQ ID NO 47
<211> LENGTH: 210
<212> TYPE: PRT
<213> ORGANISM: Borrelia spielmanii

<400> SEQUENCE: 47

Met Lys Lys Asn Thr Leu Ser Ala Ile Leu Met Thr Leu Phe Leu Phe
1               5                   10                  15

Ile Ser Cys Asn Asn Ser Gly Gly Asp Ser Thr Ser Thr Lys Pro Val
            20                  25                  30

Asp Glu Ser Ala Lys Gly Pro Asn Leu Thr Glu Ile Ser Lys Lys Ile
        35                  40                  45

Thr Asp Ser Asn Thr Phe Val Leu Ala Val Lys Glu Val Glu Thr Leu
    50                  55                  60

Leu Leu Ser Ile Asp Glu Leu Ala Lys Ala Ile Gly Lys Lys Ile Glu
65                  70                  75                  80

Asn Asn Gly Leu Gly Thr Glu Ala Ser His Asn Thr Ser Leu Leu Ala
                85                  90                  95

Gly Ala Tyr Thr Ile Ser Ser Leu Ile Thr Gln Lys Leu Asn Ala Leu
            100                 105                 110

Lys Asn Ser Gly Glu Leu Lys Ala Glu Ile Glu Lys Ala Lys Asn Cys
        115                 120                 125

Ser Glu Ala Phe Thr Lys Lys Leu Lys Glu Lys His Gln Asp Leu Gly
```

-continued

```
    130                 135                 140

Thr Ala Gly Gly Asn Ala Thr Asp Asp His Ala Lys Ala Ala Ile Leu
145                 150                 155                 160

Lys Thr Asn Ala Thr Asp Asp Lys Gly Ala Lys Glu Leu Lys Glu Leu
                165                 170                 175

Phe Glu Ser Val Glu Ser Leu Ser Lys Ala Ala Lys Ala Ala Leu Ala
            180                 185                 190

Asn Ser Val Lys Glu Leu Thr Ser Pro Val Val Ala Glu Thr Pro Lys
        195                 200                 205

Lys Pro
    210


<210> SEQ ID NO 48
<211> LENGTH: 212
<212> TYPE: PRT
<213> ORGANISM: Borrelia bissettii

<400> SEQUENCE: 48

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Ser Ala Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Ile Val Leu Ala Val Lys Glu Val Glu
    50                  55                  60

Thr Leu Leu Leu Ser Ile Asp Glu Leu Ala Lys Ala Ile Gly Lys Lys
65                  70                  75                  80

Ile Asn Asn Asn Gly Leu Asp Val Leu Gln Asn Phe Asn Ala Ser Leu
                85                  90                  95

Leu Gly Gly Ala His Thr Ile Ser Lys Leu Ile Thr Glu Lys Leu Ser
            100                 105                 110

Lys Leu Asn Gly Ser Glu Glu Leu Lys Glu Lys Ile Glu Ala Ala Lys
        115                 120                 125

Lys Cys Ser Asp Asp Phe Thr Lys Lys Leu Gln Ser Ser His Ala Glu
    130                 135                 140

Leu Gly Val Ala Gly Gly Ala Thr Thr Asp Glu Asn Ala Lys Lys Ala
145                 150                 155                 160

Ile Leu Lys Ser Asn Ala Asp Lys Thr Lys Gly Ala Asp Glu Leu Gly
                165                 170                 175

Lys Leu Phe Glu Ser Val Glu Ser Leu Ala Lys Ala Ala Lys Glu Met
            180                 185                 190

Leu Ala Asn Ser Val Lys Glu Leu Thr Ser Pro Val Val Ala Glu Thr
        195                 200                 205

Pro Lys Lys Pro
    210


<210> SEQ ID NO 49
<211> LENGTH: 211
<212> TYPE: PRT
<213> ORGANISM: Borrelia valaisiana

<400> SEQUENCE: 49

Met Lys Lys Asn Thr Leu Ser Ala Ile Leu Met Thr Leu Phe Leu Phe
1               5                   10                  15

Ile Ser Cys Asn Asn Ser Gly Lys Asp Val Thr Thr Ser Thr Asp Ser
```

-continued

```
            20                  25                  30

Val Asp Glu Ser Ala Lys Gly Pro Asn Leu Val Glu Ile Ser Lys Lys
        35                  40                  45

Ile Thr Asp Ser Asn Ala Ile Val Leu Ala Val Lys Glu Val Glu Thr
    50                  55                  60

Leu Leu Ser Ser Ile Asp Glu Leu Ala Asn Lys Ala Ile Gly Lys Lys
65                  70                  75                  80

Ile Gln Gln Asn Gly Ser Leu Ala Asn Glu Ala Asp His Asn Gly Ser
                85                  90                  95

Leu Leu Ala Gly Thr Tyr Ala Ile Ser Thr Leu Ile Thr Gln Lys Leu
            100                 105                 110

Gly Lys Leu Lys Ile Ser Glu Glu Leu Lys Glu Lys Ile Glu Asp Ala
        115                 120                 125

Lys Lys Cys Ser Glu Asp Phe Ala Arg Lys Leu Ser Asp Asn His Asn
    130                 135                 140

Asp Leu Gly Lys Glu Gly Val Thr Asp Asp Asp Ala Lys Lys Ala Ile
145                 150                 155                 160

Leu Lys Thr His Gly Thr Lys Asp Lys Gly Ala Ala Glu Phe Glu Lys
                165                 170                 175

Leu Phe Lys Ser Val Glu Ser Leu Val Lys Ala Ala Gln Glu Thr Leu
            180                 185                 190

Val Asn Ser Ile Lys Glu Leu Thr Ser Pro Val Ala Ala Glu Ser Pro
        195                 200                 205

Lys Lys Pro
    210


<210> SEQ ID NO 50
<211> LENGTH: 210
<212> TYPE: PRT
<213> ORGANISM: Borrelia burgdorferi B31

<400> SEQUENCE: 50

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175
```

-continued

```
Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210


<210> SEQ ID NO 51
<211> LENGTH: 211
<212> TYPE: PRT
<213> ORGANISM: Borrelia burgdorferi 297

<400> SEQUENCE: 51

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Ile Glu Thr
    50                  55                  60

Leu Leu Ala Ser Ile Asp Glu Leu Ala Thr Lys Ala Ile Gly Lys Lys
65                  70                  75                  80

Ile Gln Gln Asn Gly Gly Leu Ala Val Glu Ala Gly His Asn Gly Thr
                85                  90                  95

Leu Leu Ala Gly Ala Tyr Thr Ile Ser Lys Leu Ile Thr Gln Lys Leu
            100                 105                 110

Asp Gly Leu Lys Asn Ser Glu Lys Leu Lys Glu Lys Ile Glu Asn Ala
        115                 120                 125

Lys Lys Cys Ser Glu Asp Phe Thr Lys Lys Leu Glu Gly Glu His Ala
    130                 135                 140

Gln Leu Gly Ile Glu Asn Val Thr Asp Glu Asn Ala Lys Lys Ala Ile
145                 150                 155                 160

Leu Ile Thr Asp Ala Ala Lys Asp Lys Gly Ala Ala Glu Leu Glu Lys
                165                 170                 175

Leu Phe Lys Ala Val Glu Asn Leu Ala Lys Ala Ala Lys Glu Met Leu
            180                 185                 190

Ala Asn Ser Val Lys Glu Leu Thr Ser Pro Ile Val Ala Glu Ser Pro
        195                 200                 205

Lys Asn Pro
    210


<210> SEQ ID NO 52
<211> LENGTH: 208
<212> TYPE: PRT
<213> ORGANISM: Borrelia mayonii

<400> SEQUENCE: 52

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Ala Ser Asn Ser Ala
            20                  25                  30

Asp Glu Ser Ala Lys Gly Pro Asn Leu Thr Glu Ile Ser Lys Lys Ile
        35                  40                  45

Thr Asp Ser Asn Ala Val Val Leu Ala Val Lys Glu Val Glu Ala Leu
    50                  55                  60
```

Val Ala Ser Ile Asp Glu Leu Ala Lys Ala Ile Gly Lys Lys Ile Gln
65 70 75 80

Gln Asn Asn Gly Leu Gly Asn Glu Ala Gly Lys Asn Gly Ser Leu Leu
85 90 95

Ser Gly Ile Tyr Thr Ile Ser Thr Val Ile Thr Gln Lys Leu Gly Ala
100 105 110

Leu Asn Asn Glu Glu Leu Lys Glu Arg Ile Lys Glu Ala Lys Glu Cys
115 120 125

Ser Glu Ala Phe Thr Lys Lys Leu Glu Thr Asn His Thr Asp Leu Gly
130 135 140

Lys His Asp Ala Ser Asp Asp Asp Ala Lys Lys Ala Ile Leu Arg Thr
145 150 155 160

Asn Gly Asp Lys Thr Lys Gly Ala Glu Glu Leu Glu Lys Leu Phe Lys
165 170 175

Ala Val Glu Ser Leu Ser Thr Glu Ala Lys Gly Met Leu Thr Asn Ser
180 185 190

Val Lys Gln Leu Thr Ser Pro Val Val Ala Glu Thr Pro Lys Lys Pro
195 200 205

<210> SEQ ID NO 53
<211> LENGTH: 207
<212> TYPE: PRT
<213> ORGANISM: Borrelia garinii

<400> SEQUENCE: 53

Met Lys Lys Asn Thr Leu Ser Ala Ile Leu Met Thr Leu Phe Leu Phe
1 5 10 15

Ile Ser Cys Asn Asn Ser Gly Gly Asp Thr Ala Ser Thr Asn Pro Asp
20 25 30

Glu Ser Ala Lys Gly Pro Asp Leu Thr Val Ile Ser Lys Lys Ile Thr
35 40 45

Asp Ser Asn Ala Val Val Leu Val Val Lys Glu Val Glu Ala Leu Leu
50 55 60

Ser Ser Ile Asp Glu Leu Ser Lys Ala Ile Gly Lys Lys Ile Arg Asn
65 70 75 80

Asp Gly Thr Leu Asp Asn Glu Ala Asn Arg Asn Glu Ser Leu Ile Ala
85 90 95

Gly Ala Tyr Glu Ile Ser Lys Leu Ile Thr Gln Lys Leu Ser Val Leu
100 105 110

Asn Ser Glu Glu Leu Lys Glu Lys Ile Lys Glu Ala Lys Asp Cys Ser
115 120 125

Glu Lys Phe Thr Thr Lys Leu Arg Asp Ser His Ala Glu Leu Gly Ile
130 135 140

Gln Asn Val Gln Asp Asp Asn Ala Lys Arg Ala Ile Leu Lys Thr His
145 150 155 160

Gly Asn Lys Asp Lys Gly Ala Lys Glu Leu Lys Glu Leu Ser Glu Ser
165 170 175

Leu Glu Lys Leu Ser Lys Ala Ala Gln Ala Ala Leu Ala Asn Ser Val
180 185 190

Lys Glu Leu Thr Ser Pro Val Val Ala Glu Ser Pro Lys Lys Pro
195 200 205

<210> SEQ ID NO 54
<211> LENGTH: 207
<212> TYPE: PRT
<213> ORGANISM: Borrelia bavariensis

<400> SEQUENCE: 54

Met Lys Lys Asn Thr Leu Ser Ala Ile Leu Met Thr Leu Phe Leu Phe
1 5 10 15

Ile Ser Cys Asn Asn Ser Gly Gly Asp Ser Ala Ser Thr Asn Pro Asp
20 25 30

Glu Ser Ala Lys Gly Pro Asn Leu Thr Val Ile Ser Lys Lys Ile Thr
35 40 45

Asp Ser Asn Ala Phe Leu Leu Ala Val Lys Glu Val Glu Ala Leu Leu
50 55 60

Ser Ser Ile Asp Glu Leu Ser Lys Ala Ile Gly Lys Lys Ile Lys Asn
65 70 75 80

Asp Gly Thr Leu Asp Asn Glu Ala Asn Arg Asn Glu Ser Leu Ile Ala
85 90 95

Gly Ala Tyr Glu Ile Ser Lys Leu Ile Thr Gln Lys Leu Ser Val Leu
100 105 110

Asn Ser Glu Glu Leu Lys Glu Lys Ile Lys Glu Ala Lys Asp Cys Ser
115 120 125

Glu Lys Phe Thr Thr Lys Leu Lys Asp Ser His Ala Glu Leu Gly Ile
130 135 140

Gln Ser Val Gln Asp Asp Asn Ala Lys Lys Ala Ile Leu Lys Thr His
145 150 155 160

Gly Thr Lys Asp Lys Gly Ala Lys Glu Leu Glu Glu Leu Phe Lys Ser
165 170 175

Leu Glu Ser Leu Ser Lys Ala Ala Gln Ala Ala Leu Thr Asn Ser Val
180 185 190

Lys Glu Leu Thr Asn Pro Val Val Ala Glu Thr Pro Lys Lys Pro
195 200 205

<210> SEQ ID NO 55
<211> LENGTH: 211
<212> TYPE: PRT
<213> ORGANISM: Borrelia afzelii

<400> SEQUENCE: 55

Met Lys Lys Asn Thr Leu Ser Ala Ile Leu Met Thr Leu Phe Leu Phe
1 5 10 15

Ile Ser Cys Asn Asn Ser Gly Lys Gly Gly Asp Ser Thr Ser Thr Asn
20 25 30

Pro Ala Asp Glu Ser Ala Lys Gly Pro Asn Leu Thr Glu Ile Ser Lys
35 40 45

Lys Ile Thr Asp Ser Asn Ala Phe Val Leu Ala Val Lys Glu Val Glu
50 55 60

Thr Leu Val Ala Ser Ile Asp Glu Leu Ala Thr Lys Ala Ile Gly Lys
65 70 75 80

Lys Ile Lys Asn Asp Gly Thr Leu Asp Asn Glu Ala Asn His Asn Gly
85 90 95

Ser Leu Leu Ala Gly Ala Tyr Ala Ile Ser Thr Leu Ile Thr Gln Lys
100 105 110

Leu Ser Val Leu Asn Ser Glu Glu Leu Lys Ala Glu Ile Val Lys Ala
115 120 125

Lys Lys Cys Ser Glu Asp Phe Thr Lys Lys Leu Lys Asp Lys His Thr
130 135 140

Glu Leu Gly Lys Gln Asp Ala Asn Asp Asp Asp Ala Lys Lys Ala Ile
145 150 155 160

```
Leu Lys Thr Asn Gly Asp Lys Thr Leu Gly Ala Ala Glu Leu Glu Lys
                165                 170                 175

Leu Ser Glu Ser Val Thr Ser Leu Ser Lys Ala Ala Lys Glu Ser Leu
            180                 185                 190

Thr Asn Ser Val Lys Glu Leu Thr Ser Pro Val Val Ala Glu Ser Pro
        195                 200                 205

Lys Lys Pro
    210
```

<210> SEQ ID NO 56
<211> LENGTH: 211
<212> TYPE: PRT
<213> ORGANISM: Borrelia californiensis

<400> SEQUENCE: 56

```
Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Ser Ala Ser Thr Asn
            20                  25                  30

Pro Ala Asp Glu Ser Lys Gly Pro Asn Leu Thr Glu Ile Ser Lys Lys
        35                  40                  45

Ile Thr Asp Ser Asn Ala Val Val Leu Ala Val Lys Glu Val Glu Thr
    50                  55                  60

Leu Leu Ala Ser Ile Asp Glu Leu Ala Glu Lys Ala Ile Gly Lys Lys
65                  70                  75                  80

Ile Gln Gln Asn Asn Gly Leu Gly Ala Glu Ala Asn Lys Asn Gly Ser
                85                  90                  95

Leu Leu Ala Gly Val Tyr Ser Ile Ser Thr Leu Ile Thr Glu Lys Leu
            100                 105                 110

Ser Ala Met Lys Asp Ser Gly Gly Leu Lys Ala Glu Ile Glu Lys Ala
        115                 120                 125

Lys Asp Cys Ser Glu Lys Phe Thr Lys Lys Leu Glu Thr Ser His Ala
    130                 135                 140

Glu Leu Gly Lys Asn Glu Ala Thr Asp Asp Asp Ala Lys Lys Ala Ile
145                 150                 155                 160

Leu Arg Thr Asn Gly Asp Lys Thr Lys Gly Ala Glu Glu Leu Gln Lys
                165                 170                 175

Leu Phe Glu Ser Val Gly Gly Leu Ala Lys Ala Ala Lys Glu Met Leu
            180                 185                 190

Thr Asn Ser Val Lys Glu Leu Thr Ser Pro Val Val Ala Glu Thr Pro
        195                 200                 205

Lys Lys Pro
    210
```

<210> SEQ ID NO 57
<211> LENGTH: 273
<212> TYPE: PRT
<213> ORGANISM: Borrelia bissettii

<400> SEQUENCE: 57

```
Met Lys Lys Tyr Leu Leu Gly Ile Gly Leu Ile Leu Ala Leu Ile Ala
1               5                   10                  15

Cys Lys Gln Asn Val Ser Gly Leu Asp Glu Lys Asn Ser Val Ser Val
            20                  25                  30

Asp Leu Pro Gly Glu Met Lys Val Leu Val Ser Lys Glu Lys Asp Lys
        35                  40                  45
```

```
Asp Gly Lys Tyr Ser Leu Met Ala Thr Val Asp Lys Leu Glu Leu Lys
    50                  55                  60

Gly Thr Ser Asp Lys Asn Asn Gly Ser Gly Ile Leu Glu Gly Val Lys
65                  70                  75                  80

Ala Asp Lys Ser Lys Val Lys Leu Thr Val Ser Glu Asp Leu Ser Thr
                85                  90                  95

Thr Thr Leu Glu Val Leu Lys Glu Asp Gly Lys Thr Leu Val Ser Lys
            100                 105                 110

Lys Thr Thr Ser Lys Asp Lys Ser Ser Thr Glu Glu Lys Phe Asn Asp
        115                 120                 125

Lys Gly Glu Leu Ala Glu Lys Thr Ile Val Arg Ala Asn Gly Thr Arg
    130                 135                 140

Leu Glu Tyr Thr Glu Val Lys Ser Asp Gly Ser Gly Lys Ala Lys Glu
145                 150                 155                 160

Thr Leu Lys Asp Tyr Ala Leu Glu Gly Thr Leu Thr Ala Glu Lys Ala
                165                 170                 175

Thr Leu Val Val Lys Glu Gly Thr Val Thr Leu Ser Lys His Ile Ser
            180                 185                 190

Lys Ser Gly Glu Val Thr Ala Glu Leu Asn Asp Thr Asp Ser Ala Gln
        195                 200                 205

Ala Thr Lys Lys Thr Gly Lys Trp Asp Ala Gly Thr Ser Thr Leu Thr
    210                 215                 220

Ile Ser Val Asn Ser Lys Lys Thr Lys Asn Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys


<210> SEQ ID NO 58
<211> LENGTH: 273
<212> TYPE: PRT
<213> ORGANISM: Borrelia mayonii

<400> SEQUENCE: 58

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Ile Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Val Ser Asp Asp Leu Ser Lys
                85                  90                  95

Thr Thr Leu Glu Val Leu Lys Glu Asp Gly Lys Thr Leu Val Ser Arg
            100                 105                 110

Lys Val Thr Ser Lys Asp Lys Ser Ser Thr Glu Glu Lys Phe Asn Glu
        115                 120                 125

Lys Gly Glu Leu Ala Glu Lys Thr Met Thr Arg Ala Asp Glu Thr Arg
    130                 135                 140
```

Leu Glu Tyr Thr Glu Ile Lys Ser Asp Gly Ser Gly Lys Ala Lys Glu
145 150 155 160

Val Leu Lys Gly Tyr Ala Leu Glu Gly Thr Leu Thr Ala Glu Lys Thr
165 170 175

Thr Leu Val Val Lys Glu Gly Thr Val Thr Leu Ser Lys Asn Ile Ser
180 185 190

Lys Ser Gly Glu Val Thr Ala Glu Leu Asn Asp Thr Asp Ser Ala Ala
195 200 205

Ala Thr Lys Lys Thr Gly Ala Trp Asn Ser Gly Thr Ser Thr Leu Thr
210 215 220

Ile Thr Ala Asn Ser Lys Lys Thr Lys Asp Leu Val Phe Thr Lys Glu
225 230 235 240

Asn Thr Ile Thr Val Gln Lys Tyr Asp Thr Ala Gly Ile Lys Leu Glu
245 250 255

Gly Ser Ala Val Glu Ile Lys Thr Leu Asp Glu Leu Lys Asn Ala Leu
260 265 270

Lys

<210> SEQ ID NO 59
<211> LENGTH: 273
<212> TYPE: PRT
<213> ORGANISM: Borrelia burgdorferi B31

<400> SEQUENCE: 59

Met Lys Lys Tyr Leu Leu Gly Ile Gly Leu Ile Leu Ala Leu Ile Ala
1 5 10 15

Cys Lys Gln Asn Val Ser Ser Leu Asp Glu Lys Asn Ser Val Ser Val
20 25 30

Asp Leu Pro Gly Glu Met Lys Val Leu Val Ser Lys Glu Lys Asn Lys
35 40 45

Asp Gly Lys Tyr Asp Leu Ile Ala Thr Val Asp Lys Leu Glu Leu Lys
50 55 60

Gly Thr Ser Asp Lys Asn Asn Gly Ser Gly Val Leu Glu Gly Val Lys
65 70 75 80

Ala Asp Lys Ser Lys Val Lys Leu Thr Ile Ser Asp Asp Leu Gly Gln
85 90 95

Thr Thr Leu Glu Val Phe Lys Glu Asp Gly Lys Thr Leu Val Ser Lys
100 105 110

Lys Val Thr Ser Lys Asp Lys Ser Ser Thr Glu Glu Lys Phe Asn Glu
115 120 125

Lys Gly Glu Val Ser Glu Lys Ile Ile Thr Arg Ala Asp Gly Thr Arg
130 135 140

Leu Glu Tyr Thr Gly Ile Lys Ser Asp Gly Ser Gly Lys Ala Lys Glu
145 150 155 160

Val Leu Lys Gly Tyr Val Leu Glu Gly Thr Leu Thr Ala Glu Lys Thr
165 170 175

Thr Leu Val Val Lys Glu Gly Thr Val Thr Leu Ser Lys Asn Ile Ser
180 185 190

Lys Ser Gly Glu Val Ser Val Glu Leu Asn Asp Thr Asp Ser Ser Ala
195 200 205

Ala Thr Lys Lys Thr Ala Ala Trp Asn Ser Gly Thr Ser Thr Leu Thr
210 215 220

Ile Thr Val Asn Ser Lys Lys Thr Lys Asp Leu Val Phe Thr Lys Glu
225 230 235 240

Asn Thr Ile Thr Val Gln Gln Tyr Asp Ser Asn Gly Thr Lys Leu Glu
245 250 255

Gly Ser Ala Val Glu Ile Thr Lys Leu Asp Glu Ile Lys Asn Ala Leu
260 265 270

Lys

<210> SEQ ID NO 60
<211> LENGTH: 273
<212> TYPE: PRT
<213> ORGANISM: Borrelia burgdorferi 297

<400> SEQUENCE: 60

Met Lys Lys Tyr Leu Leu Gly Ile Gly Leu Ile Leu Ala Leu Ile Ala
1 5 10 15

Cys Lys Gln Asn Val Ser Ser Leu Asp Glu Lys Asn Ser Val Ser Val
20 25 30

Asp Leu Pro Gly Glu Met Asn Val Leu Val Ser Lys Glu Lys Asn Lys
35 40 45

Asp Gly Lys Tyr Asp Leu Ile Ala Thr Val Asp Lys Leu Glu Leu Lys
50 55 60

Gly Thr Ser Asp Lys Asn Asn Gly Ser Gly Val Leu Glu Gly Val Lys
65 70 75 80

Ala Asp Lys Ser Lys Val Lys Leu Thr Ile Ser Asp Asp Leu Gly Gln
85 90 95

Thr Thr Leu Glu Val Phe Lys Glu Asp Gly Lys Thr Leu Val Ser Lys
100 105 110

Lys Val Thr Ser Lys Asp Lys Ser Ser Thr Glu Glu Lys Phe Asn Glu
115 120 125

Lys Gly Glu Val Ser Glu Lys Ile Ile Thr Arg Ala Asp Gly Thr Arg
130 135 140

Leu Glu Tyr Thr Glu Ile Lys Ser Asp Gly Ser Gly Lys Ala Lys Glu
145 150 155 160

Val Leu Lys Gly Tyr Val Leu Glu Gly Thr Leu Thr Ala Glu Lys Thr
165 170 175

Thr Leu Val Val Lys Glu Gly Thr Val Thr Leu Ser Lys Asn Ile Ser
180 185 190

Lys Ser Gly Glu Val Ser Val Glu Leu Asn Asp Thr Asp Ser Ser Ala
195 200 205

Ala Thr Lys Lys Thr Ala Ala Trp Asn Ser Gly Thr Ser Thr Leu Thr
210 215 220

Ile Thr Val Asn Ser Lys Lys Thr Lys Asp Leu Val Phe Thr Lys Glu
225 230 235 240

Asn Thr Ile Thr Val Gln Gln Tyr Asp Ser Asn Gly Thr Lys Leu Glu
245 250 255

Gly Ser Ala Val Glu Ile Thr Lys Leu Asp Glu Ile Lys Asn Ala Leu
260 265 270

Lys

<210> SEQ ID NO 61
<211> LENGTH: 272
<212> TYPE: PRT
<213> ORGANISM: Borrelia californiensis

<400> SEQUENCE: 61

Met Lys Lys Tyr Leu Leu Gly Ile Gly Leu Ile Leu Ala Leu Ile Ala

-continued

```
1               5                   10                  15

Lys Gln Asn Val Ser Ser Leu Asp Glu Lys Asn Ser Val Ser Val Asp
            20                  25                  30

Leu Pro Gly Glu Met Lys Val Leu Val Ser Lys Glu Lys Asp Lys Asp
        35                  40                  45

Gly Lys Tyr Ser Leu Met Ala Thr Val Asp Lys Leu Glu Leu Lys Gly
    50                  55                  60

Thr Ser Asp Lys Asn Asn Gly Ser Gly Val Leu Glu Gly Val Lys Asp
65                  70                  75                  80

Asp Lys Ser Lys Val Lys Leu Thr Val Ser Asp Asp Leu Ser Thr Thr
                85                  90                  95

Thr Leu Glu Val Leu Lys Glu Asp Gly Lys Thr Leu Val Ser Arg Lys
            100                 105                 110

Glu Thr Ser Lys Asp Lys Ser Ser Thr Glu Glu Lys Phe Asn Glu Lys
        115                 120                 125

Gly Glu Leu Thr Glu Lys Ile Met Glu Arg Ser Asn Gly Thr Arg Leu
    130                 135                 140

Glu Tyr Thr Glu Ile Lys Thr Asp Gly Ser Gly Lys Ala Lys Glu Thr
145                 150                 155                 160

Leu Lys Asp Phe Val Leu Glu Gly Thr Leu Thr Thr Glu Lys Ala Ile
                165                 170                 175

Leu Thr Val Lys Glu Gly Thr Val Thr Leu Asn Lys Asn Ile Ser Lys
            180                 185                 190

Ser Gly Glu Val Thr Val Asp Leu Asn Asp Thr Ser Thr Thr Ala Ala
        195                 200                 205

Thr Lys Lys Thr Gly Lys Trp Asp Ser Ser Thr Ser Thr Leu Thr Val
    210                 215                 220

Ser Val Asn Ser Lys Lys Thr Lys Asp Leu Val Phe Thr Lys Gln Asp
225                 230                 235                 240

Thr Ile Thr Val Gln Lys Tyr Asp Ser Ala Gly Thr Asn Leu Glu Gly
                245                 250                 255

Thr Ala Val Glu Ile Lys Thr Leu Asp Glu Ile Lys Asn Ala Leu Lys
            260                 265                 270


<210> SEQ ID NO 62
<211> LENGTH: 273
<212> TYPE: PRT
<213> ORGANISM: Borrelia spielmanii

<400> SEQUENCE: 62

Met Lys Lys Tyr Leu Leu Gly Ile Gly Leu Ile Leu Ala Leu Ile Ala
1               5                   10                  15

Cys Lys Gln Asn Val Ser Gly Leu Asp Glu Lys Asn Ser Thr Ser Val
            20                  25                  30

Asp Val Pro Gly Glu Leu Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asp Gly Ser Gly Val Leu Glu Gly Val Lys
65                  70                  75                  80

Ala Asp Lys Ser Lys Val Lys Leu Thr Ile Ser Asp His Leu Ser Lys
                85                  90                  95

Thr Thr Phe Glu Val Phe Lys Glu Asp Gly Lys Thr Leu Val Ser Arg
            100                 105                 110
```

```
Asn Val Asn Ser Lys Asp Lys Ser Ser Thr Lys Glu Lys Phe Asn Glu
        115                 120                 125

Lys Gly Glu Leu Ser Glu Lys Thr Leu Val Arg Ala Asn Gly Thr Lys
    130                 135                 140

Leu Glu Tyr Thr Glu Ile Lys Ser Asp Gly Thr Gly Lys Ala Lys Glu
145                 150                 155                 160

Val Leu Lys Asp Phe Thr Leu Glu Gly Thr Leu Ala Asn Glu Lys Ala
                165                 170                 175

Thr Leu Thr Val Lys Glu Gly Thr Val Thr Leu Ser Lys Asn Ile Asp
            180                 185                 190

Lys Ser Gly Glu Val Thr Val Ala Leu Asn Asp Thr Asp Ser Thr Ala
        195                 200                 205

Ala Thr Lys Lys Thr Gly Ala Trp Asp Ser Lys Thr Ser Thr Leu Thr
    210                 215                 220

Ile Thr Val Asn Ser Lys Lys Thr Lys Asp Leu Val Phe Thr Lys Gln
225                 230                 235                 240

Asp Thr Ile Thr Val Gln Lys Tyr Asp Ser Ala Gly Thr Thr Leu Glu
                245                 250                 255

Gly Ser Ala Val Glu Ile Lys Thr Leu Asp Glu Leu Lys Asn Ala Leu
            260                 265                 270

Lys


<210> SEQ ID NO 63
<211> LENGTH: 274
<212> TYPE: PRT
<213> ORGANISM: Borrelia valaisiana

<400> SEQUENCE: 63

Met Lys Lys Tyr Leu Leu Gly Ile Gly Leu Ile Leu Ala Leu Ile Ala
1               5                   10                  15

Cys Ala Lys Gln Asn Val Ser Ser Leu Asp Glu Lys Asn Ser Ala Ser
            20                  25                  30

Val Asp Leu Pro Gly Glu Met Lys Val Leu Val Ser Lys Glu Lys Asp
        35                  40                  45

Lys Asp Gly Lys Tyr Ser Leu Met Ala Thr Val Asp Lys Val Glu Leu
    50                  55                  60

Lys Gly Thr Ser Asp Lys Asn Asn Gly Ser Gly Thr Leu Glu Gly Val
65                  70                  75                  80

Lys Asp Asp Lys Ser Lys Val Lys Leu Thr Ile Ser Asp Asp Leu Asn
                85                  90                  95

Lys Thr Thr Phe Glu Thr Phe Lys Glu Asp Gly Lys Thr Leu Val Ser
            100                 105                 110

Arg Lys Val Asn Ser Lys Asp Lys Ser Ser Thr Val Glu Lys Phe Asn
        115                 120                 125

Glu Lys Gly Glu Leu Ser Glu Lys Thr Ile Thr Arg Glu Asn Gly Thr
    130                 135                 140

Arg Leu Glu Tyr Thr Glu Ile Lys Ser Asp Gly Thr Gly Lys Ala Lys
145                 150                 155                 160

Glu Val Leu Lys Asp Phe Thr Leu Glu Gly Thr Leu Ala Ala Asp Lys
                165                 170                 175

Thr Thr Leu Glu Val Lys Glu Gly Thr Val Thr Leu Ser Lys His Ile
            180                 185                 190

Pro Asn Ser Gly Glu Val Thr Val Glu Ile Asn Asp Thr Ser Thr Thr
        195                 200                 205
```

```
Gln Ala Thr Lys Lys Thr Gly Lys Trp Asp Ala Lys Thr Ser Thr Leu
    210                 215                 220

Thr Ile Ala Val Asn Asn Lys Asn Thr Lys Ser Leu Val Phe Thr Lys
225                 230                 235                 240

Glu Asp Thr Ile Thr Val Gln Asn Tyr Asp Ser Ala Gly Thr Asn Leu
                245                 250                 255

Glu Gly Thr Ala Val Glu Ile Lys Thr Leu Asp Glu Leu Lys Asn Ala
            260                 265                 270

Leu Lys


<210> SEQ ID NO 64
<211> LENGTH: 273
<212> TYPE: PRT
<213> ORGANISM: Borrelia afzelii

<400> SEQUENCE: 64

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Ala Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys


<210> SEQ ID NO 65
<211> LENGTH: 274
<212> TYPE: PRT
```

```
<213> ORGANISM: Borrelia garinii

<400> SEQUENCE: 65

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Lys Glu Leu Lys Asp Ala
            260                 265                 270

Leu Lys


<210> SEQ ID NO 66
<211> LENGTH: 273
<212> TYPE: PRT
<213> ORGANISM: Borrelia bavariensis

<400> SEQUENCE: 66

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Ser Asn Gly Ser Gly Thr Leu Glu Gly Glu Lys
65                  70                  75                  80
```

```
Ser Asp Lys Ser Lys Ala Lys Leu Thr Ile Ser Glu Asp Leu Ser Lys
                85                  90                  95

Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
        115                 120                 125

Lys Gly Glu Leu Ser Glu Lys Thr Ile Leu Arg Ala Asn Gly Thr Arg
    130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
                165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
        195                 200                 205

Ala Thr Lys Lys Thr Gly Lys Trp Asp Ser Asn Thr Ser Thr Leu Thr
    210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
                245                 250                 255

Gly Asn Ala Val Glu Ile Lys Thr Leu Asp Glu Leu Lys Asn Ala Leu
            260                 265                 270

Lys
```

<210> SEQ ID NO 67
<211> LENGTH: 339
<212> TYPE: PRT
<213> ORGANISM: Borrelia burgdorferi B31

<400> SEQUENCE: 67

```
Met Asn Lys Ile Leu Leu Leu Ile Leu Leu Glu Ser Ile Val Phe Leu
1               5                   10                  15

Ser Cys Ser Gly Lys Gly Ser Leu Gly Ser Glu Ile Pro Lys Val Ser
            20                  25                  30

Leu Ile Ile Asp Gly Thr Phe Asp Asp Lys Ser Phe Asn Glu Ser Ala
        35                  40                  45

Leu Asn Gly Val Lys Lys Val Lys Glu Glu Phe Lys Ile Glu Leu Val
    50                  55                  60

Leu Lys Glu Ser Ser Ser Asn Ser Tyr Leu Ser Asp Leu Glu Gly Leu
65                  70                  75                  80

Lys Asp Ala Gly Ser Asp Leu Ile Trp Leu Ile Gly Tyr Arg Phe Ser
                85                  90                  95

Asp Val Ala Lys Val Ala Ala Leu Gln Asn Pro Asp Met Lys Tyr Ala
            100                 105                 110

Ile Ile Asp Pro Ile Tyr Ser Asn Asp Pro Ile Pro Ala Asn Leu Val
        115                 120                 125

Gly Met Thr Phe Arg Ala Gln Glu Gly Ala Phe Leu Thr Gly Tyr Ile
    130                 135                 140

Ala Ala Lys Leu Ser Lys Thr Gly Lys Ile Gly Phe Leu Gly Gly Ile
145                 150                 155                 160

Glu Gly Glu Ile Val Asp Ala Phe Arg Tyr Gly Tyr Glu Ala Gly Ala
                165                 170                 175
```

```
Lys Tyr Ala Asn Lys Asp Ile Lys Ile Ser Thr Gln Tyr Ile Gly Ser
            180                 185                 190

Phe Ala Asp Leu Glu Ala Gly Arg Ser Val Ala Thr Arg Met Tyr Ser
        195                 200                 205

Asp Glu Ile Asp Ile Ile His His Ala Ala Gly Leu Gly Gly Ile Gly
    210                 215                 220

Ala Ile Glu Val Ala Lys Glu Leu Gly Ser Gly His Tyr Ile Ile Gly
225                 230                 235                 240

Val Asp Glu Asp Gln Ala Tyr Leu Ala Pro Asp Asn Val Ile Thr Ser
                245                 250                 255

Thr Thr Lys Asp Val Gly Arg Ala Leu Asn Ile Phe Thr Ser Asn His
            260                 265                 270

Leu Lys Thr Asn Thr Phe Glu Gly Gly Lys Leu Ile Asn Tyr Gly Leu
        275                 280                 285

Lys Glu Gly Val Val Gly Phe Val Arg Asn Pro Lys Met Ile Ser Phe
    290                 295                 300

Glu Leu Glu Lys Glu Ile Asp Asn Leu Ser Ser Lys Ile Ile Asn Lys
305                 310                 315                 320

Glu Ile Ile Val Pro Ser Asn Lys Glu Ser Tyr Glu Lys Phe Leu Lys
                325                 330                 335

Glu Phe Ile


<210> SEQ ID NO 68
<211> LENGTH: 339
<212> TYPE: PRT
<213> ORGANISM: Borrelia burgdorferi 297

<400> SEQUENCE: 68

Met Asn Lys Ile Leu Leu Leu Ile Leu Leu Glu Ser Ile Val Phe Leu
1               5                   10                  15

Ser Cys Ser Gly Lys Gly Ser Leu Gly Ser Glu Ile Pro Lys Val Ser
            20                  25                  30

Leu Ile Ile Asp Gly Thr Phe Asp Asp Lys Ser Phe Asn Glu Ser Ala
        35                  40                  45

Leu Asn Gly Val Lys Lys Val Lys Glu Glu Phe Lys Ile Glu Leu Val
    50                  55                  60

Leu Lys Glu Ser Ser Ser Asn Ser Tyr Leu Ser Asp Leu Glu Gly Leu
65                  70                  75                  80

Lys Asp Ala Gly Ser Asp Leu Ile Trp Leu Ile Gly Tyr Arg Phe Ser
                85                  90                  95

Asp Val Ala Lys Val Ala Ala Leu Gln Asn Pro Asp Met Lys Tyr Ala
            100                 105                 110

Ile Ile Asp Pro Ile Tyr Ser Asn Asp Pro Ile Pro Ala Asn Leu Val
        115                 120                 125

Gly Met Thr Phe Arg Ala Gln Glu Gly Ala Phe Leu Thr Gly Tyr Ile
    130                 135                 140

Ala Ala Lys Leu Ser Lys Thr Gly Lys Ile Gly Phe Leu Gly Gly Ile
145                 150                 155                 160

Glu Gly Glu Ile Val Asp Ala Phe Arg Tyr Gly Tyr Glu Ala Gly Ala
                165                 170                 175

Lys Tyr Ala Asn Lys Asp Ile Lys Ile Ser Thr Gln Tyr Ile Gly Ser
            180                 185                 190

Phe Ala Asp Leu Glu Ala Gly Arg Ser Val Ala Thr Arg Met Tyr Ser
        195                 200                 205
```

Asp Glu Ile Asp Ile Ile His His Ala Ala Gly Leu Gly Gly Ile Gly
210 215 220

Ala Ile Glu Val Ala Lys Glu Leu Gly Ser Gly His Tyr Ile Ile Gly
225 230 235 240

Val Asp Glu Asp Gln Ala Tyr Leu Ala Pro Asp Asn Val Ile Thr Ser
245 250 255

Thr Thr Lys Asp Val Gly Arg Ala Leu Asn Ile Phe Thr Ser Asn His
260 265 270

Leu Lys Thr Asn Thr Ser Glu Gly Gly Lys Leu Ile Asn Tyr Gly Leu
275 280 285

Lys Glu Gly Val Val Gly Phe Val Arg Asn Pro Lys Met Ile Ser Phe
290 295 300

Glu Leu Glu Lys Glu Ile Asp Asn Leu Ser Ser Lys Ile Ile Asn Lys
305 310 315 320

Glu Ile Ile Val Pro Ser Asn Lys Glu Ser Tyr Glu Lys Phe Leu Lys
325 330 335

Glu Phe Ile

<210> SEQ ID NO 69
<211> LENGTH: 339
<212> TYPE: PRT
<213> ORGANISM: Borrelia afzelii

<400> SEQUENCE: 69

Met Asn Lys Leu Leu Leu Leu Ile Leu Phe Glu Gly Val Ile Phe Leu
1 5 10 15

Ser Cys Ser Gly Lys Ser Gly Leu Glu Ser Gly Ile Pro Lys Val Ser
20 25 30

Leu Val Ile Asp Gly Thr Phe Asp Asp Lys Ser Phe Asn Glu Ser Ala
35 40 45

Leu Asn Gly Val Lys Lys Leu Lys Glu Glu Phe Glu Ile Glu Leu Val
50 55 60

Leu Lys Glu Ser Ser Thr Asn Ser Tyr Leu Ser Asp Leu Glu Gly Leu
65 70 75 80

Lys Asp Ala Gly Ser Asn Leu Ile Trp Leu Ile Gly Tyr Lys Phe Ser
85 90 95

Asp Val Ala Lys Ala Val Ser Leu Gln Asn Ser Glu Met Lys Tyr Ala
100 105 110

Ile Ile Asp Pro Val Tyr Ser Asn Glu Pro Ile Pro Ala Asn Leu Val
115 120 125

Gly Met Thr Phe Arg Ala Gln Glu Gly Ala Phe Leu Thr Gly Tyr Ile
130 135 140

Ala Ala Lys Val Ser Lys Thr Gly Lys Ile Gly Phe Leu Gly Gly Ile
145 150 155 160

Glu Gly Asp Ile Val Asp Ala Phe Arg Tyr Gly Tyr Glu Ala Gly Ala
165 170 175

Lys Tyr Ala Asn Lys Asp Ile Lys Ile Phe Ser Gln Tyr Ile Gly Ser
180 185 190

Phe Ser Asp Leu Glu Ala Gly Arg Ser Val Ala Thr Lys Met Tyr Ser
195 200 205

Asp Gly Ile Asp Ile Ile His His Ala Ala Gly Leu Gly Gly Ile Gly
210 215 220

Ala Ile Glu Val Ala Lys Glu Leu Gly Ser Gly His Tyr Ile Ile Gly
225 230 235 240

```
Val Asp Glu Asp Gln Ser Tyr Leu Ala Pro Asn Asn Val Ile Thr Ser
                245                 250                 255

Thr Thr Lys Asp Val Gly Arg Ser Leu Asn Leu Phe Thr Ser Asn Tyr
            260                 265                 270

Leu Lys Thr Asn Thr Phe Glu Gly Gly Lys Leu Ile Asn Tyr Gly Leu
        275                 280                 285

Lys Glu Gly Val Val Gly Phe Val Arg Asn Pro Lys Met Ile Pro Phe
    290                 295                 300

Glu Val Glu Lys Glu Ile Asp Ser Leu Ser Ser Lys Ile Ile Asn Lys
305                 310                 315                 320

Glu Val Ile Val Pro Tyr Asn Lys Glu Ser Tyr Glu Lys Phe Leu Lys
                325                 330                 335

Glu Phe Ile


<210> SEQ ID NO 70
<211> LENGTH: 339
<212> TYPE: PRT
<213> ORGANISM: Borrelia spielmanii

<400> SEQUENCE: 70

Met Asn Lys Leu Leu Leu Phe Ile Leu Leu Glu Gly Ile Ile Phe Leu
1               5                   10                  15

Ser Cys Ser Asp Lys Gly Gly Leu Glu Asn Lys Ile Pro Lys Val Ser
            20                  25                  30

Leu Ile Ile Asp Gly Thr Phe Asp Asp Lys Ser Phe Asn Glu Ser Ala
        35                  40                  45

Leu Asn Gly Val Lys Lys Leu Lys Glu Glu Phe Glu Ile Asp Leu Val
    50                  55                  60

Leu Lys Glu Ser Ser Thr Asn Ser Tyr Val Ser Asp Leu Glu Gly Leu
65                  70                  75                  80

Lys Asp Ala Gly Ser Asn Leu Ile Trp Leu Ile Gly Tyr Lys Phe Ser
                85                  90                  95

Asp Val Ala Lys Ala Val Ser Leu Gln Asn Ser Glu Met Lys Tyr Ala
            100                 105                 110

Ile Ile Asp Pro Val Tyr Ser Ser Glu Pro Ile Pro Ala Asn Leu Val
        115                 120                 125

Gly Met Thr Phe Arg Ala Gln Glu Gly Ala Phe Leu Thr Gly Tyr Ile
    130                 135                 140

Ala Ser Lys Val Ser Lys Thr Gly Lys Ile Gly Phe Leu Gly Gly Ile
145                 150                 155                 160

Glu Gly Asp Ile Val Asp Ala Phe Arg Tyr Gly Tyr Glu Ala Gly Ala
                165                 170                 175

Lys Tyr Ala Asn Lys Asp Ile Lys Ile Phe Ser Gln Tyr Ile Gly Ser
            180                 185                 190

Phe Ala Asp Ile Glu Ala Gly Arg Ser Val Ala Thr Lys Met Tyr Ser
        195                 200                 205

Asp Gly Ile Asp Ile Ile His His Ala Ala Gly Leu Gly Gly Ile Gly
    210                 215                 220

Ala Ile Glu Val Ala Lys Glu Leu Gly Ser Gly His Tyr Ile Ile Gly
225                 230                 235                 240

Val Asp Glu Asp Gln Ser Tyr Leu Ala Pro Asn Asn Val Ile Thr Ser
                245                 250                 255

Ser Thr Lys Asp Val Gly Arg Ser Leu Asn Leu Phe Thr Ser Asn Tyr
            260                 265                 270
```

Leu Lys Thr Asn Asn Phe Glu Gly Gly Lys Leu Ile Asn Tyr Gly Leu
275 280 285

Lys Glu Gly Val Val Gly Phe Val Arg Asn Pro Lys Met Ile Pro Phe
290 295 300

Glu Val Glu Lys Glu Ile Asp Ser Leu Ser Gly Lys Ile Ile Asn Lys
305 310 315 320

Glu Val Ile Val Pro Tyr Asn Lys Glu Ser Tyr Glu Lys Phe Leu Lys
325 330 335

Glu Phe Leu

<210> SEQ ID NO 71
<211> LENGTH: 339
<212> TYPE: PRT
<213> ORGANISM: Borrelia valaisiana

<400> SEQUENCE: 71

Met Ser Lys Leu Leu Leu Leu Ile Leu Phe Glu Ser Ile Ile Phe Leu
1 5 10 15

Ser Cys Ser Gly Lys Gly Ser Leu Glu Gly Gly Ile Pro Lys Val Ser
20 25 30

Val Ile Ile Asp Gly Thr Phe Asp Asp Lys Ser Phe Asn Glu Ser Ala
35 40 45

Leu Asn Gly Ile Lys Lys Val Lys Glu Glu Phe Lys Val Glu Phe Val
50 55 60

Leu Lys Glu Ser Ser Ser Asn Ser Tyr Leu Ser Asp Leu Glu Gly Leu
65 70 75 80

Lys Asp Thr Gly Ser Asn Leu Ile Trp Leu Ile Gly Tyr Arg Phe Ser
85 90 95

Asp Val Ala Lys Val Val Ser Leu Gln Asn Ser Glu Val Lys Tyr Ala
100 105 110

Ile Ile Asp Pro Val Tyr Ser Ser Glu Pro Ile Pro Ala Asn Leu Val
115 120 125

Gly Met Thr Phe Arg Ala Gln Glu Gly Ala Phe Leu Thr Gly Tyr Ile
130 135 140

Ala Ser Lys Val Ser Lys Thr Gly Lys Ile Gly Phe Leu Gly Gly Ile
145 150 155 160

Lys Ser Glu Ile Val Asp Ala Phe Arg Tyr Gly Tyr Glu Ala Gly Ala
165 170 175

Lys Tyr Ala Asn Lys Asp Ile Lys Ile Phe Thr His Tyr Ile Gly Ser
180 185 190

Phe Ala Asp Leu Glu Ala Ser Arg Ser Ile Ala Ile Lys Met Tyr Ser
195 200 205

Asp Gly Ile Asp Ile Ile His His Ala Ala Gly Leu Gly Gly Ile Gly
210 215 220

Ala Ile Glu Val Ala Lys Glu Leu Gly Ser Gly His Tyr Ile Ile Gly
225 230 235 240

Val Asp Glu Asp Gln Ser Tyr Leu Ala Pro Asp Asn Val Ile Thr Ser
245 250 255

Ser Thr Lys Asp Val Gly Arg Ala Leu Asn Ile Phe Thr Ser Asn Tyr
260 265 270

Leu Lys Thr Asn Thr Phe Glu Gly Gly Lys Leu Ile Asn Tyr Gly Leu
275 280 285

Lys Glu Gly Val Val Gly Phe Val Arg Asn Pro Lys Met Ile Pro Phe
290 295 300

Glu Leu Glu Lys Glu Ile Asp Ser Ile Ser Ser Lys Ile Ile Asn Lys
305 310 315 320

Glu Val Ile Val Pro Tyr Asn Lys Glu Ser Tyr Glu Lys Phe Leu Lys
325 330 335

Glu Phe Ile

<210> SEQ ID NO 72
<211> LENGTH: 337
<212> TYPE: PRT
<213> ORGANISM: Borrelia garinii

<400> SEQUENCE: 72

Met Asn Lys Ser Leu Leu Leu Ile Leu Phe Glu Cys Ile Ile Phe Leu
1 5 10 15

Ser Cys Gly Gly Lys Gly Ser Leu Glu Ser Glu Ile Pro Lys Val Ser
20 25 30

Leu Ile Ile Asp Gly Thr Phe Asp Asp Lys Ser Phe Asn Glu Ser Ala
35 40 45

Leu Asn Gly Ile Lys Lys Val Lys Glu Glu Phe Lys Ile Glu Pro Val
50 55 60

Leu Lys Glu Ser Ser Ile Asn Ser Tyr Leu Ser Asp Leu Glu Gly Leu
65 70 75 80

Lys Asp Thr Gly Ser Asn Leu Ile Trp Leu Ile Gly Tyr Lys Phe Ser
85 90 95

Asp Val Ala Lys Ala Val Ser Leu Gln Asn Pro Glu Ile Lys Tyr Ala
100 105 110

Ile Ile Asp Pro Ile Tyr Ser Asp Glu Pro Ile Pro Ala Asn Leu Val
115 120 125

Gly Met Thr Phe Arg Ser Gln Glu Gly Ala Phe Leu Thr Gly Tyr Ile
130 135 140

Ala Ala Lys Val Ser Lys Thr Gly Lys Ile Gly Phe Leu Gly Gly Ile
145 150 155 160

Glu Gly Glu Ile Val Asp Ser Phe Arg Tyr Gly Tyr Glu Ala Gly Ala
165 170 175

Lys Tyr Ala Asn Lys Asp Ile Lys Ile Ser Ala Tyr Tyr Ile Gly Ser
180 185 190

Phe Ala Asp Leu Glu Ala Gly Arg Ser Val Ala Thr Lys Met Tyr Ser
195 200 205

Asp Gly Ile Asp Ile Ile His His Ala Ala Gly Leu Gly Gly Ile Gly
210 215 220

Ala Ile Glu Val Ala Lys Glu Leu Gly Ser Gly His Tyr Ile Ile Gly
225 230 235 240

Val Asp Glu Asp Gln Ser Tyr Leu Ala Pro Asn Asn Ile Ile Thr Ser
245 250 255

Ala Thr Lys Asp Val Gly Arg Ser Leu Asn Ile Phe Thr Ser Asn Tyr
260 265 270

Leu Lys Thr Asn Thr Phe Glu Gly Gly Arg Leu Ile Asn Tyr Gly Leu
275 280 285

Lys Glu Gly Val Val Gly Phe Val Lys Asn Pro Lys Met Ile Pro Phe
290 295 300

Glu Leu Glu Lys Glu Ile Asp Asn Leu Ser Ser Lys Ile Ile Asn Lys
305 310 315 320

Glu Ile Ile Val Pro Tyr Asn Lys Glu Ser Tyr Glu Lys Phe Leu Lys
325 330 335

Glu

<210> SEQ ID NO 73
<211> LENGTH: 339
<212> TYPE: PRT
<213> ORGANISM: Artificial Sequence
<220> FEATURE:
<223> OTHER INFORMATION: Synthetic Oligonucleotide
<220> FEATURE:
<221> NAME/KEY: X
<222> LOCATION: (12)..(12)
<223> OTHER INFORMATION: C, G, or S
<220> FEATURE:
<221> NAME/KEY: X
<222> LOCATION: (13)..(13)
<223> OTHER INFORMATION: I or V
<220> FEATURE:
<221> NAME/KEY: X
<222> LOCATION: (14)..(14)
<223> OTHER INFORMATION: I or V
<220> FEATURE:
<221> NAME/KEY: X
<222> LOCATION: (27)..(27)
<223> OTHER INFORMATION: E, G, or K
<220> FEATURE:
<221> NAME/KEY: X
<222> LOCATION: (34)..(34)
<223> OTHER INFORMATION: I or V
<220> FEATURE:
<221> NAME/KEY: X
<222> LOCATION: (52)..(52)
<223> OTHER INFORMATION: I or V
<220> FEATURE:
<221> NAME/KEY: X
<222> LOCATION: (61)..(61)
<223> OTHER INFORMATION: I or V
<220> FEATURE:
<221> NAME/KEY: X
<222> LOCATION: (62)..(62)
<223> OTHER INFORMATION: E or D
<220> FEATURE:
<221> NAME/KEY: X
<222> LOCATION: (70)..(70)
<223> OTHER INFORMATION: I, S, or T
<220> FEATURE:
<221> NAME/KEY: X
<222> LOCATION: (86)..(86)
<223> OTHER INFORMATION: N or D
<220> FEATURE:
<221> NAME/KEY: X
<222> LOCATION: (108)..(108)
<223> OTHER INFORMATION: E or D
<220> FEATURE:
<221> NAME/KEY: X
<222> LOCATION: (117)..(117)
<223> OTHER INFORMATION: I or V
<220> FEATURE:
<221> NAME/KEY: X
<222> LOCATION: (121)..(121)
<223> OTHER INFORMATION: E or D
<220> FEATURE:
<221> NAME/KEY: X
<222> LOCATION: (163)..(163)
<223> OTHER INFORMATION: E or D
<220> FEATURE:
<221> NAME/KEY: X
<222> LOCATION: (187)..(187)
<223> OTHER INFORMATION: A, T, or S
<220> FEATURE:
<221> NAME/KEY: X
<222> LOCATION: (202)..(202)
<223> OTHER INFORMATION: I or V
<220> FEATURE:
<221> NAME/KEY: X
<222> LOCATION: (251)..(251)
<223> OTHER INFORMATION: N or D
<220> FEATURE:

<221> NAME/KEY: X
<222> LOCATION: (253)..(253)
<223> OTHER INFORMATION: I or V
<220> FEATURE:
<221> NAME/KEY: X
<222> LOCATION: (257)..(257)
<223> OTHER INFORMATION: A, S, or T
<220> FEATURE:
<221> NAME/KEY: X
<222> LOCATION: (322)..(322)
<223> OTHER INFORMATION: I or V

<400> SEQUENCE: 73

Met Asn Lys Leu Leu Leu Leu Ile Leu Phe Glu Xaa Xaa Xaa Phe Leu
1 5 10 15

Ser Cys Ser Gly Lys Gly Ser Leu Glu Ser Xaa Ile Pro Lys Val Ser
20 25 30

Leu Xaa Ile Asp Gly Thr Phe Asp Asp Lys Ser Phe Asn Glu Ser Ala
35 40 45

Leu Asn Gly Xaa Lys Lys Val Lys Glu Glu Phe Lys Xaa Xaa Leu Val
50 55 60

Leu Lys Glu Ser Ser Xaa Asn Ser Tyr Leu Ser Asp Leu Glu Gly Leu
65 70 75 80

Lys Asp Ala Gly Ser Xaa Leu Ile Trp Leu Ile Gly Tyr Lys Phe Ser
85 90 95

Asp Val Ala Lys Ala Val Ser Leu Gln Asn Ser Xaa Met Lys Tyr Ala
100 105 110

Ile Ile Asp Pro Xaa Tyr Ser Asn Xaa Pro Ile Pro Ala Asn Leu Val
115 120 125

Gly Met Thr Phe Arg Ala Gln Glu Gly Ala Phe Leu Thr Gly Tyr Ile
130 135 140

Ala Ala Lys Val Ser Lys Thr Gly Lys Ile Gly Phe Leu Gly Gly Ile
145 150 155 160

Glu Gly Xaa Ile Val Asp Ala Phe Arg Tyr Gly Tyr Glu Ala Gly Ala
165 170 175

Lys Tyr Ala Asn Lys Asp Ile Lys Ile Phe Xaa Gln Tyr Ile Gly Ser
180 185 190

Phe Ala Asp Leu Glu Ala Gly Arg Ser Xaa Ala Thr Lys Met Tyr Ser
195 200 205

Asp Gly Ile Asp Ile Ile His His Ala Ala Gly Leu Gly Gly Ile Gly
210 215 220

Ala Ile Glu Val Ala Lys Glu Leu Gly Ser Gly His Tyr Ile Ile Gly
225 230 235 240

Val Asp Glu Asp Gln Ser Tyr Leu Ala Pro Xaa Asn Xaa Ile Thr Ser
245 250 255

Xaa Thr Lys Asp Val Gly Arg Ser Leu Asn Ile Phe Thr Ser Asn Tyr
260 265 270

Leu Lys Thr Asn Thr Phe Glu Gly Gly Lys Leu Ile Asn Tyr Gly Leu
275 280 285

Lys Glu Gly Val Val Gly Phe Val Arg Asn Pro Lys Met Ile Pro Phe
290 295 300

Glu Leu Glu Lys Glu Ile Asp Ser Leu Ser Ser Lys Ile Ile Asn Lys
305 310 315 320

Glu Xaa Ile Val Pro Tyr Asn Lys Glu Ser Tyr Glu Lys Phe Leu Lys
325 330 335

Glu Phe Ile